(12) United States Patent
Estok et al.

(10) Patent No.: US 11,865,116 B2
(45) Date of Patent: Jan. 9, 2024

(54) TREATMENT OF CANCER WITH TG02

(71) Applicant: Cothera Bioscience, Inc., Grand Cayman (KY)

(72) Inventors: Thomas M. Estok, Williamsburg, VA (US); Eckard Weber, San Diego, CA (US); Tracy Lee Lawhon, San Diego, CA (US)

(73) Assignee: COTHERA BIOSCIENCE, INC., Grand Cayman (KY)

(*) Notice: Subject to any disclaimer, the term of this patent is extended or adjusted under 35 U.S.C. 154(b) by 860 days.

(21) Appl. No.: 16/087,966

(22) PCT Filed: Mar. 24, 2017

(86) PCT No.: PCT/US2017/023965
§ 371 (c)(1),
(2) Date: Sep. 24, 2018

(87) PCT Pub. No.: WO2017/165732
PCT Pub. Date: Sep. 28, 2017

(65) Prior Publication Data
US 2020/0323862 A1 Oct. 15, 2020

Related U.S. Application Data

(60) Provisional application No. 62/423,468, filed on Nov. 17, 2016, provisional application No. 62/312,712, filed on Mar. 24, 2016.

(51) Int. Cl.
| | |
|---|---|
| *A61K 31/529* | (2006.01) |
| *A61P 35/00* | (2006.01) |
| *A61K 33/243* | (2019.01) |
| *A61K 31/44* | (2006.01) |
| *A61K 31/454* | (2006.01) |
| *A61K 31/495* | (2006.01) |
| *A61K 31/69* | (2006.01) |
| *A61K 31/704* | (2006.01) |
| *A61K 38/07* | (2006.01) |
| *A61K 39/395* | (2006.01) |

(52) U.S. Cl.
CPC ........... *A61K 31/529* (2013.01); *A61K 31/44* (2013.01); *A61K 31/454* (2013.01); *A61K 31/495* (2013.01); *A61K 31/69* (2013.01); *A61K 31/704* (2013.01); *A61K 33/243* (2019.01); *A61K 38/07* (2013.01); *A61K 39/3955* (2013.01); *A61P 35/00* (2018.01)

(58) Field of Classification Search
CPC ..... A61K 51/00; A61K 2121/00; A61P 35/00; A61P 35/02; A61P 35/04; A61N 5/10; A61N 5/1001; A61N 5/00
See application file for complete search history.

(56) References Cited

U.S. PATENT DOCUMENTS

| | | | |
|---|---|---|---|
| 8,143,255 B2 | 3/2012 | Blanchard et al. | |
| 9,120,815 B2 | 9/2015 | Mansfield et al. | |
| 10,544,162 B2 | 1/2020 | Mansfield et al. | |
| 2020/0262843 A1 | 8/2020 | Mansfield et al. | |

FOREIGN PATENT DOCUMENTS

| | | | |
|---|---|---|---|
| WO | WO 2015/004534 A2 | 1/2015 | |
| WO | WO 2015/026634 A1 | 2/2015 | |
| WO | WO-2015095840 A1 * | 6/2015 | ......... A61K 31/4439 |
| WO | WO 2015/153870 A1 | 10/2015 | |
| WO | WO 2015/157093 A1 | 10/2015 | |
| WO | WO 2016/040892 A1 | 3/2016 | |

OTHER PUBLICATIONS

The abstract of Burrows et al (Clinical Lymphoma, Myeloma &Leukemia, 2014, Sep. 2014, p. S152, abstract No. 607) (Year: 2014).*
Abstract of Hofmeister et al (Blood, Dec. 3, 2015, vol. 126, No. 23) (Year: 2015).*
"Prescribing Information" for Kyprolis (revised Jul. 2012) (Year: 2012).*
The abstract of Barnhardt et al (Blood, Nov. 15, 2013, vol. 122, No. 21, p. 3171) (Year: 2013).*
NCT01204164 (Apr. 8, 2015 version). (Year: 2015).*
Williams et al (Journal of Medicinal Chemistry, 2012, vol. 55, pp. 169-196) (Year: 2012).*
Abstract of Park et al (Blood, Dec. 2015, vol. 126, No. 23) (Year: 2015).*
Sanchez-Martinez, Bioorganic and Medicinal Chemistry Letters, 2015, vol. 25, pp. 3420-3435 (Year: 2015).*
Flakus (IAEA Bulletin, 1982, vol. 23, pp. 31-36 (Year: 1982).*
Qaim (Radiochimica Acta, 2001, vol. 89, pp. 297-302) (Year: 2001).*
The abstract of Stepanek et al (Acta Oncologica, 1996, vol. 35, pp. 863-868) (Year: 1996).*
Hdeib and Slaon (Expert Opinion on Biological Therapy, 2011, vol. 11, pp. 799-806). (Year: 2011).*
Álvarez-Fernández, S., et al., "Potent antimyeloma activity of a novel ERK5/CDK inhibitor," *Clinical Cancer Research* 19(10): 2677-2687, American Association for Cancer Research, United States (2013).
Burrows, F., et al., "TG02: A novel, multi-kinase inhibitor with potent activity against solid tumors," *Journal of Clinical Oncology* 28(15_suppl):e13549, American Society of Clinical Oncology, United States (2010).
Goh, K. C., et al., "TG02, a novel oral multi-kinase inhibitor of (Continued)

*Primary Examiner* — Karen A. Canella
(74) *Attorney, Agent, or Firm* — Sterne, Kessler, Goldstein & Fox P.L.L.C.

(57) ABSTRACT

The present disclosure provides therapeutic methods of treating a cancer patient with TG02 and a second therapeutic agent, e.g., TG02 and an immune checkpoint inhibitor, TG02 and a COX-2 inhibitor, or TG02 and an immune checkpoint inhibitor and a COX-2 inhibitor.

8 Claims, 33 Drawing Sheets

(56) References Cited

OTHER PUBLICATIONS

CDKs, JAK2 and FLT3 with potent anti-leukemic properties," *Leukemia* 26(2): 236, Nature Publishing Group, United Kingdom (2012).

Matsumoto, F., et al., "Abstract 2487: A multi-kinase inhibitor, XL228, enhanced human cancer cell radiosensitivity and suppressed cell invasion and migration," *Cancer Research* 71(8_suppl):2487, American Association for Cancer Research, United States (2011).

Munshi, A., et al., "Radiosensitization of human melanoma cells by sorafenib (BAY 43-9006), a multi-kinase inhibitor," *Cancer Research* 66(8_Suppl):4671, American Association for Cancer Research, United States (2006).

Pallis, M., et al., "The multi-kinase inhibitor TG 02 overcomes signalling activation by survival factors to deplete MCL 1 and XIAP and induce cell death in primary acute myeloid leukaemia cells," *British Journal of Haematology* 159(2): 191-203, Wiley-Blackwell Publishing Ltd., United Kingdom (2012).

Pelton, K., et al., "EXTH-63. Preclinical Efficacy of a CDK Inhibitor (TG02) in Glioblastoma." *Neuro-Oncology*18(suppl_6):vi73, Oxford University Press, United Kingdom (2016).

PR Web, "Tragara and Lee's Pharma Enter into Exclusive Licensing Agreement to Develop and Commercialize TG02 in Greater China Market and South East Asia," press release dated Nov. 16, 2015, 3 pages.

Pasha. M.K et al., "Preclinical Metabolism And Pharmacokinetics of SB1317 (TG02), a Potent CDK/JAK2/FLT3 Inhibitor," *Drug Metabolism Letters* 6(1):33-42, Bentham Science Publishers (2012).

Parrott, T. et al. "P08.32 TG02, an oral CDK inhibitor, demonstrates activity in glioma models: EORTC Brain Tumor Group Conducts Phase 1b study (STEAM / EORTC 1608)" *Neuro-Oncology* 18(Suppl 4): iv48, Oxford University Press (2016).

Wadhwa, E. et al. "PDTM-41. TG02, a Novel Multikinase Inhibitor, is Effective in Pediatric Brain Tumors, With Selective Potency in Those With MYC Expression" *Neuro-Oncology* 19(Suppl 6): vi198-vi199, Oxford University Press (2017).

Sonawane, Y. A. et al. "Cyclin Dependent Kinase 9 Inhibitors for Cancer Therapy," *J. Med. Chem.* 59:8667-8684, American Chemical Society (2016).

Inuzuka, H. et al., "$SCF^{Fbw7}$ Regulates Cellular Apoptosis by Targeting Mcl-1 for Ubiquitination and Destruction," *Nature* 471:104-9, Springer Nature Publishing AG (2011).

Sehgal, A., et al. "PD-1 Checkpoint Blockade in Acute Myeloid Leukemia," *Expert Opin Biol Ther.* 15(8):1191-1203 (2015).

Brahmer, J.R. et al., "Nivolumab: targeting PD-1 to bolster antitumor immunity," *Future Oncology* 11(9):1307-1326, Future Science Group, London, UK (2015).

* cited by examiner

TREATMENT OF CANCER WITH TG02

BACKGROUND OF THE INVENTION

Field of the Invention

The present disclosure provides therapeutic methods of treating a cancer patient with TG02 and a second therapeutic agent, e.g., TG02 and an immune checkpoint inhibitor, TG02 and a COX-2 inhibitor, and TG02 and an immune checkpoint inhibitor and a COX-2 inhibitor.

Background

TG02 is a pyrimidine-based multi-kinase inhibitor that inhibits CDKs 1, 2, 5, 7 and 9 together with JAK2 and FLT3. It dose-dependently inhibits signaling pathways downstream of CDKs, JAK2 and FLT3 in cancer cells with the main targets being CDKs. TG02 is anti-proliferative in a broad range of tumor cell lines, inducing G1 cell cycle arrest and apoptosis. Primary cultures of progenitor cells derived from acute myeloid leukemia (AML) and polycythemia vera patients are very sensitive to TG02. Comparison with reference inhibitors that block only one of the main targets of TG02 demonstrate the benefit of combined CDK and JAK2/FLT3 inhibition in cell lines as well as primary cells. See Goh et al., Leukemia 26:236-43 (2012). TG02 is also known as SB1317 and by its chemical name: (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene. TG02 is disclosed as Compound 1 in U.S. Pat. No. 8,143,255. U.S. Pat. No. 9,120,815 discloses various salt, e.g., TG02 citrate, and crystalline forms of TG02. The chemical structure of TG02 is:

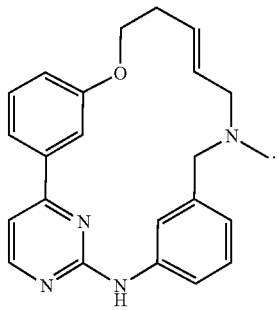 [SMILES: CN1C/C=C/CCOc2cccc(c2)-c2ccnc(n2)Nc2cccc(c2)C1]

BRIEF SUMMARY OF THE INVENTION

In one aspect, the present disclosure provides therapeutic methods of treating a cancer patient, the methods comprising administering to the patient a therapeutically effective amount of TG02. In another aspect, the patient's cancer is characterized as overexpressing of MYC, MCL1, or both.

In another aspect, the present disclosure provides therapeutic methods of treating a cancer patient, the methods comprising administering to the patient therapeutically effective amounts of TG02 and an immune checkpoint inhibitor, e.g., a PD-1 inhibitor, a PD-L1 inhibitor, a CTLA-4 inhibitor, a LAG3 inhibitor, a TIM3 inhibitor, or a cd47 inhibitor.

In another aspect, the present disclosure provides therapeutic methods of treating a cancer patient, the methods comprising administering to the patient therapeutically effective amounts of TG02 and a COX inhibitor, e.g., apricoxib or 6-bromo-8-(methyl-D3)-2-(trifluoromethyl)-2H-chromene-3-carboxylic acid.

In another aspect, the present disclosure provides therapeutic methods of treating a cancer patient, the methods comprising administering to the patient therapeutically effective amounts of TG02, an immune checkpoint inhibitor, and a COX-2 inhibitor.

In another aspect, present disclosure provides therapeutic methods of treating a cancer patient who has tumors that overexpress MYC, MCL1, or both.

In another aspect, the present disclosure provides kits comprising TG02, TG02 and an immune checkpoint inhibitor, TG02 and a COX-2 inhibitor, and TG02 and an immune checkpoint inhibitor and a COX-2 inhibitor.

In another aspect, the present disclosure provides a pharmaceutical composition comprising TG02, a COX-2 inhibitor, e.g., apricoxib or 6-bromo-8-(methyl-D3)-2-(trifluoromethyl)-2H-chromene-3-carboxylic acid and a pharmaceutically acceptable excipient.

DETAILED DESCRIPTION OF THE INVENTION

Figure 1:
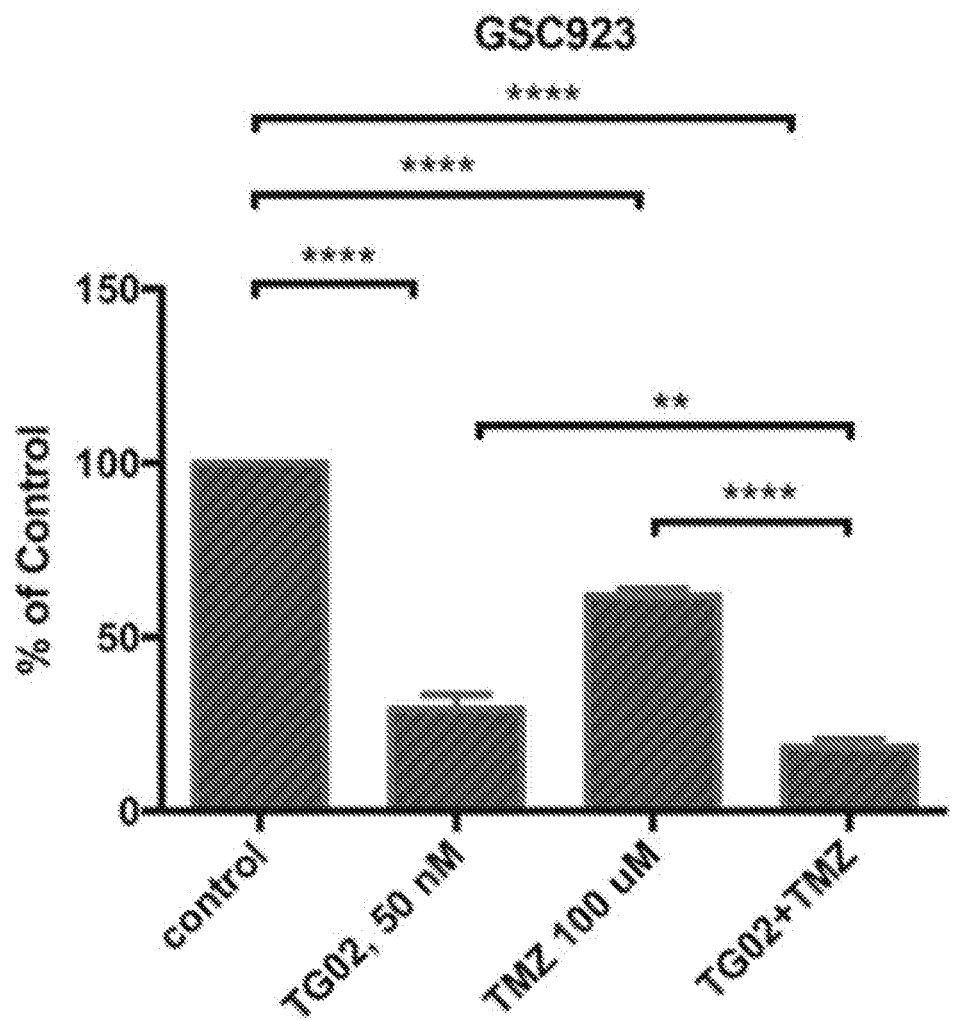
FIG. 1 is a bar graph showing the in vitro activity of TG02, TMZ (temozolomide), and TG02+TMZ in GSC923 cells.

In one embodiment, the present disclosure provides therapeutic methods of treating a patient having cancer, the method comprising administering to the patient a therapeutically effective amount of TG02, wherein one or more of the genes listed in Table 1, see below, is differentially present in a biological sample taken from the patient as compared with a biological sample taken from a subject of another phenotypic status. In another embodiment, MYC overexpression is differentially present in a sample taken from the patient. In another embodiment, MCL1 overexpression is differentially present in a sample taken from the patient.

In another embodiment, the present disclosure provides therapeutic methods of treating a patient having cancer, the method comprising administering to the patient a therapeutically effective amounts of TG02 and an immune checkpoint inhibitor, wherein one or more of the genes listed in Table 1, see below, is differentially present in a biological sample taken from the patient as compared with a biological sample taken from a subject of another phenotypic status. In another embodiment, MYC overexpression is differentially present in a sample taken from the patient. In another embodiment, MCL1 overexpression is differentially present in a sample taken from the patient. In another embodiment, TG02 is administered to the patient before the immune checkpoint inhibitor. In another embodiment, TG02 is administered to the patient after the immune checkpoint inhibitor. In another embodiment, TG02 is administered to the patient at the same time as an immune checkpoint inhibitor.

In another embodiment, the present disclosure provides therapeutic methods of treating a patient having cancer, the method comprising administering to the patient a therapeutically effective amounts of TG02, an immune checkpoint inhibitor, and a COX-2 inhibitor wherein one or more of the genes listed in Table 1, see below, is differentially present in a biological sample taken from the patient as compared with a biological sample taken from a subject of another phenotypic status. In another embodiment, MYC overexpression is differentially present in a sample taken from the patient. In another embodiment, MCL1 overexpression is differentially present in a sample taken from the patient. In another embodiment, TG02 is administered to the patient before the COX-2 inhibitor. In another embodiment, TG02 is administered to the patient after the COX-2 inhibitor. In another embodiment, TG02 is administered to the patient at the same time as the COX-2 inhibitor.

In another embodiment, the present disclosure provides therapeutic methods of treating a patient having cancer, the method comprising administering to the patient therapeutically effective amounts of TG02 and an immune checkpoint inhibitor. In another embodiment, TG02 is administered to the patient before the immune checkpoint inhibitor. In another embodiment, TG02 is administered to the patient after the immune checkpoint inhibitor. In another embodiment, TG02 is administered to the patient at the same time as an immune checkpoint inhibitor.

In another embodiment, the present disclosure provides therapeutic methods of treating a patient having cancer, the method comprising administering to the patient therapeutically effective amounts of TG02, an immune checkpoint inhibitor, and a COX-2 inhibitor. In another embodiment, TG02 is administered to the patient before the COX-2 inhibitor. In another embodiment, TG02 is administered to the patient after the COX-2 inhibitor. In another embodiment, TG02 is administered to the patient at the same time as the COX-2 inhibitor.

In another embodiment, the present disclosure provides kits comprising TG02 and an immune checkpoint inhibitor, and instructions for administering TG02 and the immune checkpoint inhibitor to a patient having cancer. In another embodiment, the kit further comprises a COX-2 inhibitor.

In another embodiment, the present disclosure provides kits comprising TG02 and a COX-2 inhibitor, and instructions for administering TG02 and the COX-2 inhibitor to a patient having cancer.

In another embodiment, the kit is packaged in a manner that facilitates its use to practice methods of the present disclosure.

In another embodiment, the kit includes TG02 (or a composition comprising TG02) packaged in a container, such as a sealed bottle or vessel, with a label affixed to the container or included in the kit that describes use of TG02 or composition to practice the method of the disclosure. In one embodiment, TG02 is packaged in a unit dosage form. The kit further can include a device suitable for administering the composition according to the intended route of administration.

The disclosure provides various therapeutic methods, kits, and compositions relating to the treatment of cancer. In one embodiment, the cancer is a solid tumor. In another embodiment, the cancer is a hematological malignancy. In another embodiment, the cancer selected from the group consisting of adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatocellular carcinoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is selected from the group consisting of squamous cell carcinoma of the head and neck, adenocarcinoma squamous cell carcinoma of the esophagus, adenocarcinoma of the stomach, adenocarcinoma of the colon, hepatocellular carcinoma, cholangiocarcinoma of the biliary system, adenocarcinoma of gall bladder, adenocarcinoma of the pancreas, ductal carcinoma in situ of the breast, adenocarcinoma of the breast, adenocarcinoma of the lungs, squamous cell carcinoma of the lungs, transitional cell carcinoma of the bladder, squamous cell carcinoma of the bladder, squamous cell carcinoma of the cervix, adenocarcinoma of the cervix, endometrial carcinoma, penile squamous cell carcinoma, and squamous cell carcinoma of the skin.

In another embodiment, a precancerous tumor is selected from the group consisting of leukoplakia of the head and neck, Barrett's esophagus, metaplasia of the stomach, adenoma of the colon, chronic hepatitis, bile duct hyperplasia, pancreatic intraepithelial neoplasia, atypical adenomatous hyperplasia of the lungs, dysplasia of the bladder, cervical initraepithelial neoplasia, penile intraepithelial neoplasia, and actinic keratosis of the skin.

In another embodiment, the patient has tumors that overexpress MYC, MCL1, or both. The tumors may be determined to overexpress MYC, MCL1, or both, by methods known in the art.

In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the cancer is selected from the group consisting of glioblastoma, hepatocellular carcinoma, non-small cell and small-cell lung cancer, head and neck cancer, colorectal carcinoma, and triple-negative breast cancer.

In another embodiment, the cancer has become resistant to conventional cancer treatments. The term "conventional cancer treatments" as used herein refers to any cancer drugs or biologics, or combination of cancer drugs and/or biologics that have been tested and/or approved for therapeutic use in humans by the U.S. Food and Drug Administration, European Medicines Agency, or similar regulatory agency.

In another embodiment, the patient has been treated previously with an immune checkpoint inhibitor without TG02. For example, the previous immune checkpoint therapy may be an anti-PD-1 therapy.

In another embodiment, the patient has been treated previously with a COX-2 inhibitor without TG02.

In another embodiment, the present disclosure provides a pharmaceutical composition comprising TG02, a COX-2 inhibitor, and a pharmaceutically acceptable excipient.

In another embodiment, the present disclosure provides therapeutic methods of treating a patient having cancer, the method comprising administering to the patient a therapeutically effective amount of TG02, wherein the phenotypic status of the patient is overexpression of MYC, overexpression of MCL1, or overexpression of MYC and MCL1. In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the present disclosure provides therapeutic methods of treating a patient having cancer, the method comprising administering to the patient therapeutically effective amounts of TG02 and a second therapeutic agent, wherein the second therapeutic agent is neither an immune checkpoint inhibitor nor a COX-2 inhibitor.

In another embodiment, the present disclosure provides therapeutic methods of treating a patient having cancer, comprising administering to the patient therapeutically effective amounts of TG02, an immune checkpoint inhibitor, and a third therapeutic agent, wherein the third therapeutic agent is not a COX-2 inhibitor.

In another embodiment, the present disclosure provides therapeutic methods of treating a patient having cancer, comprising administering to the patient therapeutically effective amounts of TG02, a COX-2 inhibitor, and a third therapeutic agent, wherein the third therapeutic agent is not an immune checkpoint inhibitor.

In another embodiment, the present disclosure provides therapeutic methods of treating a patient having cancer, comprising administering to the patient therapeutically effective amounts of TG02, an immune checkpoint inhibitor, a COX-2 inhibitor, and a fourth therapeutic agent, wherein the fourth therapeutic agent is neither an immune checkpoint inhibitor nor a COX-2 inhibitor.

In another embodiment, the present disclosure provides personalized medicine for cancer patients, and encompasses the selection of treatment options with the highest likelihood of successful outcome for individual cancer patients. In another aspect, the disclosure relates to the use of an assay(s) to predict the treatment outcome, e.g., the likelihood of favorable responses or treatment success, in patients having cancer.

In another embodiment, the present disclosure provides methods of selecting a patient, e.g., a human subject for treatment of cancer with TG02 and, optionally, an immune checkpoint inhibitor and/or a COX-2 inhibitor, comprising obtaining a biological sample, e.g., blood cells, from the patient, testing a biological sample from the patient for the presence of a biomarker, e.g., overexpression of MYC, overexpression of MCL1, or both, and selecting the patient for treatment if the biological sample contains that biomarker. In another embodiment, the methods further comprise administering a therapeutically effective amount of TG02 and, optionally, an immune checkpoint inhibitor and/or a COX-2 inhibitor, to the patient if the biological sample contains the biomarker. Examples of cancer biomarkers are provided in Table 1. In another embodiment, the cancer is a solid tumor. In another embodiment, the cancer is a hematological malignancy. In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the present disclosure provides methods of predicting treatment outcomes in a patient having cancer, comprising obtaining a biological sample from the patient, testing the biological sample from the patient for the presence of a biomarker, e.g., overexpression of MYC, overexpression of MCL1, or both, wherein the detection of the biomarker indicates the patient will respond favorably to administration of a therapeutically effective amount of TG02 and, optionally, an immune checkpoint inhibitor and/or a COX-2 inhibitor. Favorable responses include, but are not limited to, a decrease in tumor size and an increase in progression-free or overall survival.

In another embodiment, the present disclosure provides methods of treating cancer, comprising administering a therapeutically effective amount of TG02 and, optionally, an immune checkpoint inhibitor and/or a COX-2 inhibitor, to a patient, e.g., a human subject, with cancer in whom the patient's cells contain a biomarker. In another embodiment, the patient is selected for treatment with TG02 and, optionally, an immune checkpoint inhibitor and/or a COX-2 inhibitor, after the patient's cells have been determined to contain an overexpression of MYC. In another embodiment, the patient is selected for treatment with TG02 and, optionally, an immune checkpoint inhibitor and/or a COX-2 inhibitor, after the patient's cells have been determined to contain an overexpression of MCL1. In another embodiment, the patient is selected for treatment with TG02 and, optionally, an immune checkpoint inhibitor and/or a COX-2 inhibitor, after the patient's cells have been determined to contain an overexpression of MYC and an overexpression of MCL1.

In another embodiment, the method of treating a patient having cancer comprises obtaining a biological sample from the patient, determining whether the biological sample contains a biomarker, e.g., overexpression of MYC, overexpression of MCL1, or both, and administering to the patient a therapeutically effective amount of TG02 and, optionally, an immune checkpoint inhibitor and/or a COX-2 inhibitor, if the biological sample contains the biomarker. In another embodiment, the methods provided herein comprise determining whether the patient's cells contain an overexpression of MYC. In another embodiment, the methods provided herein comprise determining whether the patient's cells contain an overexpression of MCL1. In another embodiment, the methods provided herein comprise determining whether the patient's cells contain an overexpression of MYC and MCL1.

In another embodiment, the disclosure provides a method of treating a subject having cancer, the method comprising obtaining a biological sample from the subject, determining the expression level of MYC, MCL1, or both in the biological sample; and administering a therapeutically effective amount of TG02 and a second therapeutic agent, e.g., temozolomide, carfilzomib, sorafenib, bortezomib, doxorubicin, cisplatin, lenalidomide, dexamethasone, or Ara-C, to the subject if the biological sample shows overexpression of MYC, MCL1, or both.

In another embodiment, the patient has been treated previously with immune checkpoint inhibitor alone. For example, the previous immune checkpoint therapy may be an anti-PD-1 therapy.

In another embodiment, the patient has been treated previously with COX-2 inhibitor alone.

I. Immune checkpoint inhibitors

Immune checkpoint inhibitors are therapies that blockade immune system inhibitor checkpoints. Immune checkpoints can be stimulatory or inhibitory. Blockade of inhibitory immune checkpoint activates immune system function and can be used for cancer immunotherapy. Pardoll, *Nature*

Reviews. *Cancer* 12:252-64 (2012). Tumor cells turn off activated T cells when they attach to specific T-cell receptors. Immune checkpoint inhibitors prevent tumor cells from attaching to T cells, which results in T cells remaining activated. In effect, the coordinated action by cellular and soluble components combats pathogens and injuries by cancers. The modulation of immune system pathways may involve changing the expression or the functional activity of at least one component of the pathway to then modulate the response by the immune system. U.S. 2015/0250853. Examples of immune checkpoint inhibitors include PD-1 inhibitors, PD-L1 inhibitors, CTLA-4 inhibitors, LAG3 inhibitors, TIM3 inhibitors, cd47 inhibitors, and B7-H1 inhibitors. Thus, in one embodiment, the immune checkpoint inhibitor is selected from the group consisting of a PD-1 inhibitor, a PD-L1 inhibitor, a CTLA-4 inhibitor, a LAG3 inhibitor, a TIM3 inhibitor, and a cd47 inhibitor.

In another embodiment, the immune checkpoint inhibitor is a programmed cell death (PD-1) inhibitor. PD-1 is a T-cell coinhibitory receptor that plays a pivotal role in the ability of tumor cells to evade the host's immune system. Blockage of interactions between PD-1 and PD-L1, a ligand of PD-1, enhances immune function and mediates antitumor activity. Examples of PD-1 inhibitors include antibodies that specifically bind to PD-1. Particular anti-PD-1 antibodies include, but are not limited to nivolumab, pembrolizumab, STI-1014, and pidilzumab. For a general discussion of the availability, methods of production, mechanism of action, and clinical studies of anti-PD-1 antibodies, see U.S. 2013/0309250, U.S. Pat. Nos. 6,808,710, 7,595,048, 8,008,449, 8,728,474, 8,779,105, 8,952,136, 8,900,587, 9,073,994, 9,084,776, and Naido et al., *British Journal of Cancer* 111:2214-19 (2014).

In another embodiment, the immune checkpoint inhibitor is a PD-L1 (also known as B7-H1 or CD274) inhibitor. Examples of PD-L1 inhibitors include antibodies that specifically bind to PD-L1. Particular anti-PD-L1 antibodies include, but are not limited to, avelumab, atezolizumab, durvalumab, and BMS-936559. For a general discussion of the availability, methods of production, mechanism of action, and clinical studies, see U.S. Pat. No. 8,217,149, U.S. 2014/0341917, U.S. 2013/0071403, WO 2015036499, and Naido et al., *British Journal of Cancer* 111:2214-19 (2014).

In another embodiment, the immune checkpoint inhibitor is a CTLA-4 inhibitor. CTLA-4, also known as cytotoxic T-lymphocyte antigen 4, is a protein receptor that down-regulates the immune system. CTLA-4 is characterized as a "brake" that binds costimulatory molecules on antigen-presenting cells, which prevents interaction with CD28 on T cells and also generates an overtly inhibitory signal that constrains T cell activation. Examples of CTLA-4 inhibitors include antibodies that specifically bind to CTLA-4. Particular anti-CTLA-4 antibodies include, but are not limited to, ipilimumab and tremelimumab. For a general discussion of the availability, methods of production, mechanism of action, and clinical studies, see U.S. Pat. Nos. 6,984,720, 6,207,156, and Naido et al., *British Journal of Cancer* 111:2214-19 (2014).

In another embodiment, the immune checkpoint inhibitor is a LAG3 inhibitor. LAG3, Lymphocyte Activation Gene 3, is a negative co-simulatory receptor that modulates T cell homeostatis, proliferation, and activation. In addition, LAG3 has been reported to participate in regulatory T cells (Tregs) suppressive function. A large proportion of LAG3 molecules are retained in the cell close to the microtubule-organizing center, and only induced following antigen specific T cell activation. U.S. 2014/0286935. Examples of LAG3 inhibitors include antibodies that specifically bind to LAG3. Particular anti-LAG3 antibodies include, but are not limited to, GSK2831781. For a general discussion of the availability, methods of production, mechanism of action, and studies, see, U.S. 2011/0150892, U.S. 2014/0093511, U.S. 20150259420, and Huang et al., *Immunity* 21:503-13 (2004).

In another embodiment, the immune checkpoint inhibitor is a TIM3 inhibitor. TIM3, T-cell immunoglobulin and mucin domain 3, is an immune checkpoint receptor that functions to limit the duration and magnitude of $T_H1$ and $T_C1$ T-cell responses. The TIM3 pathway is considered a target for anticancer immunotherapy due to its expression on dysfunctional $CD8^+$ T cells and Tregs, which are two reported immune cell populations that constitute immunosuppression in tumor tissue. Anderson, *Cancer Immunology Research* 2:393-98 (2014). Examples of TIM3 inhibitors include antibodies that specifically bind to TIM3. For a general discussion of the availability, methods of production, mechanism of action, and studies of TIM3 inhibitors, see U.S. 20150225457, U.S. 20130022623, U.S. Pat. No. 8,522,156, Ngiow et al., *Cancer Res* 71: 6567-71 (2011), Ngiow, et al., *Cancer Res* 71:3540-51 (2011), and Anderson, *Cancer Immunology Res* 2:393-98 (2014).

In another embodiment, the immune checkpoint inhibitor is a cd47 inhibitor. See Unanue, E. R., *PNAS* 110:10886-87 (2013).

The term "antibody" is meant to include intact monoclonal antibodies, polyclonal antibodies, multispecific antibodies formed from at least two intact antibodies, and antibody fragments, so long as they exhibit the desired biological activity. In another embodiment, "antibody" is meant to include soluble receptors that do not possess the Fc portion of the antibody. In one embodiment, the antibodies are humanized monoclonal antibodies and fragments thereof made by means of recombinant genetic engineering.

Another class of immune checkpoint inhibitors include polypeptides that bind to and block PD-1 receptors on T-cells without triggering inhibitor signal transduction. Such peptides include B7-DC polypeptides, B7-H1 polypeptides, B7-1 polypeptides and B7-2 polypeptides, and soluble fragments thereof, as disclosed in U.S. Pat. No. 8,114,845.

Another class of immune checkpoint inhibitors include compounds with peptide moieties that inhibit PD-1 signaling. Examples of such compounds are disclosed in U.S. Pat. No. 8,907,053 and have the structure:

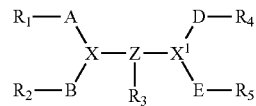

or a pharmaceutically acceptable salt thereof, wherein the compound comprises at least 5 amino acids useful as therapeutic agents capable of inhibiting the PD-1 signaling pathway.

Another class of immune checkpoint inhibitors include inhibitors of certain metabolic enzymes, such as indoleamine 2,3 dioxygenase (IDO), which is expressed by infiltrating myeloid cells and tumor cells. The IDO enzyme inhibits immune responses by depleting amino acids that are necessary for anabolic functions in T cells or through the synthesis of particular natural ligands for cytosolic receptors that are able to alter lymphocyte functions. Pardoll, *Nature Reviews. Cancer* 12:252-64 (2012); Löb, *Cancer Immunol Immunother* 58:153-57 (2009). Particular IDO blocking agents include, but are not limited to levo-1-methyl typtophan (L-1MT) and 1-methyl-tryptophan (1MT). Qian et al., *Cancer Res* 69:5498-504 (2009); and Löb et al., *Cancer Immunol Immunother* 58:153-7 (2009).

In one embodiment, the immune checkpoint inhibitor is nivolumab, pembrolizumab, pidilizumab, STI-1110, avelumab, atezolizumab, durvalumab, STI-1014, ipilimumab, tremelimumab, GSK2831781, BMS-936559 or MED14736.

II. COX-2 Inhibitors

Cyclooxygenase-2 (COX-2) is an enzyme that promotes inflammation and plays a role in tumor progression. COX-2 inhibitors include non-selective inhibitors such as aspirin, ibuprofen, sulindac sulphone, sulindac sulphide, diclofenac, nabumetone, naproxen, indomethacine, and piroxicam, selective inhibitors such as celecoxib, rofecoxib, valdecoxib, ANS-398, Cay10404, SC-236, and DUP697, and preferential inhibitors such as meloxicam and nimesulide. Other COX-2 inhibitors include apricoxib, tilmacoxib, and cimicoxib. Any COX-2 inhibitor is contemplated for use in the therapeutic methods of this disclosure. See Sobolewski et al., "The Role of Cyclooxygenase-2 in Cell Proliferation and Cell Death in Human Malignancies," *International Journal of Cell Biology*, vol. 2010, Article ID 215158, 21 pages, 2010. doi:10.1155/2010/215158.

In another embodiment, the COX-2 inhibitor is apricoxib. See Kirane et al., *Clin. Cancer Res.* 18:5031-5042 (2012).

In another embodiment, the COX-2 inhibitor is selected from the group consisting of:
8-(ethyl-D5)-6-(trifluoromethoxy)-2-(trifluoromethyl)-2H-chromene-3-carboxylic acid;
6-chloro-8-(methyl-D3)-2-(trifluoromethyl)-2H-chromene-3-carb oxylic acid;
6-bromo-8-(methyl-D3)-2-(trifluoromethyl)-2H-chromene-3-carb oxylic acid;
8-chloro-6-(methyl-D3)-2-(trifluoromethyl)-2H-chromene-3-carb oxylic acid;
6,8-dibromo-5,7-(dimethyl-D6)-2-(trifluoromethyl)-2H-chromene-3-carboxylic acid;
8-(1-methylhexyl-D15)-2-(trifluoromethyl)-2H-chromene-3-carboxylic acid;
6-chloro-8-(1-methylhexyl-D15)-2-(trifluoromethyl)-2H-chromene-3-carboxylic acid;
8-(hexyl-D13)-2-(trifluoromethyl)-2H-chromene-3-carboxylic acid;
7,8-(dimethyl-D6)-2-(trifluoromethyl)-2H-chromene-3-carboxylic acid; and
6-chloro-8-(hexyl-D13)-2-(trifluoromethyl)-2H-chromene-3-carboxylic acid.
See US 2015/0133538.

In another embodiment, the COX-2 inhibitor is 6-bromo-8-(methyl-D3)-2-(trifluoromethyl)-2H-chromene-3-carboxylic acid.

III. Optional Therapeutic Agents

In certain therapeutic methods of the disclosure, a second therapeutic agent is administered to a cancer patient in combination with TG02, a third therapeutic agent is administered to a cancer patient in combination with TG02 and an immune checkpoint inhibitor or in combination with TG02 and a COX-2 inhibitor, or a fourth therapeutic agent is administered to a cancer patient in combination with TG02, an immune checkpoint inhibitor, and a COX-2 inhibitor. The second, third and fourth therapeutic agents used in the therapeutic methods of the present disclosure are referred to as "optional therapeutic agents." Such optional therapeutic agents useful in the treatment of cancer patients are known in the art. In one embodiment, the optional therapeutic agent combined with TG02 is an anticancer agent that is neither an immune checkpoint inhibitor nor a COX-2 inhibitor.

Optional therapeutic agents are administered in an amount to provide their desired therapeutic effect. The effective dosage range for each optional therapeutic agent is known in the art, and the optional therapeutic agent is administered to an individual in need thereof within such established ranges.

TG02, the immune checkpoint inhibitor, the COX-2 inhibitor, and/or the optional therapeutic agent can be administered together as a single-unit dose or separately as multi-unit doses, and in any order, e.g., wherein TG02 is administered before the immune checkpoint inhibitor, COX-2 inhibitor, and/or the optional therapeutic agent, or vice versa. One or more doses of TG02, the immune checkpoint inhibitor, the COX-2 inhibitor and/or the optional therapeutic agent can be administered to the patient.

In one embodiment, the optional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, the optional therapeutic agent is a chemotherapeutic agent or other anti-proliferative agent that can be administered in combination with TG02, or a pharmaceutically acceptable salt thereof, to treat cancer. Examples of therapies and anticancer agents that can be used in combination with TG02, or a pharmaceutically acceptable salt thereof, include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Nonlimiting exemplary antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent, e.g., temozolomide; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Nonlimiting exemplary topoisomerase I inhibitors include topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Nonlimiting exemplary alkylating agents include cyclophosphamide, ifosfamide, melphalan, and nitrosoureas, such as carmustine and lomustine.

Nonlimiting exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Nonlimiting exemplary mTOR inhibitors include compounds that inhibit the mammalian target of rapamycin (mTOR) and possess antiproliferative activity such as sirolimus, everolimus, CCI-779, and ABT578.

Nonlimiting exemplary antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Nonlimiting exemplary platin compounds include carboplatin, cis-platin, cisplatinum, and oxaliplatin.

Nonlimiting exemplary methionine aminopeptidase inhibitors include bengamide or a derivative thereof and PPI-2458.

Nonlimiting exemplary bisphosphonates include etridonic acid, clodronic acid, tiludronic acid, pamidronic acid, alendronic acid, ibandronic acid, risedronic acid, and zoledronic acid.

Nonlimiting exemplary heparanase inhibitors include compounds that target, decrease, or inhibit heparin sulfate degradation, such as PI-88 and OGT2115.

Nonlimiting exemplary compounds which target, decrease, or inhibit the oncogenic activity of Ras include farnesyl transferase inhibitors, such as L-744832, DK8G557, tipifarnib, and lonafarnib.

Nonlimiting exemplary telomerase inhibitors include compounds that target, decrease, or inhibit the activity of telomerase, such as compounds that inhibit the telomerase receptor, such as telomestatin.

Nonlimiting exemplary proteasome inhibitors include compounds that target, decrease, or inhibit the activity of the proteasome including, but not limited to, bortezomib. In some embodiments, the proteasome inhibitor is carfilzomib.

Nonlimiting exemplary FMS-like tyrosine kinase inhibitors, which are compounds targeting, decreasing or inhibiting the activity of FMS-like tyrosine kinase receptors (Flt-3R) include interferon, I-β-D-arabinofuransylcytosine (arac), and bisulfan; and ALK inhibitors, which are compounds which target, decrease, or inhibit anaplastic lymphoma kinase.

Nonlimiting exemplary Flt-3 inhibitors include PKC412, midostaurin, a staurosporine derivative, SU11248, and MLN518.

Nonlimiting exemplary HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

Nonlimiting exemplary protein tyrosine kinase and/or serine and/or threonine kinase inhibitors or lipid kinase inhibitors, include a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, C1-1033, EKB- 569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Nonlimiting exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with TG02, or a pharmaceutically acceptable salt thereof, include: avastin, daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

A number of suitable optional therapeutic, e.g., anticancer, agents are contemplated for use in the therapeutic methods provided herein. Indeed, the methods provided herein can include, but are not limited to, administration of numerous optional therapeutic agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of optional therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the therapeutic methods provided herein include administering to a cancer patient a therapeutically effective amount of TG02 and at least one additional anti-hyperproliferative or antineoplastic agent selected from alkylating agents, antimetabolites, and natural products (e.g., herbs and other plant and/or animal derived compounds).

Alkylating agents suitable for use in the present methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimidazolecarboxamide).

In some embodiments, antimetabolites suitable for use in the present methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the methods of the present disclosure include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the therapeutic methods of the present disclosure. For example, the U.S. Food and Drug Administration (FDA) maintains a formulary of oncolytic agents approved for use in the United States. International counterpart agencies to the FDA maintain similar formularies. Those skilled in the art will appreciate that the "product labels" required on all U.S. approved chemotherapeutics describe approved indications, dosing information, toxicity data, and the like, for the exemplary agents.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other optional therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments, methods provided herein comprise administering TG02 to a cancer patient in combination with radiation therapy. The methods provided herein are not limited by the types, amounts, or delivery and administration systems used to deliver the therapeutic dose of radiation to a patient. For example, the patient may receive photon radiotherapy, particle beam radiation therapy, other types of radiotherapies, and combinations thereof. In some embodiments, the radiation is delivered to the patient using a linear accelerator. In still other embodiments, the radiation is delivered using a gamma knife.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The patient may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to a patient is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

IV. Therapeutic Methods

In the therapeutic methods provided herein, TG02, the immune checkpoint inhibitor, the COX-2 inhibitor, and/or the optional therapeutic, e.g., anticancer, agent may be administered to a cancer patient under one or more of the following conditions: at different periodicities, at different durations, at different concentrations, by different administration routes, etc.

In some embodiments, TG02 is administered prior to the immune checkpoint inhibitor, the COX-2 inhibitor, and/or the optional therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the immune checkpoint inhibitor, the COX-2 inhibitor, and/or the optional therapeutic agent.

In some embodiments, TG02 is administered after the immune checkpoint inhibitor, the COX-2 inhibitor, and/or the optional therapeutic agent, e.g., 0.5, 1, 2, 3, 4, 5, 10, 12, or 18 hours, 1, 2, 3, 4, 5, or 6 days, or 1, 2, 3, or 4 weeks after the administration of the immune checkpoint inhibitor, the COX-2 inhibitor, and/or the optional therapeutic agent.

In some embodiments, TG02, the immune checkpoint inhibitor, the COX-2 inhibitor, and/or the optional therapeutic agent are administered concurrently but on different schedules, e.g., TG02 is administered daily while the immune checkpoint inhibitor is administered once a week, once every two weeks, once every three weeks, or once every four weeks. In other embodiments, TG02 is administered once a day while the immune checkpoint inhibitor, the COX-2 inhibitor, and/or the optional therapeutic agent is administered once a week, once every two weeks, once every three weeks, or once every four weeks.

The therapeutic methods provided herein comprise administering TG02 to a cancer patient in an amount which is effective to achieve its intended purpose. While individual needs vary, determination of optimal ranges of effective amounts of each component is within the skill of the art. Typically, TG02 may be administered in an amount from about 1 mg/kg to about 500 mg/kg, about 1 mg/kg to about 100 mg/kg, or about 1 mg/kg to about 50 mg/kg. The dosage of a composition can be at any dosage including, but not limited to, 30-600 mg/day. Particular doses include 50, 100, 200, 250, 300, 400, 500, and 600 mg/day. In one embodiment, TG02 is administered once a day on 3-7 consecutive days prior to the administration of the immune checkpoint inhibitor. In another embodiment, 250 mg/day of TG02 is administered. In another embodiment, 250 mg/day of TG02 is administered twice weekly. In another embodiment, TG02 administration continues on the day of the immune checkpoint inhibitor and continues for additional days until disease progression or until TG02 administration is no longer beneficial. These dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

The unit oral dose of TG02 may comprise from about 0.01 to about 1000 mg, e.g., about 10 to about 500 mg of TG02. In one embodiment, the unit oral dose of TG02 is 10 mg, 20 mg, 30 mg, 40 mg, 50 mg, 60 mg, 70 mg 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, or 300 mg. The unit dose may be administered one or more times daily, e.g., as one or more tablets or capsules.

In addition to administering TG02 as a raw chemical, it may be administered as part of a pharmaceutical preparation or composition. In some embodiments, the pharmaceutical preparation or composition can include one or more pharmaceutically acceptable carriers, excipients, and/or auxiliaries. In some embodiments, the one or more carriers, excipients, and auxiliaries facilitate processing of TG02 into a preparation or composition which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the one or more carriers, excipients, and/or auxiliaries.

The pharmaceutical compositions of provided herein may be administered to any patient which may experience the beneficial effects of TG02. Foremost among such patients are mammals, e.g., humans, although the methods and compositions provided herein are not intended to be so limited. Other patients include veterinary animals (cows, sheep, pigs, horses, dogs, cats and the like).

The pharmaceutical preparations provided herein are manufactured by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension including, for example, sodium carboxymethyl cellulose, sorbitol, and/or dextran. Optionally, the suspension may also contain stabilizers.

The present disclosure encompasses the use of solvates of TG02. Solvates typically do not significantly alter the physiological activity or toxicity of a compound, and as such may function as pharmacological equivalents. The term "solvate" as used herein is a combination, physical association and/or solvation of TG02 with a solvent molecule such as, e.g. a disolvate, monosolvate or hemisolvate, where the ratio of solvent molecule to TG02 is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. TG02 can be present as solvated forms with a pharmaceutically acceptable solvent, such as water, methanol, ethanol, and the like, and it is intended that the disclosure includes both solvated and unsolvated forms of TG02. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate involves dissolving TG02 in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Therapeutically effective amounts of TG02 and/or the immune checkpoint inhibitor, and/or the COX-2 inhibitor, and/or the optional therapeutic agent formulated in accordance with standard pharmaceutical practices, are administered to a human patient in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

TG02, the immune checkpoint inhibitor, the COX-2 inhibitor, and/or the optional therapeutic agent can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein TG02, the immune checkpoint inhibitor, the COX-2 inhibitor, and/or the optional therapeutic agent are administered in an effective amount to achieve its intended purpose. The exact formulation, route of administration, and dosage is determined by an individual physician in view of the diagnosed condition or disease. Dosage amount and interval can be adjusted individually to provide levels of TG02, immune checkpoint inhibitor, COX-2 inhibitor, and/or optional therapeutic agent that is sufficient to maintain therapeutic effects.

Toxicity and therapeutic efficacy of TG02, the immune checkpoint inhibitor, the COX-2 inhibitor, and/or the optional therapeutic agent can be determined by standard pharmaceutical procedures in cell cultures or experimental animals, e.g., for determining the maximum tolerated dose (MTD) of a compound, which defines as the highest dose that causes no toxicity in a patient. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of TG02, immune checkpoint inhibitor, COX-2 inhibitor, and/or optional therapeutic agent required for use in therapy varies with the nature of the condition being treated, the length of time that activity is desired, and the age and the condition of the patient, and ultimately is determined by the attendant physician. For example, dosage amounts and intervals can be adjusted individually to provide plasma levels of TG02 and immune checkpoint inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, TG02 and immune checkpoint inhibitor can be administered at a frequency of: one dose per day; four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The immune checkpoint inhibitor is administered in therapeutically effective amounts. When the immune checkpoint inhibitor is a monoclonal antibody, 1-20 mg/kg is administered as an intravenous infusion every 2-4 weeks. For example, 50 mg, 60 mg, 70 mg, 80 mg, 90 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg and 2000 mg of the antibody may be administered.

For example, when the immune checkpoint inhibitor is the anti-PD-1 antibody nivolumab, 3 mg/kg may be administered by intravenous infusion over 60 minutes every two weeks. When the immune checkpoint inhibitor is the anti-PD-1 antibody pembrolizumab, 2 mg/kg may be administered by intravenous infusion over 30 minutes every two or three weeks. When the immune checkpoint inhibitor is the anti-PD-L1 antibody avelumab, 10 mg/kg may be administered by intravenous infusion as frequently as every 2 weeks. Disis et al., *J. Clin Oncol.* 33 (2015) (suppl; abstr 5509). When the immune checkpoint inhibitor is the anti-PD-L1 antibody MPDL3280A, 20 mg/kg may be administered by intravenous infusion every 3 weeks. Herbst et al., *Nature* 515:563-80 (2014). When the immune checkpoint inhibitor is the anti-CTLA-4 antibody ipilumumab, 3 mg/kg may be administered by intravenous infusion over 90 minutes every 3 weeks. When the immune checkpoint inhibitor is the anti-CTLA-4 antibody tremelimumab, 15 mg/kg may be administered by intravenous infusion every 12 weeks. Naido et al., *British Journal of Cancer* 111:2214-19 (2014); Drugs R D, 10:123-32 (2010). When the immune checkpoint inhibitor is the anti-LAG3 antibody GSK2831781, 1.5 to 5 mg/kg may be administered by intravenous infusion over 120 minutes every 2-4 weeks. When the immune checkpoint inhibitor is an anti-TIM3 antibody, 1-5 mg/kg may be administered by intravenous infusion over 30-90 minutes every 2-4 weeks. When an inhibitor of indoleamine 2,3-dioxygenase (IDO) pathway is inhibitor indoximod in combination with temozolomide, 18.5 mg/kg/dose BID with an escalation to 27.7 mg/kg/dose BID of indoximod with 200 mg/m$^2$ every 5 days of temozolomide.

The COX-2 inhibitor is also administered in therapeutically effective amounts, e.g., from about 1 mg/kg to about 500 mg/kg, about 1 mg/kg to about 100 mg/kg, or about 1 mg/kg to about 50 mg/kg. The unit oral dose of the COX-2 inhibitor may comprise from about 0.01 to about 1000 mg, e.g., about 1 to about 250 mg of the COX-2 inhibitor. In one embodiment, the unit oral dose of the COX-2 inhibitor is 5 mg, 10 mg, 20 mg, 30 mg, 40 mg, 50 mg, 60 mg, 70 mg 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg. The unit dose may be administered one or more times daily, e.g., as one or more tablets or capsules.

In one embodiment, the immune checkpoint inhibitor is an antibody and 1-20 mg/kg is administered by intravenous infusion every 2-4 weeks. In another embodiment, 50-2000 mg of the antibody is administered by intravenous infusion every 2-4 weeks. In another embodiment, TG02 is administered prior to administration of the antibody. In another embodiment, TG02 is administered 3-7 days prior to the day of administration of the antibody. In another embodiment, TG02 is also administered the day the antibody is administered and on consecutive days thereafter until disease progression or until TG02 administration is no longer beneficial.

In one embodiment, the cancer patient has tumors with a biomarker, e.g., overexpression of MYC and/or MCL1, and receives 2 mg/kg pembrolizumab administered by intravenous infusion every three weeks and 30-600 mg of TG02 administered for 3-7 days prior to pembrolizumab administration, on the day of pembrolizumab administration, and thereafter until disease progression or until there is no therapeutic benefit.

In another embodiment, the cancer patient has tumors with a biomarker, e.g., overexpression of MYC and/or MCL1, and receives 3 mg/kg nivolumab administered by intravenous infusion every 2 weeks and 30-600 mg TG02 administered orally for 3-7 days prior to nivolumab administration, on the day of nivolumab administration, and thereafter until disease progression or until there is no therapeutic benefit.

In another embodiment, the cancer patient has tumors with a biomarker, e.g., overexpression of MYC and/or MCL1, and receives 3 mg/kg nivolumab administered by intravenous infusion every 2 weeks and 30-600 mg TG02 administered orally twice weekly prior to nivolumab administration, on the day of nivolumab administration, and thereafter until disease progression or until there is no therapeutic benefit.

In another embodiment, the treatment of the cancer patient with an immune checkpoint inhibitor and TG02 induces anti-proliferative response faster than when the immune checkpoint inhibitor is administered alone.

In another embodiment, the treatment of the cancer patient with a COX-2 inhibitor and TG02 induces antiproliferative response faster than when the COX-2 inhibitor is administered alone.

V. Biomarkers

The term "biomarker" as used herein refers to any biological compound, such as a gene, a protein, a fragment of a protein, a peptide, a polypeptide, a nucleic acid, etc., that can be detected and/or quantified in a cancer patient in vivo or in a biological sample obtained from a cancer patient. A biomarker can be the entire intact molecule, or it can be a portion or fragment thereof. In one embodiment, the expression level of the biomarker is measured. The expression level of the biomarker can be measured, for example, by detecting the protein or RNA, e.g., mRNA, level of the biomarker. In some embodiments, portions or fragments of biomarkers can be detected or measured, for example, by an antibody or other specific binding agent. In some embodiments, a measurable aspect of the biomarker is associated with a given state of the patient, such as a particular stage of cancer. For biomarkers that are detected at the protein or RNA level, such measurable aspects may include, for example, the presence, absence, or concentration, i.e., expression level, of the biomarker in a cancer patient, or biological sample obtained from the cancer patient. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes.

Biomarkers include, but are not limited, the genes listed in Table 1. In one embodiment, the measurable aspect of the biomarker is its expression status. In one embodiment, the measurable aspect of the biomarker is its mutation status.

TABLE 1

| Gene | Gene synonym | Gene description |
| --- | --- | --- |
| A2M | CPAMD5, FWP007, S863-7 | Alpha-2-macroglobulin |
| ABCB1 | ABC20, CD243, CLCS, GP170, MDR1, P-gp, PGY1 | ATP-binding cassette, sub-family B (MDR/TAP), member 1 |
| ABCC1 | GS-X, MRP, MRP1 | ATP-binding cassette, sub-family C (CFTR/MRP), member 1 |
| ABCC2 | CMOAT, cMRP, DJS, MRP2 | ATP-binding cassette, sub-family C (CFTR/MRP), member 2 |
| ABCC3 | cMOAT2, EST90757, MLP2, MOAT-D, MRP3 | ATP-binding cassette, sub-family C (CFTR/MRP), member 3 |
| ABCC5 | EST277145, MOAT-C, MRP5, SMRP | ATP-binding cassette, sub-family C (CFTR/MRP), member 5 |
| ABCC6 | ARA, EST349056, MLP1, MRP6, PXE, URG7 | ATP-binding cassette, sub-family C (CFTR/MRP), member 6 |
| ABCG2 | ABCP, BCRP, CD338, EST157481, MXR | ATP-binding cassette, sub-family G (WHITE), member 2 (Junior blood group) |
| ABL1 | ABL, c-ABL, JTK7, p150 | ABL proto-oncogene 1, non-receptor tyrosine kinase |
| ABL2 | ABLL, ARG | ABL proto-oncogene 2, non-receptor tyrosine kinase |
| ACAP1 | CENTB1, KIAA0050 | ArfGAP with coiled-coil, ankyrin repeat and PH domains 1 |
| ACLY | ACL, ATPCL, CLATP | ATP citrate lyase |
| ACPP | ACP-3, ACP3 | Acid phosphatase, prostate |
| ACVR1B | ActRIB, ACVRLK4, ALK4, SKR2 | Activin A receptor, type IB |
| ACVR2A | ACTRII, ACVR2 | Activin A receptor, type IIA |
| ACVR2B | ActR-IIB | Activin A receptor, type IIB |
| ADAM9 | CORD9, KIAA0021, MCMP, MDC9, Mltng | ADAM metallopeptidase domain 9 |
| ADAMTS1 | C3-C5, KIAA1346, METH1 | ADAM metallopeptidase with thrombospondin type 1 motif, 1 |
| ADAMTS14 | | ADAM metallopeptidase with thrombospondin type 1 motif, 14 |
| ADAMTS18 | ADAMTS21 | ADAM metallopeptidase with thrombospondin type 1 motif, 18 |
| ADAMTS20 | GON-1 | ADAM metallopeptidase with thrombospondin type 1 motif, 20 |
| ADAMTS3 | ADAMTS-4, KIAA0366 | ADAM metallopeptidase with thrombospondin type 1 motif, 3 |
| ADAMTS4 | ADAMTS-2, ADMP-1, KIAA0688 | ADAM metallopeptidase with thrombospondin type 1 motif, 4 |
| ADAMTS5 | ADAMTS11, ADMP-2 | ADAM metallopeptidase with thrombospondin type 1 motif, 5 |
| ADAMTS6 | ADAM-TS6 | ADAM metallopeptidase with thrombospondin type 1 motif, 6 |

TABLE 1-continued

| Gene | Gene synonym | Gene description |
|---|---|---|
| ADAMTS8 | ADAM-TS8, FLJ41712, METH2 | ADAM metallopeptidase with thrombospondin type 1 motif, 8 |
| ADAMTS9 | KIAA1312 | ADAM metallopeptidase with thrombospondin type 1 motif, 9 |
| ADM | AM | Adrenomedullin |
| ADRA1B | | Adrenoceptor alpha 1B |
| AFP | FETA, HPAFP | Alpha-fetoprotein |
| AGER | RAGE | Advanced glycosylation end product-specific receptor |
| AHR | bHLHe76 | Aryl hydrocarbon receptor |
| AHSG | A2HS, FETUA, HSGA | Alpha-2-HS-glycoprotein |
| AKAP12 | AKAP250, SSeCKS | A kinase (PRKA) anchor protein 12 |
| AKR1B1 | ALDR1, AR | Aldo-keto reductase family 1, member B1 (aldose reductase) |
| AKT1 | AKT, PKB, PRKBA, RAC | V-akt murine thymoma viral oncogene homolog 1 |
| AKT2 | | V-akt murine thymoma viral oncogene homolog 2 |
| AKT3 | PKBG, PRKBG, RAC-gamma | V-akt murine thymoma viral oncogene homolog 3 |
| ALB | | Albumin |
| ALCAM | CD166, MEMD | Activated leukocyte cell adhesion molecule |
| ALDOA | | Aldolase A, fructose-bisphosphate |
| ALDOB | | Aldolase B, fructose-bisphosphate |
| ALDOC | | Aldolase C, fructose-bisphosphate |
| ALPL | HOPS, TNSALP | Alkaline phosphatase, liver/bone/kidney |
| ALPP | | Alkaline phosphatase, placental |
| ANG | RNASE5 | Angiogenin, ribonuclease, RNase A family, 5 |
| ANGPT1 | Ang1, KIAA0003 | Angiopoietin 1 |
| ANGPT2 | Ang2 | Angiopoietin 2 |
| ANXA1 | ANX1, LPC1 | Annexin A1 |
| ANXA11 | ANX11 | Annexin A11 |
| ANXA2 | ANX2, ANX2L4, CAL1H, LIP2, LPC2D | Annexin A2 |
| ANXA4 | ANX4 | Annexin A4 |
| ANXA7 | ANX7 | Annexin A7 |
| AOC3 | HPAO, VAP-1, VAP1 | Amine oxidase, copper containing 3 |
| AP2B1 | ADTB2, CLAPB1 | Adaptor-related protein complex 2, beta 1 subunit |
| APAF1 | APAF-1, CED4 | Apoptotic peptidase activating factor 1 |
| APEX1 | APE, APE-1, APEN, APEX, APX, HAP1, REF-1, REF1 | APEX nuclease (multifunctional DNA repair enzyme) 1 |
| APOA1 | | Apolipoprotein A-I |
| APOA2 | | Apolipoprotein A-II |
| APOC1 | | Apolipoprotein C-I |
| APOC3 | | Apolipoprotein C-III |
| APOD | | Apolipoprotein D |
| APOE | AD2 | Apolipoprotein E |
| APPBP2 | Hs.84084, KIAA0228, PAT1 | Amyloid beta precursor protein (cytoplasmic tail) binding protein 2 |
| AR | AIS, DHTR, HUMARA, NR3C4, SBMA, SMAX1 | Androgen receptor |
| AREG | AREGB, SDGF | Amphiregulin |
| ARG2 | | Arginase 2 |
| ARNT | bHLHe2, HIF-1beta | Aryl hydrocarbon receptor nuclear translocator |
| ASPH | BAH, CASQ2BP1, HAAH, JCTN | Aspartate beta-hydroxylase |
| ATM | ATA, ATC, ATD, ATDC, TEL1, TELO1 | ATM serine/threonine kinase |
| ATOH1 | bHLHa14, HATH1, MATH-1, Math1 | Atonal homolog 1 (*Drosophila*) |
| ATP7B | WND | ATPase, Cu++ transporting, beta polypeptide |
| AURKA | AIK, ARK1, AurA, BTAK, PPP1R47, STK15, STK6, STK7 | Aurora kinase A |
| AURKB | Aik2, AIM-1, ARK2, AurB, IPL1, PPP1R48, STK12, STK5 | Aurora kinase B |
| AZGP1 | ZA2G, ZAG | Alpha-2-glycoprotein 1, zinc-binding |
| B2M | | Beta-2-microglobulin |
| BAD | BBC2, BCL2L8 | BCL2-associated agonist of cell death |
| BAG1 | | BCL2-associated athanogene |
| BAI1 | | Brain-specific angiogenesis inhibitor 1 |

TABLE 1-continued

| Gene | Gene synonym | Gene description |
|---|---|---|
| BAX | BCL2L4 | BCL2-associated X protein |
| BCL11A | BCL11A-L, BCL11A-S, BCL11A-XL, CTIP1, EVI9, HBFQTL5, ZNF856 | B-cell CLL/lymphoma 11A (zinc finger protein) |
| BCL2 | Bcl-2, PPP1R50 | B-cell CLL/lymphoma 2 |
| BCL2A1 | ACC-1, ACC-2, BCL2L5, BFL1, GRS, HBPA1 | BCL2-related protein A1 |
| BCL2L1 | Bcl-X, bcl-xL, bcl-xS, BCL2L, BCLX, PPP1R52 | BCL2-like 1 |
| BCL2L2 | BCL-W, KIAA0271, PPP1R51 | BCL2-like 2 |
| BCL2L2-PABPN1 | | BCL2L2-PABPN1 readthrough |
| BCL3 | BCL4, D19S37 | B-cell CLL/lymphoma 3 |
| BCL6 | BCL5, BCL6A, LAZ3, ZBTB27, ZNF51 | B-cell CLL/lymphoma 6 |
| BDNF | | Brain-derived neurotrophic factor |
| BIRC2 | API1, c-IAP1, cIAP1, hiap-2, MIHB, RNF48 | Baculoviral IAP repeat containing 2 |
| BIRC3 | API2, c-IAP2, cIAP2, hiap-1, MALT2, MIHC, RNF49 | Baculoviral IAP repeat containing 3 |
| BIRC5 | API4, EPR-1, survivin | Baculoviral IAP repeat containing 5 |
| BIRC6 | BRUCE | Baculoviral IAP repeat containing 6 |
| BLK | MGC10442 | BLK proto-oncogene, Src family tyrosine kinase |
| BLMH | BH | Bleomycin hydrolase |
| BMI1 | PCGF4, RNF51 | BMI1 proto-oncogene, polycomb ring finger |
| BMP2 | BMP2A | Bone morphogenetic protein 2 |
| BMP4 | BMP2B | Bone morphogenetic protein 4 |
| BNIP3 | Nip3 | BCL2/adenovirus E1B 19 kDa interacting protein 3 |
| BNIP3L | BNIP3a, Nix | BCL2/adenovirus E1B 19 kDa interacting protein 3-like |
| BRCA1 | BRCC1, PPP1R53, RNF53 | Breast cancer 1, early onset |
| BRCA2 | BRCC2, FACD, FAD, FAD1, FANCD, FANCD1 | Breast cancer 2, early onset |
| BRMS1 | DKFZP564A063 | Breast cancer metastasis suppressor 1 |
| BTG2 | MGC126063, MGC126064, PC3, TIS21 | BTG family, member 2 |
| C18orf8 | HsT2591, MIC-1, MIC1 | Chromosome 18 open reading frame 8 |
| C1QBP | gC1Q-R, gC1qR, HABP1, p32, SF2p32 | Complement component 1, q subcomponent binding protein |
| C6 | | Complement component 6 |
| C7 | | Complement component 7 |
| CA8 | CALS, CARP | Carbonic anhydrase VIII |
| CALCA | CALC1 | Calcitonin-related polypeptide alpha |
| CALM1 | CALML2, CAMI, DD132, PHKD | Calmodulin 1 (phosphorylase kinase, delta) |
| CALM2 | CAMII, PHKD | Calmodulin 2 (phosphorylase kinase, delta) |
| CALM3 | PHKD | Calmodulin 3 (phosphorylase kinase, delta) |
| CALR | cC1qR, CRT, FLJ26680, RO, SSA | Calreticulin |
| CANX | CNX, IP90, P90 | Calnexin |
| CAPN6 | CalpM, CANPX, CAPNX | Calpain 6 |
| CASC3 | BTZ, MLN51 | Cancer susceptibility candidate 3 |
| CASP1 | ICE, IL1BC | Caspase 1, apoptosis-related cysteine peptidase |
| CASP10 | MCH4 | Caspase 10, apoptosis-related cysteine peptidase |
| CASP2 | ICH1, MGC2181, NEDD2, PPP1R57 | Caspase 2, apoptosis-related cysteine peptidase |
| CASP3 | apopain, CPP32, CPP32B, Yama | Caspase 3, apoptosis-related cysteine peptidase |
| CASP4 | ICE(rel)II, ICH-2, TX | Caspase 4, apoptosis-related cysteine peptidase |
| CASP5 | ICE(rel)III | Caspase 5, apoptosis-related cysteine peptidase |
| CASP6 | MCH2 | Caspase 6, apoptosis-related cysteine peptidase |
| CASP7 | CMH-1, ICE-LAP3, MCH3 | Caspase 7, apoptosis-related cysteine peptidase |
| CASP8 | Casp-8, FLICE, MACH, MCH5 | Caspase 8, apoptosis-related cysteine peptidase |
| CASP9 | APAF-3, ICE-LAP6, MCH6, PPP1R56 | Caspase 9, apoptosis-related cysteine peptidase |

TABLE 1-continued

| Gene | Gene synonym | Gene description |
|---|---|---|
| CAT | | Catalase |
| CAV1 | CAV | Caveolin 1, caveolae protein, 22 kDa |
| CBL | c-Cbl, CBL2, RNF55 | Cbl proto-oncogene, E3 ubiquitin protein ligase |
| CCKBR | | Cholecystokinin B receptor |
| CCL11 | eotaxin, MGC22554, SCYA11 | Chemokine (C-C motif) ligand 11 |
| CCL13 | CKb10, MCP-4, MGC17134, NCC-1, SCYA13, SCYL1 | Chemokine (C-C motif) ligand 13 |
| CCL14 | CKb1, HCC-1, HCC-3, MCIF, NCC-2, SCYA14, SCYL2 | Chemokine (C-C motif) ligand 14 |
| CCL16 | CKb12, HCC-4, LCC-1, LEC, LMC, Mtn-1, NCC-4, SCYA16, SCYL4 | Chemokine (C-C motif) ligand 16 |
| CCL18 | AMAC-1, CKb7, DC-CK1, DCCK1, MIP-4, PARC, SCYA18 | Chemokine (C-C motif) ligand 18 (pulmonary and activation-regulated) |
| CCL19 | CKb11, ELC, exodus-3, MIP-3b, SCYA19 | Chemokine (C-C motif) ligand 19 |
| CCL2 | GDCF-2, HC11, MCAF, MCP-1, MCP1, MGC9434, SCYA2, SMC-CF | Chemokine (C-C motif) ligand 2 |
| CCL21 | 6Ckine, CKb9, ECL, exodus-2, SCYA21, SLC, TCA4 | Chemokine (C-C motif) ligand 21 |
| CCL23 | Ckb-8, CKb8, MIP-3, MPIF-1, SCYA23 | Chemokine (C-C motif) ligand 23 |
| CCL3 | G0S19-1, LD78ALPHA, MIP-1-alpha, SCYA3 | Chemokine (C-C motif) ligand 3 |
| CCL4 | Act-2, AT744.1, LAG1, MIP-1-beta, SCYA4 | Chemokine (C-C motif) ligand 4 |
| CCL5 | D17S136E, MGC17164, RANTES, SCYA5, SISd, TCP228 | Chemokine (C-C motif) ligand 5 |
| CCL7 | FIC, MARC, MCP-3, MCP3, NC28, SCYA6, SCYA7 | Chemokine (C-C motif) ligand 7 |
| CCL8 | HC14, MCP-2, SCYA8 | Chemokine (C-C motif) ligand 8 |
| CCNA1 | CT146 | Cyclin A1 |
| CCNA2 | CCN1, CCNA | Cyclin A2 |
| CCNB1 | CCNB | Cyclin B1 |
| CCNB2 | HsT17299 | Cyclin B2 |
| CCND1 | BCL1, D11S287E, PRAD1, U21B31 | Cyclin D1 |
| CCND2 | | Cyclin D2 |
| CCNE1 | CCNE | Cyclin E1 |
| CCNE2 | CYCE2 | Cyclin E2 |
| CCNG1 | CCNG | Cyclin G1 |
| CCNG2 | | Cyclin G2 |
| CCNH | CycH, p34, p37 | Cyclin H |
| CCR10 | GPR2 | Chemokine (C-C motif) receptor 10 |
| CCR7 | BLR2, CD197, CDw197, CMKBR7, EBI1 | Chemokine (C-C motif) receptor 7 |
| CD14 | | CD14 molecule |
| CD27 | S152, TNFRSF7, Tp55 | CD27 molecule |
| CD36 | FAT, GP3B, GP4, GPIV, SCARB3 | CD36 molecule (thrombospondin receptor) |
| CD38 | | CD38 molecule |
| CD40 | Bp50, p50, TNFRSF5 | CD40 molecule, TNF receptor superfamily member 5 |
| CD40LG | CD154, CD40L, gp39, hCD40L, HIGM1, IMD3, TNFSF5, TRAP | CD40 ligand |
| CD44 | CD44R, CSPG8, HCELL, IN, MC56, MDU2, MDU3, MIC4, Pgp1 | CD44 molecule (Indian blood group) |
| CD46 | MCP, MGC26544, MIC10, TLX, TRA2.10 | CD46 molecule, complement regulatory protein |
| CD52 | CDW52 | CD52 molecule |
| CD59 | 16.3A5, EJ16, EJ30, EL32, G344, MIC11, MIN1, MIN2, MIN3, MSK21, p18-20 | CD59 molecule, complement regulatory protein |

TABLE 1-continued

| Gene | Gene synonym | Gene description |
|---|---|---|
| CD70 | CD27L, CD27LG, TNFSF7 | CD70 molecule |
| CD74 | DHLAG | CD74 molecule, major histocompatibility complex, class II invariant chain |
| CD82 | IA4, KAI1, R2, ST6, TSPAN27 | CD82 molecule |
| CD9 | BA2, MIC3, MRP-1, P24, TSPAN29 | CD9 molecule |
| CDC16 | ANAPC6, APC6, CUT9 | Cell division cycle 16 |
| CDC20 | CDC20A, p55CDC | Cell division cycle 20 |
| CDC25A | | Cell division cycle 25A |
| CDC25B | | Cell division cycle 25B |
| CDC25C | CDC25, PPP1R60 | Cell division cycle 25C |
| CDC34 | E2-CDC34, UBC3, UBE2R1 | Cell division cycle 34 |
| CDC37 | P50CDC37 | Cell division cycle 37 |
| CDC6 | CDC18L | Cell division cycle 6 |
| CDH1 | CD324, UVO, uvomorulin | Cadherin 1, type 1, E-cadherin (epithelial) |
| CDH17 | cadherin, HPT-1 | Cadherin 17, LI cadherin (liver-intestine) |
| CDH5 | 7B4, CD144 | Cadherin 5, type 2 (vascular endothelium) |
| CDK1 | CDC2, CDC28A | Cyclin-dependent kinase 1 |
| CDK2 | | Cyclin-dependent kinase 2 |
| CDK4 | PSK-J3 | Cyclin-dependent kinase 4 |
| CDK6 | PLSTIRE | Cyclin-dependent kinase 6 |
| CDK7 | CAR, CAK1, CDKN7, MO15, STK1 | Cyclin-dependent kinase 7 |
| CDKN1A | CAP20, CDKN1, CIP1, P21, p21CIP1, p21Cip1/Waf1, SDI1, WAF1 | Cyclin-dependent kinase inhibitor 1A (p21, Cip1) |
| CDKN1C | BWCR, BWS, KIP2, P57 | Cyclin-dependent kinase inhibitor 1C (p57, Kip2) |
| CDKN2A | ARF, CDK4I, CDKN2, CMM2, INK4, INK4a, MLM, MTS1, p14, p14ARF, p16, p16INK4a, p19, p19Arf | Cyclin-dependent kinase inhibitor 2A |
| CEACAM5 | CD66e, CEA | Carcinoembryonic antigen-related cell adhesion molecule 5 |
| CEACAM6 | CD66c, NCA | Carcinoembryonic antigen-related cell adhesion molecule 6 (non-specific cross reacting antigen) |
| CENPF | hcp-1 | Centromere protein F, 350/400 kDa |
| CFHR1 | CFHL, CFHL1, CFHL1P, CFHR1P, FHR1, H36-1, H36-2, HFL1, HFL2 | Complement factor H-related 1 |
| CFLAR | c-FLIP, CASH, CASP8AP1, Casper, CLARP, FLAME, FLIP, I-FLICE, MRIT | CASP8 and FADD-like apoptosis regulator |
| CFTR | ABC35, ABCC7, CF, CFTR/MRP, dJ760C5.1, MRP7, TNR-CFTR | Cystic fibrosis transmembrane conductance regulator (ATP-binding cassette sub-family C, member 7) |
| CGA | FSHA, GPHa, GPHA1, HCG, LHA, TSHA | Glycoprotein hormones, alpha polypeptide |
| CGB | CGB3 | Chorionic gonadotropin, beta polypeptide |
| CGB5 | HCG | Chorionic gonadotropin, beta polypeptide 5 |
| CGB7 | CG-beta-a | Chorionic gonadotropin, beta polypeptide 7 |
| CGB8 | | Chorionic gonadotropin, beta polypeptide 8 |
| CHD7 | CRG, FLJ20357, FLJ20361, KIAA1416 | Chromodomain helicase DNA binding protein 7 |
| CHEK1 | CHK1 | Checkpoint kinase 1 |
| CHEK2 | bA444G7, CDS1, CHK2, HuCds1, PP1425, RAD53 | Checkpoint kinase 2 |
| CHFR | FLJ10796, RNF196 | Checkpoint with forkhead and ring finger domains, E3 ubiquitin protein ligase |
| CHGA | | Chromogranin A (parathyroid secretory protein 1) |
| CHI3L1 | GP39, YKL40 | Chitinase 3-like 1 (cartilage glycoprotein-39) |

TABLE 1-continued

| Gene | Gene synonym | Gene description |
| --- | --- | --- |
| CHP2 | | Calcineurin-like EF-hand protein 2 |
| CIB2 | DFNB48, KIP2, USH1J | Calcium and integrin binding family member 2 |
| CKB | CKBB | Creatine kinase, brain |
| CKS1B | CKS1, ckshs1 | CDC28 protein kinase regulatory subunit 1B |
| CKS2 | | CDC28 protein kinase regulatory subunit 2 |
| CLDN3 | C7orf1, CPE-R2, CPETR2, HRVP1, RVP1 | Claudin 3 |
| CLDN4 | CPE-R, CPETR, CPETR1, hCPE-R, WBSCR8 | Claudin 4 |
| CLDN7 | CEPTRL2, CPETRL2, Hs.84359 | Claudin 7 |
| CLEC3B | TN, TNA | C-type lectin domain family 3, member B |
| CLIC1 | NCC27, p64CLCP | Chloride intracellular channel 1 |
| CLIP1 | CLIP, CLIP-170, CLIP170, CYLN1, RSN | CAP-GLY domain containing linker protein 1 |
| CLSTN1 | CDHR12, CSTN1, KIAA0911 | Calsyntenin 1 |
| CLU | APOJ, CLI, CLU1, CLU2, KUB1, SGP-2, SP-40, TRPM-2 | Clusterin |
| CNN1 | Sm-Calp, SMCC | Calponin 1, basic, smooth muscle |
| CNTF | HCNTF | Ciliary neurotrophic factor |
| COL11A1 | CO11A1, COLL6, STL2 | Collagen, type XI, alpha 1 |
| COL17A1 | BP180, BPAG2 | Collagen, type XVII, alpha 1 |
| COL18A1 | KNO, KNO1, KS | Collagen, type XVIII, alpha 1 |
| COL1A1 | OI4 | Collagen, type I, alpha 1 |
| COL1A2 | OI4 | Collagen, type I, alpha 2 |
| COL4A2 | DKFZp686I14213, FLJ22259 | Collagen, type IV, alpha 2 |
| COL4A3 | | Collagen, type IV, alpha 3 (Goodpasture antigen) |
| COL4A4 | CA44 | Collagen, type IV, alpha 4 |
| COL4A5 | ASLN, ATS | Collagen, type IV, alpha 5 |
| COL6A1 | | Collagen, type VI, alpha 1 |
| COX17 | | COX17 cytochrome c oxidase copper chaperone |
| CP | | Ceruloplasmin (ferroxidase) |
| CRABP1 | CRABP, CRABP-I, CRABPI, RBP5 | Cellular retinoic acid binding protein 1 |
| CRADD | RAIDD | CASP2 and RIPK1 domain containing adaptor with death domain |
| CREBBP | CBP, KAT3A, RSTS, RTS | CREB binding protein |
| CRP | PTX1 | C-reactive protein, pentraxin-related |
| CRYAB | CRYA2, HSPB5 | Crystallin, alpha B |
| CSE1L | CAS, CSE1, XPO2 | CSE1 chromosome segregation 1-like (yeast) |
| CSF1 | M-CSF, MCSF, MGC31930 | Colony stimulating factor 1 (macrophage) |
| CSF1R | C-FMS, CD115, CSFR, FMS | Colony stimulating factor 1 receptor |
| CSF2 | GM-CSF, GMCSF | Colony stimulating factor 2 (granulocyte-macrophage) |
| CSF2RA | CD116, CSF2R | Colony stimulating factor 2 receptor, alpha, low-affinity (granulocyte-macrophage) |
| CSF3 | C17orf33, G-CSF, GCSF, MGC45931 | Colony stimulating factor 3 (granulocyte) |
| CSN1S1 | CASA, CSN1 | Casein alpha s1 |
| CSNK1E | CKIE, CKIepsilon, HCKIE | Casein kinase 1, epsilon |
| CSNK2A1 | | Casein kinase 2, alpha 1 polypeptide |
| CSNK2A2 | CSNK2A1 | Casein kinase 2, alpha prime polypeptide |
| CSNK2B | | Casein kinase 2, beta polypeptide |
| CST3 | | Cystatin C |
| CST6 | | Cystatin E/M |
| CSTA | STF1, STFA | Cystatin A (stefin A) |
| CSTB | CST6, EPM1, PME, STFB | Cystatin B (stefin B) |
| CTAG1A | ESO1, LAGE2A | Cancer/testis antigen 1A |
| CTAG1B | CT6.1, CTAG, CTAG1, ESO1, LAGE2A, LAGE2B, NY-ESO-1 | Cancer/testis antigen 1B |

TABLE 1-continued

| Gene | Gene synonym | Gene description |
|---|---|---|
| CTAG2 | CAMEL, CT6.2a, CT6.2b, ESO2, LAGE-1, LAGE-1a, LAGE-1b, LAGE1, MGC138724, MGC3803 | Cancer/testis antigen 2 |
| CTGF | CCN2, IGFBP8 | Connective tissue growth factor |
| CTNNB1 | armadillo, beta-catenin, CTNNB | Catenin (cadherin-associated protein), beta 1, 88 kDa |
| CTNNBL1 | C20orf33, FLJ21108, NAP, NYD-SP19, P14, P14L | Catenin, beta like 1 |
| CTSB | | Cathepsin B |
| CTSD | CLN10, CPSD | Cathepsin D |
| CTSH | ACC-4, ACC-5, CPSB | Cathepsin H |
| CTSL | CTSL1, FLJ31037 | Cathepsin L |
| CUL2 | | Cullin 2 |
| CUL5 | VACM-1 | Cullin 5 |
| CXCL1 | FSP, GRO1, GROa, MGSA, MGSA-a, NAP-3, SCYB1 | Chemokine (C-X-C motif) ligand 1 (melanoma growth stimulating activity, alpha) |
| CXCL10 | C7, crg-2, gIP-10, IFI10, INP10, IP-10, mob-1, SCYB10 | Chemokine (C-X-C motif) ligand 10 |
| CXCL13 | ANGIE, ANGIE2, BCA-1, BLC, BLR1L, SCYB13 | Chemokine (C-X-C motif) ligand 13 |
| CXCL2 | CINC-2a, GRO2, GROb, MGSA-b, MIP-2a, SCYB2 | Chemokine (C-X-C motif) ligand 2 |
| CXCL5 | ENA-78, SCYB5 | Chemokine (C-X-C motif) ligand 5 |
| CXCL8 | 3-10C, AMCF-I, b-ENAP, GCP-1, GCP1, IL-8, IL8, K60, LECT, LUCT, LYNAP, MDNCF, MONAP, NAF, NAP-1, NAP1, SCYB8, TSG-1 | Chemokine (C-X-C motif) ligand 8 |
| CXCL9 | CMK, crg-10, Humig, MIG, SCYB9 | Chemokine (C-X-C motif) ligand 9 |
| CXCR1 | CD181, CDw128a, CKR-1, CMKAR1, IL8RA | Chemokine (C-X-C motif) receptor 1 |
| CXCR2 | CD182, CMKAR2, IL8RB | Chemokine (C-X-C motif) receptor 2 |
| CXCR4 | CD184, D2S201E, fusin, HM89, HSY3RR, LESTR, NPY3R, NPYR, NPYY3R | Chemokine (C-X-C motif) receptor 4 |
| CYB5R3 | DIA1 | Cytochrome b5 reductase 3 |
| CYP19A1 | ARO, ARO1, aromatase, CPV1, CYAR, CYP19, P-450AROM | Cytochrome P450, family 19, subfamily A, polypeptide 1 |
| CYP1A2 | CP12, P3-450 | Cytochrome P450, family 1, subfamily A, polypeptide 2 |
| CYP2C19 | CPCJ, CYP2C, P450IIC19 | Cytochrome P450, family 2, subfamily C, polypeptide 19 |
| CYP2E1 | CYP2E | Cytochrome P450, family 2, subfamily E, polypeptide 1 |
| CYP3A4 | CYP3A3 | Cytochrome P450, family 3, subfamily A, polypeptide 4 |
| CYP3A5 | CP35, P450PCN3, PCN3 | Cytochrome P450, family 3, subfamily A, polypeptide 5 |
| DAD1 | OST2 | Defender against cell death 1 |
| DAPK1 | DAPK | Death-associated protein kinase 1 |
| DAXX | DAP6 | Death-domain associated protein |
| DBI | ACBD1, ACBP | Diazepam binding inhibitor (GABA receptor modulator, acyl-CoA binding protein) |
| DCC | IGDCC1, NTN1R1 | DCC netrin 1 receptor |
| DCDC1 | | Doublecortin domain containing 1 |
| DCN | DSPG2, SLRR1B | Decorin |
| DDB2 | DDBB, FLJ34321, UV-DDB2 | Damage-specific DNA binding protein 2, 48 kDa |
| DDIT3 | CHOP, CHOP10, GADD153 | DNA-damage-inducible transcript 3 |
| DEFA1 | DEF1, DEFA2, HNP-1, MRS | Defensin, alpha 1 |
| DEFA1B | | Defensin, alpha 1B |
| DEFA3 | DEF3, HNP-3 | Defensin, alpha 3, neutrophil-specific |
| DEK | D6S231E | DEK proto-oncogene |
| DES | CMD1I, CSM1, CSM2 | Desmin |
| DHFR | | Dihydrofolate reductase |
| DIAPH3 | AN, AUNA1, DRF3, FLJ34705, NSDAN | Diaphanous-related formin 3 |
| DLC1 | ARHGAP7, DLC-1, HP, p122-RhoGAP, STARD12 | DLC1 Rho GTPase activating protein |

TABLE 1-continued

| Gene | Gene synonym | Gene description |
| --- | --- | --- |
| DNAJC2 | MPHOSPH11, MPP11, ZRF1, ZUO1, zuotin | DnaJ (Hsp40) homolog, subfamily C, member 2 |
| DST | BP240, BPA, BPAG1, CATX-15, FLJ13425, FLJ21489, FLJ30627, FLJ32235, KIAA0728, MACF2 | Dystonin |
| DUSP1 | CL100, HVH1, MKP-1, PTPN10 | Dual specificity phosphatase 1 |
| DUSP14 | MKP-L, MKP6 | Dual specificity phosphatase 14 |
| DUSP4 | HVH2, MKP-2, TYP | Dual specificity phosphatase 4 |
| DVL3 | KIAA0208 | Dishevelled segment polarity protein 3 |
| DYNLL1 | DLC1, DLC8, DNCL1, hdlc1, LC8, PIN | Dynein, light chain, LC8-type 1 |
| DYRK2 | | Dual-specificity tyrosine-(Y)-phosphorylation regulated kinase 2 |
| E2F1 | RBBP3, RBP3 | E2F transcription factor 1 |
| E2F3 | | E2F transcription factor 3 |
| E2F5 | | E2F transcription factor 5, p130-binding |
| EBAG9 | EB9, RCAS1 | Estrogen receptor binding site associated, antigen, 9 |
| EDN1 | ET1 | Endothelin 1 |
| EEF2 | EEF-2, EF2 | Eukaryotic translation elongation factor 2 |
| EFNA1 | ECKLG, EPLG1, LERK1, TNFAIP4 | Ephrin-A1 |
| EFNA2 | ELF-1, EPLG6, LERK6 | Ephrin-A2 |
| EFNA5 | AF1, EPLG7, LERK7 | Ephrin-A5 |
| EFNB1 | CFNS, Elk-L, EPLG2, LERK2 | Ephrin-B1 |
| EFNB2 | EPLG5, Htk-L, HTKL, LERK5, MGC126226, MGC126227, MGC126228 | Ephrin-B2 |
| EFNB3 | EPLG8, LERK-8 | Ephrin-B3 |
| EGF | | Epidermal growth factor |
| EGFR | ERBB, ERBB1 | Epidermal growth factor receptor |
| EGR1 | AT225, G0S30, KROX-24, NGFI-A, TIS8, ZIF-268, ZNF225 | Early growth response 1 |
| EI24 | EPG4, PIG8, TP53I8 | Etoposide induced 2.4 |
| EIF3H | eIF3-gamma, eIF3-p40, eIF3h, EIF3S3 | Eukaryotic translation initiation factor 3, subunit H |
| EIF4E | EIF4E1, EIF4EL1, EIF4F | Eukaryotic translation initiation factor 4E |
| EIF4EBP1 | 4E-BP1, PHAS-I | Eukaryotic translation initiation factor 4E binding protein 1 |
| EIF4G1 | EIF4F, EIF4G, p220, PARK18 | Eukaryotic translation initiation factor 4 gamma, 1 |
| EIF4H | KIAA0038, WBSCR1, WSCR1 | Eukaryotic translation initiation factor 4H |
| EIF5A | EIF-5A, EIF5A1, MGC104255, MGC99547 | Eukaryotic translation initiation factor 5A |
| ELANE | ELA2, HLE, HNE, NE | Elastase, neutrophil expressed |
| ELK3 | ERP, NET, SAP2 | ELK3, ETS-domain protein (SRF accessory protein 2) |
| ENC1 | ENC-1, KLHL37, NRPB, PIG10, TP53I10 | Ectodermal-neural cortex 1 (with BTB domain) |
| ENG | CD105, END, HHT1, ORW, ORW1 | Endoglin |
| ENO1 | ENO1L1, MBP-1, MPB1, PPH | Enolase 1, (alpha) |
| ENO2 | | Enolase 2 (gamma, neuronal) |
| ENPP2 | ATX, PD-IALPHA, PDNP2 | Ectonucleotide pyrophosphatase/phosphodiesterase 2 |
| EPAS1 | bHLHe73, HIF2A, HLF, MOP2, PASD2 | Endothelial PAS domain protein 1 |
| EPCAM | 17-1A, 323/A3, CD326, CO-17A, EGP-2, EGP34, EGP40, Ep-CAM, ESA, GA733-2, HEA125, KS1/4, KSA, Ly74, M4S1, MH99, MIC18, MK-1, MOC31, TACST-1, TACSTD1, TROP1 | Epithelial cell adhesion molecule |

TABLE 1-continued

| Gene | Gene synonym | Gene description |
|---|---|---|
| EPHA1 | EPH, EPHT, EPHT1 | EPH receptor A1 |
| EPHA2 | ECK | EPH receptor A2 |
| EPHA3 | ETK, ETK1, HEK, HEK4, TYRO4 | EPH receptor A3 |
| EPHA4 | Hek8, TYRO1 | EPH receptor A4 |
| EPHA7 | Hek11 | EPH receptor A7 |
| EPHA8 | EEK, Hek3 | EPH receptor A8 |
| EPHB2 | DRT, EPHT3, ERK, Hek5, Tyro5 | EPH receptor B2 |
| EPHB3 | ETK2, Hek2, Tyro6 | EPH receptor B3 |
| EPHB4 | HTK, Tyro11 | EPH receptor B4 |
| EPHX1 | EPHX | Epoxide hydrolase 1, microsomal (xenobiotic) |
| EPO | EP | Erythropoietin |
| EPOR | | Erythropoietin receptor |
| ERBB2 | CD340, HER-2, HER2, NEU, NGL | V-erb-b2 avian erythroblastic leukemia viral oncogene homolog 2 |
| ERBB3 | HER3, LCCS2 | V-erb-b2 avian erythroblastic leukemia viral oncogene homolog 3 |
| ERBB4 | ALS19 | V-erb-b2 avian erythroblastic leukemia viral oncogene homolog 4 |
| ERCC1 | RAD10 | Excision repair cross-complementation group 1 |
| ERCC2 | EM9, MAG, MGC102762, MGC126218, MGC126219, TFIIH, XPD | Excision repair cross-complementation group 2 |
| ERCC3 | BTF2, GTF2H, RAD25, TFIIH, XPB | Excision repair cross-complementation group 3 |
| ERCC4 | FANCQ, RAD1, XPF | Excision repair cross-complementation group 4 |
| ERCC5 | ERCM2, XPGC | Excision repair cross-complementation group 5 |
| ERCC6 | ARMD5, CKN2, CSB, RAD26 | Excision repair cross-complementation group 6 |
| ESR1 | Era, ESR, NR3A1 | Estrogen receptor 1 |
| ESR2 | Erb, NR3A2 | Estrogen receptor 2 (ER beta) |
| ETHE1 | HSCO, YF13H12 | Ethylmalonic encephalopathy 1 |
| ETV4 | E1A-F, E1AF, PEA3 | Ets variant 4 |
| ETV5 | ERM | Ets variant 5 |
| EXT1 | LGCR, LGS, ttv | Exostosin glycosyltransferase 1 |
| EZH2 | ENX-1, EZH1, KMT6, KMT6A | Enhancer of zeste 2 polycomb repressive complex 2 subunit |
| EZR | VIL2 | Ezrin |
| F13A1 | F13A | Coagulation factor XIII, A1 polypeptide |
| F13B | FXIIIB | Coagulation factor XIII, B polypeptide |
| F2 | | Coagulation factor II (thrombin) |
| F3 | CD142 | Coagulation factor III (thromboplastin, tissue factor) |
| FABP1 | L-FABP | Fatty acid binding protein 1, liver |
| FABP2 | I-FABP | Fatty acid binding protein 2, intestinal |
| FABP4 | A-FABP, aP2 | Fatty acid binding protein 4, adipocyte |
| FABP5 | E-FABP, KFABP, PA-FABP | Fatty acid binding protein 5 (psoriasis-associated) |
| FADD | GIG3, MORT1 | Fas (TNFRSF6)-associated via death domain |
| FAF1 | CGI-03, hFAF1, HFAF1s, UBXD12, UBXN3A | Fas (TNFRSF6) associated factor 1 |
| FAM129A | C1orf24, GIG39, NIBAN | Family with sequence similarity 129, member A |
| FAP | DPPIV | Fibroblast activation protein, alpha |
| FAS | APO-1, APT1, CD95, FAS1, TNFRSF6 | Fas cell surface death receptor |
| FASLG | APT1LG1, CD178, FasL, TNFSF6 | Fas ligand (TNF superfamily, member 6) |
| FASN | FAS, SDR27X1 | Fatty acid synthase |
| FBXO6 | FBG2, FBS2, FBX6, Fbx6b | F-box protein 6 |
| FCER2 | CD23, CD23A, CLEC4J, FCE2 | Fc fragment of IgE, low affinity II, receptor for (CD23) |
| FEN1 | FEN-1, MF1, RAD2 | Flap structure-specific endonuclease 1 |
| FES | FPS | FES proto-oncogene, tyrosine kinase |
| FGA | | Fibrinogen alpha chain |
| FGB | | Fibrinogen beta chain |
| FGF1 | AFGF, ECGF, ECGF-beta, ECGFA, ECGFB, FGF-alpha, FGFA, GLIO703, HBGF1 | Fibroblast growth factor 1 (acidic) |

TABLE 1-continued

| Gene | Gene synonym | Gene description |
| --- | --- | --- |
| FGF17 | FGF-13 | Fibroblast growth factor 17 |
| FGF18 | FGF-18, ZFGF5 | Fibroblast growth factor 18 |
| FGF19 | | Fibroblast growth factor 19 |
| FGF2 | FGFB | Fibroblast growth factor 2 (basic) |
| FGF23 | | Fibroblast growth factor 23 |
| FGF3 | HBGF-3, INT2 | Fibroblast growth factor 3 |
| FGF4 | HBGF-4, HST, HST-1, HSTF1, K-FGF, KFGF | Fibroblast growth factor 4 |
| FGF6 | | Fibroblast growth factor 6 |
| FGF7 | KGF | Fibroblast growth factor 7 |
| FGF8 | AIGF | Fibroblast growth factor 8 (androgen-induced) |
| FGF9 | | Fibroblast growth factor 9 |
| FGFR1 | BFGFR, CD331, CEK, FLG, FLT2, H2, H3, H4, H5, KAL2, N-SAM | Fibroblast growth factor receptor 1 |
| FGFR2 | BEK, CD332, CEK3, CFD1, ECT1, JWS, K-SAM, KGFR, TK14, TK25 | Fibroblast growth factor receptor 2 |
| FGFR3 | ACH, CD333, CEK2, JTK4 | Fibroblast growth factor receptor 3 |
| FGFR4 | CD334, JTK2 | Fibroblast growth factor receptor 4 |
| FGG | | Fibrinogen gamma chain |
| FHIT | AP3Aase, FRA3B | Fragile histidine triad |
| FIGF | VEGF-D, VEGFD | C-fos induced growth factor (vascular endothelial growth factor D) |
| FKBP5 | FKBP51, FKBP54, P54, PPIase, Ptg-10 | FK506 binding protein 5 |
| FKBP8 | FKBP38, FKBPr38 | FK506 binding protein 8, 38 kDa |
| FLT1 | FLT, VEGFR1 | Fms-related tyrosine kinase 1 |
| FLT4 | PCL, VEGFR3 | Fms-related tyrosine kinase 4 |
| FMO5 | | Flavin containing monooxygenase 5 |
| FN1 | CIG, FINC, GFND2, LETS, MSF | Fibronectin 1 |
| FOLH1 | FOLH, GCP2, GCPII, NAALAD1, NAALAdase, PSM, PSMA | Folate hydrolase (prostate-specific membrane antigen) 1 |
| FOS | AP-1, c-fos | FBJ murine osteosarcoma viral oncogene homolog |
| FOSL1 | fra-1 | FOS-like antigen 1 |
| FOXJ1 | FKHL13, HFH-4, HFH4 | Forkhead box J1 |
| FOXM1 | FKHL16, HFH-11, HNF-3, INS-1, MPHOSPH2, MPP2, TGT3, trident | Forkhead box M1 |
| FOXO1 | FKH1, FKHR, FOXO1A | Forkhead box O1 |
| FOXO3 | AF6q21, FKHRL1, FOXO2, FOXO3A | Forkhead box O3 |
| FOXQ1 | HFH1 | Forkhead box Q1 |
| FSCN1 | FLJ38511, p55, SNL | Fascin actin-bundling protein 1 |
| FSHB | | Follicle stimulating hormone, beta polypeptide |
| FST | FS | Follistatin |
| FTH1 | FHC, FTH, FTHL6, PIG15, PLIF | Ferritin, heavy polypeptide 1 |
| FTL | MGC71996, NBIA3 | Ferritin, light polypeptide |
| FZD1 | DKFZp564G072 | Frizzled class receptor 1 |
| FZD2 | | Frizzled class receptor 2 |
| G6PD | G6PD1 | Glucose-6-phosphate dehydrogenase |
| GADD45A | DDIT1, GADD45 | Growth arrest and DNA-damage-inducible, alpha |
| GADD45G | CR6, DDIT2, GADD45gamma, GRP17 | Growth arrest and DNA-damage-inducible, gamma |
| GAS1 | | Growth arrest-specific 1 |
| GAST | GAS | Gastrin |
| GATA3 | HDR | GATA binding protein 3 |
| GCLM | GLCLR | Glutamate-cysteine ligase, modifier subunit |
| GDF15 | MIC-1, MIC1, NAG-1, PDF, PLAB, PTGFB | Growth differentiation factor 15 |
| GDNF | ATF1, ATF2, HFB1-GDNF | Glial cell derived neurotrophic factor |
| GH1 | GH, GH-N, GHN, hGH-N | Growth hormone 1 |
| GH2 | GH-V, GH2, GHL, GHV, hGH-V | Growth hormone 2 |
| GJA1 | CX43, GJAL, ODD, ODDD, ODOD, SDTY3 | Gap junction protein, alpha 1, 43 kDa |

TABLE 1-continued

| Gene | Gene synonym | Gene description |
|---|---|---|
| GJB5 | CX31.1 | Gap junction protein, beta 5, 31.1 kDa |
| GLO1 | GLOD1 | Glyoxalase I |
| GMNN | Gem | Geminin, DNA replication inhibitor |
| GNAS | GNAS1, GNASXL, GPSA, NESP, NESP55, SCG6 | GNAS complex locus |
| GPA33 | A33 | Glycoprotein A33 (transmembrane) |
| GPC3 | DGSX, OCI-5, SDYS, SGB, SGBS, SGBS1 | Glypican 3 |
| GPI | AMF, NLK | Glucose-6-phosphate isomerase |
| GPX1 | | Glutathione peroxidase 1 |
| GPX2 | GSHPX-GI | Glutathione peroxidase 2 (gastrointestinal) |
| GRB10 | | Growth factor receptor-bound protein 10 |
| GRB2 | NCKAP2 | Growth factor receptor-bound protein 2 |
| GRB7 | | Growth factor receptor-bound protein 7 |
| GSK3A | | Glycogen synthase kinase 3 alpha |
| GSN | DKFZp313L0718 | Gelsolin |
| GSR | | Glutathione reductase |
| GSTM1 | GST1, H-B, MU | Glutathione S-transferase mu 1 |
| GSTM3 | GST5 | Glutathione S-transferase mu 3 (brain) |
| GSTP1 | FAEES3, GST3, GSTP | Glutathione S-transferase pi 1 |
| HDAC10 | DKFZP761B039 | Histone deacetylase 10 |
| HDAC2 | RPD3, YAF1 | Histone deacetylase 2 |
| HDAC5 | FLJ90614, KIAA0600, NY-CO-9 | Histone deacetylase 5 |
| HGF | DFNB39, F-TCF, HGFB, HPTA, SF | Hepatocyte growth factor (hepapoietin A; scatter factor) |
| HGFAC | HGFA, HGFAP | HGF activator |
| HIF1A | bHLHe78, HIF-1alpha, HIF1, MOP1, PASD8 | Hypoxia inducible factor 1, alpha subunit (basic helix-loop-helix transcription factor) |
| HIP1R | FLJ14000, HIP12, HIP3, ILWEQ, KIAA0655 | Huntingtin interacting protein 1 related |
| HIST1H2AC | H2AFL | Histone cluster 1, H2ac |
| HK1 | | Hexokinase 1 |
| HK2 | | Hexokinase 2 |
| HLA-G | | Major histocompatibility complex, class I, G |
| HMGA1 | HMGIY | High mobility group AT-hook 1 |
| HMGA2 | BABL, HMGIC, LIPO | High mobility group AT-hook 2 |
| HMOX1 | bK286B10, HO-1 | Heme oxygenase (decycling) 1 |
| HOXA5 | HOX1, HOX1C | Homeobox A5 |
| HOXA9 | HOX1, HOX1G | Homeobox A9 |
| HP | | Haptoglobin |
| HPGD | SDR36C1 | Hydroxyprostaglandin dehydrogenase 15-(NAD) |
| HPN | TMPRSS1 | Hepsin |
| HRAS | HRAS1 | Harvey rat sarcoma viral oncogene homolog |
| HSF1 | HSTF1 | Heat shock transcription factor 1 |
| HSP90AA1 | FLJ31884, Hsp89, Hsp90, HSP90N, HSPC1, HSPCA | Heat shock protein 90 kDa alpha (cytosolic), class A member 1 |
| HSP90AB1 | HSPC2, HSPCB | Heat shock protein 90 kDa alpha (cytosolic), class B member 1 |
| HSP90B1 | GP96, GRP94, TRA1 | Heat shock protein 90 kDa beta (Grp94), member 1 |
| HSPA1A | HSP70-1, HSPA1 | Heat shock 70 kDa protein 1A |
| HSPA1B | HSP70-2 | Heat shock 70 kDa protein 1B |
| HSPA1L | HSP70-HOM, hum70t | Heat shock 70 kDa protein 1-like |
| HSPA2 | | Heat shock 70 kDa protein 2 |
| HSPA4 | HS24/P52, HSPH2 | Heat shock 70 kDa protein 4 |
| HSPA8 | HSC70, HSC71, HSC73, HSPA10 | Heat shock 70 kDa protein 8 |
| HSPB1 | Hs.76067, Hsp25, HSP27, HSP28 | Heat shock 27 kDa protein 1 |
| HSPD1 | GROEL, HSP60, SPG13 | Heat shock 60 kDa protein 1 (chaperonin) |
| HSPE1 | CPN10, GROES | Heat shock 10 kDa protein 1 |
| HSPH1 | HSP105A, HSP105B, KIAA0201, NY-CO-25 | Heat shock 105 kDa/110 kDa protein 1 |
| IBSP | BSP, BSP-II, SP-II | Integrin-binding sialoprotein |
| ICAM1 | BB2, CD54 | Intercellular adhesion molecule 1 |
| ID1 | bHLHb24, dJ857M17.1.2 | Inhibitor of DNA binding 1, dominant negative helix-loop-helix protein |
| ID2 | bHLHb26, GIG8 | Inhibitor of DNA binding 2, dominant negative helix-loop-helix protein |

TABLE 1-continued

| Gene | Gene synonym | Gene description |
|---|---|---|
| ID3 | bHLHb25, HEIR-1 | Inhibitor of DNA binding 3, dominant negative helix-loop-helix protein |
| IDO1 | IDO, INDO | Indoleamine 2, 3-dioxygenase 1 |
| IFNA1 | IFL, IFN, IFN-ALPHA, IFN-alphaD, IFNA13, IFNA@ | Interferon, alpha 1 |
| IFNA13 | | Interferon, alpha 13 |
| IFNAR1 | IFNAR, IFRC | Interferon (alpha, beta and omega) receptor 1 |
| IFNAR2 | IFNABR | Interferon (alpha, beta and omega) receptor 2 |
| IFNB1 | IFB, IFF, IFNB | Interferon, beta 1, fibroblast |
| IFNG | | Interferon, gamma |
| IGF1 | IGF-I, IGF1A, IGFI | Insulin-like growth factor 1 (somatomedin C) |
| IGF1R | CD221, IGFIR, IGFR, JTK13, MGC18216 | Insulin-like growth factor 1 receptor |
| IGF2 | C11orf43, FLJ44734, IGF-II | Insulin-like growth factor 2 |
| IGF2R | CD222, CIMPR, M6P-R, MPR1, MPRI | Insulin-like growth factor 2 receptor |
| IGFBP2 | IBP2 | Insulin-like growth factor binding protein 2, 36 kDa |
| IGFBP3 | BP-53, IBP3 | Insulin-like growth factor binding protein 3 |
| IL10 | CSIF, IL-10, IL10A, TGIF | Interleukin 10 |
| IL11 | AGIF, IL-11 | Interleukin 11 |
| IL12A | CLMF, IL-12A, NFSK, NKSF1, p35 | Interleukin 12A |
| IL13 | ALRH, BHR1, IL-13, MGC116786, MGC116788, MGC116789, P600 | Interleukin 13 |
| IL13RA2 | CD213a2, CT19, IL-13R, IL13BP | Interleukin 13 receptor, alpha 2 |
| IL15 | IL-15, MGC9721 | Interleukin 15 |
| IL16 | FLJ16806, FLJ42735, HsT19289, IL-16, LCF, prIL-16 | Interleukin 16 |
| IL17A | CTLA8, IL-17, IL-17A, IL17 | Interleukin 17A |
| IL17B | IL-17B, IL-20, MGC138900, MGC138901, NIRF, ZCYTO7 | Interleukin 17B |
| IL18 | IGIF, IL-18, IL-1g, IL1F4 | Interleukin 18 |
| IL1A | IL-1A, IL1, IL1-ALPHA, IL1F1 | Interleukin 1, alpha |
| IL1B | IL-1B, IL1-BETA, IL1F2 | Interleukin 1, beta |
| IL1R1 | CD121A, D2S1473, IL1R, IL1RA | Interleukin 1 receptor, type I |
| IL1R2 | CD121b, IL1RB | Interleukin 1 receptor, type II |
| IL1RN | ICIL-1RA, IL-1RN, IL1F3, IL1RA, IRAP, MGC10430 | Interleukin 1 receptor antagonist |
| IL2 | IL-2, TCGF | Interleukin 2 |
| IL24 | C49A, FISP, IL-24, IL10B, mda-7, Mob-5, ST16 | Interleukin 24 |
| IL2RA | CD25, IDDM10, IL2R | Interleukin 2 receptor, alpha |
| IL2RB | CD122, IL15RB | Interleukin 2 receptor, beta |
| IL2RG | CD132, CIDX, IMD4, SCIDX1 | Interleukin 2 receptor, gamma |
| IL4 | BCGF-1, BCGF1, BSF1, IL-4, MGC79402 | Interleukin 4 |
| IL4R | CD124 | Interleukin 4 receptor |
| IL5 | EDF, IL-5, TRF | Interleukin 5 |
| IL6 | BSF2, HGF, HSF, IFNB2, IL-6 | Interleukin 6 |
| IL6R | CD126 | Interleukin 6 receptor |
| IL6ST | CD130, GP130 | Interleukin 6 signal transducer |
| IL7 | IL-7 | Interleukin 7 |
| IL9 | HP40, IL-9, P40 | Interleukin 9 |
| ILF3 | DRBP76, MPHOSPH4, MPP4, NF90, NFAR-1 | Interleukin enhancer binding factor 3, 90 kDa |
| ILK | | Integrin-linked kinase |
| INHBA | | Inhibin, beta A |
| INHBB | | Inhibin, beta B |
| INS | IDDM1, IDDM2 | Insulin |
| IRF1 | MAR | Interferon regulatory factor 1 |
| IRF4 | LSIRF, MUM1 | Interferon regulatory factor 4 |

TABLE 1-continued

| Gene | Gene synonym | Gene description |
| --- | --- | --- |
| ITGA1 | CD49a, VLA1 | Integrin, alpha 1 |
| ITGA2 | CD49B | Integrin, alpha 2 (CD49B, alpha 2 subunit of VLA-2 receptor) |
| ITGA2B | CD41, CD41B, GP2B, PPP1R93 | Integrin, alpha 2b (platelet glycoprotein IIb of IIb/IIIa complex, antigen CD41) |
| ITGA3 | CD49c, GAP-B3, MSK18, VCA-2, VLA3a | Integrin, alpha 3 (antigen CD49C, alpha 3 subunit of VLA-3 receptor) |
| ITGA4 | CD49D | Integrin, alpha 4 (antigen CD49D, alpha 4 subunit of VLA-4 receptor) |
| ITGA5 | CD49e, FNRA | Integrin, alpha 5 (fibronectin receptor, alpha polypeptide) |
| ITGA6 | CD49f | Integrin, alpha 6 |
| ITGAM | CD11B, CR3A, MAC-1 | Integrin, alpha M (complement component 3 receptor 3 subunit) |
| ITGAV | CD51, MSK8, VNRA, VTNR | Integrin, alpha V |
| ITGB1 | CD29, FNRB, GPIIA, MDF2, MSK12 | Integrin, beta 1 (fibronectin receptor, beta polypeptide, antigen CD29 includes MDF2, MSK12) |
| ITGB3 | CD61, GP3A, GPIIIa | Integrin, beta 3 (platelet glycoprotein IIIa, antigen CD61) |
| ITGB4 | CD104 | Integrin, beta 4 |
| ITGB5 | | Integrin, beta 5 |
| ITGB6 | | Integrin, beta 6 |
| ITGB8 | | Integrin, beta 8 |
| ITIH4 | H4P, IHRP, ITIHL1 | Inter-alpha-trypsin inhibitor heavy chain family, member 4 |
| JKAMP | C14orf100, CDA06, HSPC213, HSPC327, JAMP | JNK1/MAPK8-associated membrane protein |
| JTB | hJT | Jumping translocation breakpoint |
| JUN | AP-1, c-Jun | Jun proto-oncogene |
| JUND | AP-1 | Jun D proto-oncogene |
| JUP | CTNNG, DP3, DPIII, PDGB, PKGB | Junction plakoglobin |
| KAT2B | GCN5, GCN5L, P/CAF, PCAF | K(lysine) acetyltransferase 2B |
| KDR | CD309, FLK1, VEGFR, VEGFR2 | Kinase insert domain receptor (a type III receptor tyrosine kinase) |
| KIF2A | HK2, KIF2 | Kinesin heavy chain member 2A |
| KIF2C | CT139, KNSL6, MCAK | Kinesin family member 2C |
| KISS1 | | KiSS-1 metastasis-suppressor |
| KIT | C-Kit, CD117, PBT, SCFR | V-kit Hardy-Zuckerman 4 feline sarcoma viral oncogene homolog |
| KITLG | FPH2, Kitl, KL-1, MGF, SCF, SF | KIT ligand |
| KLF4 | EZF, GKLF | Kruppel-like factor 4 (gut) |
| KLF5 | BTEB2, CKLF, IKLF | Kruppel-like factor 5 (intestinal) |
| KLK10 | NES1, PRSSL1 | Kallikrein-related peptidase 10 |
| KLK11 | PRSS20, TLSP | Kallikrein-related peptidase 11 |
| KLK13 | KLK-L4 | Kallikrein-related peptidase 13 |
| KLK14 | KLK-L6 | Kallikrein-related peptidase 14 |
| KLK15 | ACO, HSRNASPH, prostinogen | Kallikrein-related peptidase 15 |
| KLK2 | | Kallikrein-related peptidase 2 |
| KLK3 | APS, PSA | Kallikrein-related peptidase 3 |
| KLK4 | EMSP, EMSP1, KLK-L1, PRSS17, PSTS | Kallikrein-related peptidase 4 |
| KLK5 | KLK-L2, SCTE | Kallikrein-related peptidase 5 |
| KLK6 | Bssp, Klk7, neurosin, PRSS18, PRSS9 | Kallikrein-related peptidase 6 |
| KLK7 | PRSS6, SCCE | Kallikrein-related peptidase 7 |
| KLK8 | HNP, neuropsin, ovasin, PRSS19, TADG14 | Kallikrein-related peptidase 8 |
| KLRK1 | CD314, D12S2489E, KLR, NKG2-D, NKG2D | Killer cell lectin-like receptor subfamily K, member 1 |
| KRAS | KRAS1, KRAS2 | Kirsten rat sarcoma viral oncogene homolog |
| KRT13 | CK13, K13, MGC161462, MGC3781 | Keratin 13 |
| KRT14 | EBS3, EBS4 | Keratin 14 |
| KRT15 | CK15, K15, K1CO | Keratin 15 |
| KRT17 | PCHC1 | Keratin 17 |
| KRT18 | | Keratin 18 |
| KRT19 | CK19, K19, K1CS, MGC15366 | Keratin 19 |
| KRT4 | CK4, CYK4, K4 | Keratin 4 |
| KRT8 | CARD2, CK8, CYK8, K2C8, K8, KO | Keratin 8 |

TABLE 1-continued

| Gene | Gene synonym | Gene description |
|---|---|---|
| LALBA | LYZL7 | Lactalbumin, alpha- |
| LAMB1 | CLM | Laminin, beta 1 |
| LAMC1 | LAMB2 | Laminin, gamma 1 (formerly LAMB2) |
| LCN1 | MGC71975, PMFA, TLC, TP, VEGP | Lipocalin 1 |
| LDHA | | Lactate dehydrogenase A |
| LEP | OB, OBS | Leptin |
| LGALS3 | GALIG, LGALS2, MAC-2 | Lectin, galactoside-binding, soluble, 3 |
| LGALS3BP | 90K, BTBD17B, CyCAP, gp90, M2BP, MAC-2-BP, TANGO10B | Lectin, galactoside-binding, soluble, 3 binding protein |
| LGALS4 | GAL4 | Lectin, galactoside-binding, soluble, 4 |
| LGI1 | EPITEMPIN, EPT, ETL1, IB1099 | Leucine-rich, glioma inactivated 1 |
| LGMN | LGMN1, PRSC1 | Legumain |
| LHB | CGB4, hLHB, LSH-B | Luteinizing hormone beta polypeptide |
| LHX1 | LIM-1, LIM1 | LIM homeobox 1 |
| LIF | CDF, DIA, HILDA | Leukemia inhibitory factor |
| LIG4 | | Ligase IV, DNA, ATP-dependent |
| LIMK1 | LIMK | LIM domain kinase 1 |
| LMNA | CMD1A, HGPS, LGMD1B, LMN1, LMNL1, PRO1 | Lamin A/C |
| LRP1B | LRP-DIT, LRPDIT | Low density lipoprotein receptor-related protein 1B |
| LRP6 | ADCAD2 | Low density lipoprotein receptor-related protein 6 |
| LTA | LT, TNFB, TNFSF1 | Lymphotoxin alpha |
| LTA4H | | Leukotriene A4 hydrolase |
| LTB | p33, TNFC, TNFSF3 | Lymphotoxin beta (TNF superfamily, member 3) |
| LTBR | D12S370, TNF-R-III, TNFCR, TNFR-RP, TNFR2-RP, TNFRSF3 | Lymphotoxin beta receptor (TNFR superfamily, member 3) |
| LTF | HLF2 | Lactotransferrin |
| MAD2L1 | HSMAD2, MAD2 | MAD2 mitotic arrest deficient-like 1 (yeast) |
| MAD2L2 | MAD2B, POLZ2, REV7 | MAD2 mitotic arrest deficient-like 2 (yeast) |
| MAGEA3 | CT1.3, HIP8, HYPD, MAGE3, MGC14613 | Melanoma antigen family A, 3 |
| MAGEA4 | CT1.4, MAGE-41, MAGE-X2, MAGE4, MAGE4A, MAGE4B, MGC21336 | Melanoma antigen family A, 4 |
| MAGEA6 | CT1.6, MAGE6 | Melanoma antigen family A, 6 |
| MAGEB5 | CT3.3, MAGE-B5 | Melanoma antigen family B, 5 |
| MAGEB6 | CT3.4, FLJ40242, MAGE-B6, MAGEB6A | Melanoma antigen family B, 6 |
| MAGEC1 | CT7, CT7.1, MAGE-C1, MGC39366 | Melanoma antigen family C, 1 |
| MAGEC2 | CT10, MAGE-C2, MAGEE1 | Melanoma antigen family C, 2 |
| MAGEC3 | CT7.2, HCA2, MAGE-C3 | Melanoma antigen family C, 3 |
| MAGED1 | DLXIN-1, NRAGE | Melanoma antigen family D, 1 |
| MAGED2 | 11B6, BCG1, HCA10, JCL-1, MAGE-D2, MAGED, MGC8386 | Melanoma antigen family D, 2 |
| MAGI1 | AIP3, BAIAP1, BAP1, MAGI-1, TNRC19, WWP3 | Membrane associated guanylate kinase, WW and PDZ domain containing 1 |
| MAP2K1 | MAPKK1, MEK1, PRKMK1 | Mitogen-activated protein kinase kinase 1 |
| MAP2K2 | MEK2, PRKMK2 | Mitogen-activated protein kinase kinase 2 |
| MAP2K4 | JNKK1, MEK4, MKK4, PRKMK4, SERK1 | Mitogen-activated protein kinase kinase 4 |
| MAPK1 | ERK, ERK2, MAPK2, p41mapk, PRKM1, PRKM2 | Mitogen-activated protein kinase 1 |
| MAPK14 | CSBP1, CSBP2, CSPB1, Mxi2, p38, PRKM14, PRKM15 | Mitogen-activated protein kinase 14 |
| MAPK3 | ERK1, p44erk1, p44mapk, PRKM3 | Mitogen-activated protein kinase 3 |
| MAPK7 | BMK1, ERK5, PRKM7 | Mitogen-activated protein kinase 7 |
| MAPK8 | JNK, JNK1, PRKM8, SAPK1 | Mitogen-activated protein kinase 8 |
| MAPKAPK2 | | Mitogen-activated protein kinase-activated protein kinase 2 |
| MBD1 | CXXC3, PCM1 | Methyl-CpG binding domain protein 1 |
| MBD2 | | Methyl-CpG binding domain protein 2 |

TABLE 1-continued

| Gene | Gene synonym | Gene description |
|---|---|---|
| MBD4 | MED1 | Methyl-CpG binding domain protein 4 |
| MCL1 | BCL2L3, Mcl-1 | Myeloid cell leukemia 1 |
| MCM2 | BM28, CCNL1, cdc19, CDCL1, D3S3194, KIAA0030 | Minichromosome maintenance complex component 2 |
| MCM3 | | Minichromosome maintenance complex component 3 |
| MCM5 | CDC46 | Minichromosome maintenance complex component 5 |
| MCM7 | CDC47, MCM2, PPP1R104 | Minichromosome maintenance complex component 7 |
| MDH1 | | Malate dehydrogenase 1, NAD (soluble) |
| MDK | FLJ27379, MK, NEGF2 | Midkine (neurite growth-promoting factor 2) |
| MDM2 | HDM2, MGC5370 | MDM2 proto-oncogene, E3 ubiquitin protein ligase |
| MECP2 | MRX16, MRX79, RTT | Methyl CpG binding protein 2 |
| MED1 | CRSP1, CRSP200, DRIP230, PBP, PPARBP, PPARGBP, RB18A, TRAP220, TRIP2 | Mediator complex subunit 1 |
| MET | HGFR, RCCP2 | MET proto-oncogene, receptor tyrosine kinase |
| MFGE8 | BA46, EDIL1, hP47, HsT19888, MFG-E8, OAcGD3S, SED1, SPAG10 | Milk fat globule-EGF factor 8 protein |
| MGMT | | O-6-methylguanine-DNA methyltransferase |
| MIA | CD-RAP | Melanoma inhibitory activity |
| MIF | GIF, GLIF | Macrophage migration inhibitory factor (glycosylation-inhibiting factor) |
| MKI67 | MIB-, PPP1R105 | Marker of proliferation Ki-67 |
| MLH1 | COCA2, FCC2, HNPCC, HNPCC2 | MutL homolog 1 |
| MLLT11 | AF1Q | Myeloid/lymphoid or mixed-lineage leukemia (trithorax homolog, *Drosophila*); translocated to, 11 |
| MME | CALLA, CD10, NEP | Membrane metallo-endopeptidase |
| MMP1 | CLG | Matrix metallopeptidase 1 (interstitial collagenase) |
| MMP10 | STMY2 | Matrix metallopeptidase 10 (stromelysin 2) |
| MMP11 | STMY3 | Matrix metallopeptidase 11 (stromelysin 3) |
| MMP12 | HME | Matrix metallopeptidase 12 (macrophage elastase) |
| MMP13 | CLG3 | Matrix metallopeptidase 13 (collagenase 3) |
| MMP14 | MT1-MMP | Matrix metallopeptidase 14 (membrane-inserted) |
| MMP15 | MT2-MMP, MTMMP2, SMCP-2 | Matrix metallopeptidase 15 (membrane-inserted) |
| MMP16 | C8orf57, DKFZp761D112, MT3-MMP | Matrix metallopeptidase 16 (membrane-inserted) |
| MMP2 | CLG4, CLG4A, TBE-1 | Matrix metallopeptidase 2 (gelatinase A, 72 kDa gelatinase, 72 kDa type IV collagenase) |
| MMP3 | STMY, STMY1 | Matrix metallopeptidase 3 (stromelysin 1, progelatinase) |
| MMP7 | MPSL1, PUMP-1 | Matrix metallopeptidase 7 (matrilysin, uterine) |
| MMP8 | CLG1 | Matrix metallopeptidase 8 (neutrophil collagenase) |
| MMP9 | CLG4B | Matrix metallopeptidase 9 (gelatinase B, 92 kDa gelatinase, 92 kDa type IV collagenase) |
| MPO | | Myeloperoxidase |
| MRE11A | ATLD, MRE11 | MRE11 meiotic recombination 11 homolog A (*S. cerevisiae*) |
| MSH6 | GTBP | MutS homolog 6 |
| MSLN | CAK1, MPF | Mesothelin |
| MSMB | IGBF, MSP, MSPB, PN44, PRPS, PSP, PSP-94, PSP57, PSP94 | Microseminoprotein, beta- |
| MSR1 | CD204, SCARA1 | Macrophage scavenger receptor 1 |
| MT1A | MT1, MT1S | Metallothionein 1A |
| MT1G | MT1, MT1K | Metallothionein 1G |

TABLE 1-continued

| Gene | Gene synonym | Gene description |
|---|---|---|
| MTA1 | | Metastasis associated 1 |
| MUC1 | ADMCKD, ADMCKD1, CD227, MCD, MCKD, MCKD1, PEM, PUM | Mucin 1, cell surface associated |
| MUTYH | MYH | MutY homolog |
| MVP | LRP, VAULT1 | Major vault protein |
| MXI1 | bHLHc11, MAD2, MXD2, MXI | MAX interactor 1, dimerization protein |
| MYBL2 | B-MYB, BMYB | V-myb avian myeloblastosis viral oncogene homolog-like 2 |
| MYC | bHLHe39, c-Myc, MYCC | V-myc avian myelocytomatosis viral oncogene homolog |
| MYOCD | MYCD | Myocardin |
| MYOD1 | bHLHc1, MYF3, MYOD, PUM | Myogenic differentiation 1 |
| MYOG | bHLHc3, MYF4 | Myogenin (myogenic factor 4) |
| NAGA | D22S674 | N-acetylgalactosaminidase, alpha- |
| NAIP | BIRC1, NLRB1 | NLR family, apoptosis inhibitory protein |
| NAMPT | PBEF, PBEF1 | Nicotinamide phosphoribosyltransferase |
| NAT2 | AAC2 | N-acetyltransferase 2 (arylamine N-acetyltransferase) |
| NCAM1 | CD56, NCAM | Neural cell adhesion molecule 1 |
| NCOA3 | ACTR, AIB1, bHLHe42, CAGH16, KAT13B, p/CIP, RAC3, SRC-3, SRC3, TNRC16, TRAM-1 | Nuclear receptor coactivator 3 |
| NDRG1 | CAP43, DRG1, NDR1, RTP, TDD5 | N-myc downstream regulated 1 |
| NEDD8 | Nedd-8 | Neural precursor cell expressed, developmentally down-regulated 8 |
| NEO1 | HsT17534, IGDCC2, NGN, NTN1R2 | Neogenin 1 |
| NFKB1 | KBF1, NF-kappaB, NF-kB1, NFkappaB, NFKB-p50, p105, p50 | Nuclear factor of kappa light polypeptide gene enhancer in B-cells 1 |
| NFKB2 | LYT-10, NF-kB2, p105, p52 | Nuclear factor of kappa light polypeptide gene enhancer in B-cells 2 (p49/p100) |
| NFKBIA | IkappaBalpha, IKBA, MAD-3, NFKBI | Nuclear factor of kappa light polypeptide gene enhancer in B-cells inhibitor, alpha |
| NFKBIE | IKBE | Nuclear factor of kappa light polypeptide gene enhancer in B-cells inhibitor, epsilon |
| NGF | NGFB | Nerve growth factor (beta polypeptide) |
| NGFR | CD271, p75NTR, TNFRSF16 | Nerve growth factor receptor |
| NKX3-1 | BAPX2, NKX3.1, NKX3A | NK3 homeobox 1 |
| NME1 | NDPKA, NM23, NM23-H1 | NME/NM23 nucleoside diphosphate kinase 1 |
| NME2 | NDPKB, NM23-H2 | NME/NM23 nucleoside diphosphate kinase 2 |
| NOS1 | nNOS, NOS | Nitric oxide synthase 1 (neuronal) |
| NOS2 | HEP-NOS, iNOS, NOS, NOS2A | Nitric oxide synthase 2, inducible |
| NOS3 | ECNOS, eNOS | Nitric oxide synthase 3 (endothelial cell) |
| NOTCH1 | TAN1 | Notch 1 |
| NOTCH2 | | Notch 2 |
| NOTCH3 | CADASIL, CASIL | Notch 3 |
| NQO1 | DHQU, DIA4, DTD, NMOR1, QR1 | NAD(P)H dehydrogenase, quinone 1 |
| NR0B1 | AHC, AHCH, DAX1, DSS, NR0B1 | Nuclear receptor subfamily 0, group B, member 1 |
| NRG1 | GGF, HGL, HRG, NDF, NRG1-IT2 | Neuregulin 1 |
| NRG2 | Don-1, HRG2, NTAK | Neuregulin 2 |
| NRG3 | | Neuregulin 3 |
| NRP1 | CD304, NRP, VEGF165R | Neuropilin 1 |
| NRP2 | VEGF165R2 | Neuropilin 2 |
| NTF3 | NGF2 | Neurotrophin 3 |
| NTF4 | GLC1O, NT-4/5, NTF5 | Neurotrophin 4 |
| NTHL1 | NTH1, OCTS3 | Nth endonuclease III-like 1 (*E. coli*) |
| NTN1 | NTN1L | Netrin 1 |
| NTRK1 | MTC, TRK, TRKA | Neurotrophic tyrosine kinase, receptor, type 1 |

TABLE 1-continued

| Gene | Gene synonym | Gene description |
| --- | --- | --- |
| NTRK2 | TRKB | Neurotrophic tyrosine kinase, receptor, type 2 |
| NTRK3 | TRKC | Neurotrophic tyrosine kinase, receptor, type 3 |
| NUDT1 | MTH1 | Nudix (nucleoside diphosphate linked moiety X)-type motif 1 |
| NUMB | C14orf41 | Numb homolog (*Drosophila*) |
| OGG1 | HMMH, HOGG1, MUTM, OGH1 | 8-oxoguanine DNA glycosylase |
| OR51E2 | PSGR | Olfactory receptor, family 51, subfamily E, member 2 |
| ORM1 | | Orosomucoid 1 |
| OSM | MGC20461 | Oncostatin M |
| PAGE4 | CT16.7, GAGEC1, PAGE-4 | P antigen family, member 4 (prostate associated) |
| PAPPA | ASBABP2, DIPLA1, IGFBP-4ase, PAPA, PAPP-A, PAPPA1 | Pregnancy-associated plasma protein A, pappalysin 1 |
| PARP1 | ADPRT, PARP, PPOL | Poly (ADP-ribose) polymerase 1 |
| PARVB | CGI-56 | Parvin, beta |
| PAX5 | BSAP | Paired box 5 |
| PAX8 | | Paired box 8 |
| PCNA | | Proliferating cell nuclear antigen |
| PDGFA | PDGF-A, PDGF1 | Platelet-derived growth factor alpha polypeptide |
| PDGFB | SIS, SSV | Platelet-derived growth factor beta polypeptide |
| PDGFRA | CD140a, PDGFR2 | Platelet-derived growth factor receptor, alpha polypeptide |
| PDGFRB | CD140b, JTK12, PDGFR, PDGFR1 | Platelet-derived growth factor receptor, beta polypeptide |
| PDZD4 | FLJ34125, KIAA1444, LU1, PDZK4, PDZRN4L | PDZ domain containing 4 |
| PF4 | CXCL4, SCYB4 | Platelet factor 4 |
| PGC | | Progastricsin (pepsinogen C) |
| PGF | D12S1900, PGFL, PLGF, PlGF-2, SHGC-10760 | Placental growth factor |
| PGR | NR3C3, PR | Progesterone receptor |
| PHF20 | C20orf104, dJ1121G12.1, TDRD20A | PHD finger protein 20 |
| PIGR | | Polymeric immunoglobulin receptor |
| PIK3CA | PI3K | Phosphatidylinositol-4,5-bisphosphate 3-kinase, catalytic subunit alpha |
| PIK3R1 | GRB1, p85, p85-ALPHA | Phosphoinositide-3-kinase, regulatory subunit 1 (alpha) |
| PIK3R2 | p85, P85B | Phosphoinositide-3-kinase, regulatory subunit 2 (beta) |
| PIK3R3 | p55 | Phosphoinositide-3-kinase, regulatory subunit 3 (gamma) |
| PIM1 | PIM | Pim-1 proto-oncogene, serine/threonine kinase |
| PIM2 | | Pim-2 proto-oncogene, serine/threonine kinase |
| PIM3 | | Pim-3 proto-oncogene, serine/threonine kinase |
| PIN1 | dod | Peptidylprolyl cis/trans isomerase, NIMA-interacting 1 |
| PIP4K2B | PIP5K2B, PIP5KIIB, PIP5KIIbeta | Phosphatidylinositol-5-phosphate 4-kinase, type II, beta |
| PKM | OIP3, PK3, PKM2, THBP1 | Pyruvate kinase, muscle |
| PLAT | | Plasminogen activator, tissue |
| PLAU | UPA, URK | Plasminogen activator, urokinase |
| PLAUR | CD87, UPAR, URKR | Plasminogen activator, urokinase receptor |
| PLG | | Plasminogen |
| PLK1 | PLK | Polo-like kinase 1 |
| PLP1 | GPM6C, PLP, SPG2 | Proteolipid protein 1 |
| PMEPA1 | STAG1, TMEPAI | Prostate transmembrane protein, androgen induced 1 |
| PML | MYL, RNF71, TRIM19 | Promyelocytic leukemia |
| PMP22 | GAS-3, HNPP, Sp110 | Peripheral myelin protein 22 |
| PNMT | PENT | Phenylethanolamine N-methyltransferase |
| POMC | ACTH, CLIP, LPH, MSH, NPP, POC | Proopiomelanocortin |
| PON1 | ESA, PON | Paraoxonase 1 |
| POSTN | OSF-2, periostin, PN | Periostin, osteoblast specific factor |
| POU2F2 | OCT2, OTF2 | POU class 2 homeobox 2 |

TABLE 1-continued

| Gene | Gene synonym | Gene description |
|---|---|---|
| PPA2 | FLJ20459 | Pyrophosphatase (inorganic) 2 |
| PPARG | NR1C3, PPARG1, PPARG2, PPARgamma | Peroxisome proliferator-activated receptor gamma |
| PPARGC1A | PGC1, PGC1A, PPARGC1 | Peroxisome proliferator-activated receptor gamma, coactivator 1 alpha |
| PPM1D | PP2C-DELTA, Wip1 | Protein phosphatase, Mg2+/Mn2+ dependent, 1D |
| PPP1R15A | GADD34 | Protein phosphatase 1, regulatory subunit 15A |
| PPY | PNP | Pancreatic polypeptide |
| PRDM13 | | PR domain containing 13 |
| PRDM16 | KIAA1675, MEL1, MGC166915, PFM13 | PR domain containing 16 |
| PRDX2 | MGC4104, NKEFB, PRP, PRX2, PRXII, TDPX1, TSA | Peroxiredoxin 2 |
| PRDX4 | AOE37-2 | Peroxiredoxin 4 |
| PRKCA | PKCA | Protein kinase C, alpha |
| PRKCB | PKCB, PRKCB1, PRKCB2 | Protein kinase C, beta |
| PRKCE | | Protein kinase C, epsilon |
| PRKCH | PKC-L, PKCL, PRKCL | Protein kinase C, eta |
| PRKCI | DXS1179E, PKCI | Protein kinase C, iota |
| PRKCQ | | Protein kinase C, theta |
| PRKDC | DNA-PKcs, DNAPK, DNPK1, HYRC, HYRC1, p350, XRCC7 | Protein kinase, DNA-activated, catalytic polypeptide |
| PRL | | Prolactin |
| PROC | | Protein C (inactivator of coagulation factors Va and VIIIa) |
| PRSS1 | TRY1 | Protease, serine, 1 (trypsin 1) |
| PSCA | | Prostate stem cell antigen |
| PSMD4 | AF, AF-1, Rpn10, S5A | Proteasome (prosome, macropain) 26S subunit, non-ATPase, 4 |
| PTCH1 | BCNS, NBCCS, PTCH | Patched 1 |
| PTCH2 | | Patched 2 |
| PTGS1 | COX1, PGHS-1, PTGHS | Prostaglandin-endoperoxide synthase 1 (prostaglandin G/H synthase and cyclooxygenase) |
| PTGS2 | COX2 | Prostaglandin-endoperoxide synthase 2 (prostaglandin G/H synthase and cyclooxygenase) |
| PTH | PTH1 | Parathyroid hormone |
| PTHLH | HHM, PLP, PTHR, PTHRP | Parathyroid hormone-like hormone |
| PTK2 | FADK, FAK, FAK1, PPP1R71 | Protein tyrosine kinase 2 |
| PTN | HBGF8, HBNF, NEGF1 | Pleiotrophin |
| PTPRO | GLEPP1, NPHS6, PTP-oc, PTP-U2, PTPU2 | Protein tyrosine phosphatase, receptor type, O |
| PTTG1 | EAP1, HPTTG, PTTG, securin, TUTR1 | Pituitary tumor-transforming 1 |
| PURA | PUR-ALPHA, PUR1, PURALPHA | Purine-rich element binding protein A |
| PZP | CPAMD6 | Pregnancy-zone protein |
| RAB11FIP3 | eferin, KIAA0665, Rab11-FIP3 | RAB11 family interacting protein 3 (class II) |
| RAB18 | | RAB18, member RAS oncogene family |
| RAB25 | CATX-8 | RAB25, member RAS oncogene family |
| RAC1 | p21-Rac1, Rac-1, TC-25 | Ras-related C3 botulinum toxin substrate 1 (rho family, small GTP binding protein Rac1) |
| RAD23A | HHR23A, MGC111083 | RAD23 homolog A (S. cerevisiae) |
| RAD23B | HHR23B, HR23B, P58 | RAD23 homolog B (S. cerevisiae) |
| RAD51 | BRCC5, HsRad51, HsT16930, RAD51A, RECA | RAD51 recombinase |
| RAD51D | HsTRAD, R51H3, RAD51L3, Trad | RAD51 paralog D |
| RAD52 | | RAD52 homolog (S. cerevisiae) |
| RAD54B | RDH54 | RAD54 homolog B (S. cerevisiae) |
| RAF1 | c-Raf, CRAF, Raf-1 | Raf-1 proto-oncogene, serine/threonine kinase |
| RARA | NR1B1, RAR | Retinoic acid receptor, alpha |
| RARB | HAP, NR1B2, RRB2 | Retinoic acid receptor, beta |
| RARG | NR1B3, RARC | Retinoic acid receptor, gamma |
| RASA1 | CM-AVM, GAP, p120GAP, p120RASGAP, RASA | RAS p21 protein activator (GTPase activating protein) 1 |

TABLE 1-continued

| Gene | Gene synonym | Gene description |
|---|---|---|
| RB1 | OSRC, PPP1R130, RB | Retinoblastoma 1 |
| RBBP4 | lin-53, NURF55, RbAp48 | Retinoblastoma binding protein 4 |
| RBL1 | cp107, p107, PRB1 | Retinoblastoma-like 1 |
| RBL2 | p130, Rb2 | Retinoblastoma-like 2 |
| RBM6 | 3G2, DEF-3, DEF3, g16, NY-LU-12 | RNA binding motif protein 6 |
| RBP4 | | Retinol binding protein 4, plasma |
| REL | c-Rel, I-Rel | V-rel avian reticuloendotheliosis viral oncogene homolog |
| RELA | NFKB3, p65 | V-rel avian reticuloendotheliosis viral oncogene homolog A |
| RELB | REL-B | V-rel avian reticuloendotheliosis viral oncogene homolog B |
| RET | CDHF12, CDHR16, HSCR1, MEN2A, MEN2B, MTC1, PTC, RET51 | Ret proto-oncogene |
| RHOA | ARH12, ARHA, Rho12, RhoA, RHOH12 | Ras homolog family member A |
| RHOB | ARH6, ARHB, MST081, RhoB, RHOH6 | Ras homolog family member B |
| RHOC | ARH9, ARHC, RhoC | Ras homolog family member C |
| RPA2 | | Replication protein A2, 32 kDa |
| RPL27 | L27 | Ribosomal protein L27 |
| RPS3 | FLJ26283, FLJ27450, MGC87870, S3 | Ribosomal protein S3 |
| RPS6KA1 | HU-1, RSK, RSK1 | Ribosomal protein S6 kinase, 90 kDa, polypeptide 1 |
| RPS6KA3 | CLS, HU-3, MRX19, RSK, RSK2 | Ribosomal protein S6 kinase, 90 kDa, polypeptide 3 |
| RXRA | NR2B1 | Retinoid X receptor, alpha |
| RXRB | H-2RIIBP, NR2B2, RCoR-1 | Retinoid X receptor, beta |
| RXRG | NR2B3 | Retinoid X receptor, gamma |
| S100A1 | S100-alpha, S100A | S100 calcium binding protein A1 |
| S100A2 | CAN19, S100L | S100 calcium binding protein A2 |
| S100A4 | 18A2, 42A, CAPL, FSP1, MTS1, P9KA, PEL98 | S100 calcium binding protein A4 |
| S100A6 | 2A9, CABP, CACY, PRA | S100 calcium binding protein A6 |
| S100A7 | PSOR1, S100A7c | S100 calcium binding protein A7 |
| S100A8 | 60B8AG, CAGA, CFAG, CGLA, MRP8, P8 | S100 calcium binding protein A8 |
| S100A9 | 60B8AG, CAGB, CFAG, CGLB, LIAG, MAC387, MIF, MRP14, NIF, P14 | S100 calcium binding protein A9 |
| S100B | S100beta | S100 calcium binding protein B |
| S1PR1 | CD363, D1S3362, edg-1, EDG1 | Sphingosine-1-phosphate receptor 1 |
| SAA1 | PIG4, SAA, TP53I4 | Serum amyloid A1 |
| SAA2 | | Serum amyloid A2 |
| SART1 | Ara1, SNRNP110, Snu66 | Squamous cell carcinoma antigen recognized by T cells |
| SCGB1A1 | CC10, CC16, CCSP, UGB | Secretoglobin, family 1A, member 1 (uteroglobin) |
| SCGB1D2 | LIPB, LPHB | Secretoglobin, family 1D, member 2 |
| SCGB2A1 | LPHC, MGB2, MGC71973, UGB3 | Secretoglobin, family 2A, member 1 |
| SCGB2A2 | MGB1, MGC71974, UGB2 | Secretoglobin, family 2A, member 2 |
| SDC1 | CD138, SDC, SYND1, syndecan | Syndecan 1 |
| SELE | CD62E, ELAM, ELAM1, ESEL | Selectin E |
| SELL | CD62L, hLHRc, LAM-1, LAM1, Leu-8, LNHR, LSEL, Lyam-1, LYAM1, PLNHR | Selectin L |
| SELP | CD62, CD62P, GMP140, GRMP, PADGEM, PSEL | Selectin P (granule membrane protein 140 kDa, antigen CD62) |
| SEMA3B | LUCA-1, SemA, sema5, SEMAA, semaV | Sema domain, immunoglobulin domain (Ig), short basic domain, secreted, (semaphorin) 3B |
| 2-Sep | DIFF6, hNedd5, KIAA0158, NEDD5, Pnutl3 | Septin 2 |
| SERPINA1 | A1A, A1AT, AAT, alpha-1-antitrypsin, alpha1AT, PI, PI1 | Serpin peptidase inhibitor, clade A (alpha-1 antiproteinase, antitrypsin), member 1 |
| SERPINA3 | AACT, ACT, alpha-1-antichymotrypsin | Serpin peptidase inhibitor, clade A (alpha-1 antiproteinase, antitrypsin), member 3 |

TABLE 1-continued

| Gene | Gene synonym | Gene description |
|---|---|---|
| SERPINA5 | PAI3, PCI, PLANH3, PROCI | Serpin peptidase inhibitor, clade A (alpha-1 antiproteinase, antitrypsin), member 5 |
| SERPINB2 | HsT1201, PAI2, PLANH2 | Serpin peptidase inhibitor, clade B (ovalbumin), member 2 |
| SERPINB3 | HsT1196, SCC, SCCA1, T4-A | Serpin peptidase inhibitor, clade B (ovalbumin), member 3 |
| SERPINB4 | LEUPIN, PI11, SCCA-2, SCCA1, SCCA2 | Serpin peptidase inhibitor, clade B (ovalbumin), member 4 |
| SERPINE1 | PAI, PAI1, PLANH1 | Serpin peptidase inhibitor, clade E (nexin, plasminogen activator inhibitor type 1), member 1 |
| SERPINF1 | EPC-1, PEDF, PIG35 | Serpin peptidase inhibitor, clade F (alpha-2 antiplasmin, pigment epithelium derived factor), member 1 |
| SFN | YWHAS | Stratifin |
| SHBG | ABP, MGC126834, MGC138391, TEBG | Sex hormone-binding globulin |
| SIRT2 | SIR2L | Sirtuin 2 |
| SKP2 | FBL1, FBXL1, p45 | S-phase kinase-associated protein 2, E3 ubiquitin protein ligase |
| SLC19A1 | FOLT | Solute carrier family 19 (folate transporter), member 1 |
| SLC2A1 | DYT18, GLUT, GLUT1, HTLVR | Solute carrier family 2 (facilitated glucose transporter), member 1 |
| SLC3A2 | 4F2, 4F2HC, 4T2HC, CD98, CD98HC, MDU1, NACAE | Solute carrier family 3 (amino acid transporter heavy chain), member 2 |
| SLPI | ALK1, ALP, BLPI, HUSI, HUSI-I, WAP4, WFDC4 | Secretory leukocyte peptidase inhibitor |
| SMAD1 | JV4-1, MADH1, MADR1 | SMAD family member 1 |
| SMAD2 | JV18-1, MADH2, MADR2 | SMAD family member 2 |
| SMAD3 | HsT17436, JV15-2, MADH3 | SMAD family member 3 |
| SMAD4 | DPC4, MADH4 | SMAD family member 4 |
| SMYD3 | KMT3E, ZMYND1, ZNFN3A1 | SET and MYND domain containing 3 |
| SOD1 | ALS, ALS1, IPOA | Superoxide dismutase 1, soluble |
| SOD2 | | Superoxide dismutase 2, mitochondrial |
| SOX1 | | SRY (sex determining region Y)-box 1 |
| SOX9 | CMD1, CMPD1, SRA1 | SRY (sex determining region Y)-box 9 |
| SP1 | | Sp1 transcription factor |
| SPARC | ON | Secreted protein, acidic, cysteine-rich (osteonectin) |
| SPARCL1 | MAST9 | SPARC-like 1 (hevin) |
| SPINK1 | PCTT, PSTI, Spink3, TATI | Serine peptidase inhibitor, Kazal type 1 |
| SPINT1 | HAI, MANSC2 | Serine peptidase inhibitor, Kunitz type 1 |
| SPINT2 | HAI-2, Kop | Serine peptidase inhibitor, Kunitz type, 2 |
| SPP1 | BNSP, BSPI, ETA-1, OPN | Secreted phosphoprotein 1 |
| SPRR1B | GADD33, SPRR1 | Small proline-rich protein 1B |
| SPRR3 | | Small proline-rich protein 3 |
| SPRY1 | hSPRY1 | Sprouty homolog 1, antagonist of FGF signaling (Drosophila) |
| SRC | ASV, c-src, SRC1 | SRC proto-oncogene, non-receptor tyrosine kinase |
| SRD5A1 | | Steroid-5-alpha-reductase, alpha polypeptide 1 (3-oxo-5 alpha-steroid delta 4-dehydrogenase alpha 1) |
| SRD5A2 | | Steroid-5-alpha-reductase, alpha polypeptide 2 (3-oxo-5 alpha-steroid delta 4-dehydrogenase alpha 2) |
| SST | SMST | Somatostatin |
| SSX2 | CT5.2a, HD21, HOM-MEL-40, MGC119055, MGC15364, MGC3884, SSX | Synovial sarcoma, X breakpoint 2 |
| SSX2B | CT5.2b | Synovial sarcoma, X breakpoint 2B |
| ST14 | HAI, MT-SP1, PRSS14, SNC19, TMPRSS14 | Suppression of tumorigenicity 14 (colon carcinoma) |
| STARD3 | es64, MLN64 | StAR-related lipid transfer (START) domain containing 3 |
| STAT4 | | Signal transducer and activator of transcription 4 |
| STAT5A | MGF, STAT5 | Signal transducer and activator of transcription 5A |

TABLE 1-continued

| Gene | Gene synonym | Gene description |
| --- | --- | --- |
| STEAP1 | PRSS24, STEAP | Six transmembrane epithelial antigen of the prostate 1 |
| STMN1 | C1orf215, FLJ32206, Lag, LAP18, OP18, PP17, PP19, PR22, SMN | Stathmin 1 |
| STRAP | MAWD, pt-wd, UNRIP | Serine/threonine kinase receptor associated protein |
| STT3A | ITM1, MGC9042, STT3-A, TMC | STT3A, subunit of the oligosaccharyltransferase complex (catalytic) |
| SULT1E1 | EST, STE | Sulfotransferase family 1E, estrogen-preferring, member 1 |
| TAGLN | DKFZp686P11128, SM22, SMCC, TAGLN1, WS3-10 | Transgelin |
| TDRD6 | bA446F17.4, CT41.2, NY-CO-45, SPATA36 | Tudor domain containing 6 |
| TEK | CD202b, TIE-2, TIE2, VMCM, VMCM1 | TEK tyrosine kinase, endothelial |
| TERT | EST2, hEST2, TCS1, TP2, TRT | Telomerase reverse transcriptase |
| TF | PRO1557, PRO2086 | Transferrin |
| TFAP2B | AP2-B | Transcription factor AP-2 beta (activating enhancer binding protein 2 beta) |
| TFDP1 | Dp-1, DP1, DRTF1 | Transcription factor Dp-1 |
| TFDP2 | Dp-2 | Transcription factor Dp-2 (E2F dimerization partner 2) |
| TFF1 | BCEI, D21S21, HP1.A, HPS2, pNR-2, pS2 | Trefoil factor 1 |
| TFF2 | SML1 | Trefoil factor 2 |
| TFF3 | HITF, ITF | Trefoil factor 3 (intestinal) |
| TFRC | CD71, p90, TFR1 | Transferrin receptor |
| TG | AITD3, TGN | Thyroglobulin |
| TGFA |  | Transforming growth factor, alpha |
| TGFB1 | CED, DPD1, TGFB, TGFbeta | Transforming growth factor, beta 1 |
| TGFB2 |  | Transforming growth factor, beta 2 |
| TGFB3 | ARVD, ARVD1 | Transforming growth factor, beta 3 |
| TGFBR3 | betaglycan, BGCAN | Transforming growth factor, beta receptor III |
| TGM4 | TGP | Transglutaminase 4 |
| TGM7 | TGMZ | Transglutaminase 7 |
| THBS1 | THBS, THBS-1, TSP, TSP-1, TSP1 | Thrombospondin 1 |
| THBS2 | TSP2 | Thrombospondin 2 |
| THBS4 |  | Thrombospondin 4 |
| THPO | MGDF, MPLLG, TPO | Thrombopoietin |
| THRA | AR7, EAR-7.1/EAR-7.2, ERBA, ERBA1, NR1A1, THRA1, THRA2, THRA3 | Thyroid hormone receptor, alpha |
| THRB | ERBA-BETA, ERBA2, GRTH, NR1A2, PRTH, THR1, THRB1, THRB2 | Thyroid hormone receptor, beta |
| TIE1 | JTK14, TIE | Tyrosine kinase with immunoglobulin-like and EGF-like domains 1 |
| TIMP1 | CLGI, EPO, TIMP | TIMP metallopeptidase inhibitor 1 |
| TIMP2 | CSC-21K | TIMP metallopeptidase inhibitor 2 |
| TIMP3 | SFD | TIMP metallopeptidase inhibitor 3 |
| TK1 |  | Thymidine kinase 1, soluble |
| TMF1 | ARA160, TMF | TATA element modulatory factor 1 |
| TMPRSS2 | PRSS10 | Transmembrane protease, serine 2 |
| TMPRSS3 | DFNB10, DFNB8 | Transmembrane protease, serine 3 |
| TNC | DFNA56, HXB, MGC167029, TN | Tenascin C |
| TNF | DIF, TNF-alpha, TNFA, TNFSF2 | Tumor necrosis factor |
| TNFAIP2 | B94, EXOC3L3 | Tumor necrosis factor, alpha-induced protein 2 |
| TNFAIP3 | A20, OTUD7C | Tumor necrosis factor, alpha-induced protein 3 |
| TNFRSF10A | Apo2, CD261, DR4, TRAILR-1 | Tumor necrosis factor receptor superfamily, member 10a |
| TNFRSF10B | CD262, DR5, KILLER, TRAIL-R2, TRICK2A, TRICKB | Tumor necrosis factor receptor superfamily, member 10b |
| TNFRSF10C | CD263, DcR1, LIT, TRAILR3, TRID | Tumor necrosis factor receptor superfamily, member 10c, decoy without an intracellular domain |

TABLE 1-continued

| Gene | Gene synonym | Gene description |
|---|---|---|
| TNFRSF10D | CD264, DcR2, TRAILR4, TRUNDD | Tumor necrosis factor receptor superfamily, member 10d, decoy with truncated death domain |
| TNFRSF11B | OCIF, OPG, TR1 | Tumor necrosis factor receptor superfamily, member 11b |
| TNFRSF12A | CD266, FN14, TweakR | Tumor necrosis factor receptor superfamily, member 12A |
| TNFRSF14 | ATAR, CD270, HVEA, HVEM, LIGHTR, TR2 | Tumor necrosis factor receptor superfamily, member 14 |
| TNFRSF1A | CD120a, TNF-R, TNF-R-I, TNF-R55, TNFAR, TNFR1, TNFR60 | Tumor necrosis factor receptor superfamily, member 1A |
| TNFRSF1B | CD120b, p75, TNF-R-II, TNF-R75, TNFBR, TNFR2, TNFR80 | Tumor necrosis factor receptor superfamily, member 1B |
| TNFRSF4 | ACT35, CD134, OX40, TXGP1L | Tumor necrosis factor receptor superfamily, member 4 |
| TNFRSF8 | CD30, D1S166E, KI-1 | Tumor necrosis factor receptor superfamily, member 8 |
| TNFRSF9 | 4-1BB, CD137, ILA | Tumor necrosis factor receptor superfamily, member 9 |
| TNFSF10 | Apo-2L, CD253, TL2, TRAIL | Tumor necrosis factor (ligand) superfamily, member 10 |
| TNFSF11 | CD254, ODF, OPGL, RANKL, TRANCE | Tumor necrosis factor (ligand) superfamily, member 11 |
| TNFSF13 | APRIL, CD256 | Tumor necrosis factor (ligand) superfamily, member 13 |
| TNFSF13B | BAFF, BLYS, CD257, TALL-1, TALL1, THANK, TNFSF20 | Tumor necrosis factor (ligand) superfamily, member 13b |
| TNFSF4 | CD252, gp34, OX-40L, TXGP1 | Tumor necrosis factor (ligand) superfamily, member 4 |
| TNFSF8 | CD153, CD30LG | Tumor necrosis factor (ligand) superfamily, member 8 |
| TNK2 | ACK, ACK1, p21cdc42Hs | Tyrosine kinase, non-receptor, 2 |
| TOP2A | TOP2 | Topoisomerase (DNA) II alpha 170 kDa |
| TP53 | LFS1, p53 | Tumor protein p53 |
| TP53BP2 | 53BP2, ASPP2, PPP1R13A | Tumor protein p53 binding protein 2 |
| TPD52 | D52, hD52, N8L | Tumor protein D52 |
| TPI1 | | Triosephosphate isomerase 1 |
| TPM1 | C15orf13, CMH3 | Tropomyosin 1 (alpha) |
| TPM2 | AMCD1, DA1, NEM4 | Tropomyosin 2 (beta) |
| TPX2 | C20orf1, C20orf2, DIL-2, p100 | TPX2, microtubule-associated |
| TRAF1 | EBI6 | TNF receptor-associated factor 1 |
| TRAF2 | TRAP3 | TNF receptor-associated factor 2 |
| TRAF4 | CART1, MLN62, RNF83 | TNF receptor-associated factor 4 |
| TRIM25 | EFP, RNF147, ZNF147 | Tripartite motif containing 25 |
| TRIP4 | HsT17391, ZC2HC5 | Thyroid hormone receptor interactor 4 |
| TRO | KIAA1114, MAGE-D3, MAGED3 | Trophinin |
| TSG101 | TSG10, VPS23 | Tumor susceptibility 101 |
| TSPAN8 | CO-029, TM4SF3 | Tetraspanin 8 |
| TSPO | BZRP, DBI, IBP, MBR, mDRC, PBR, pk18, PKBS | Translocator protein (18 kDa) |
| TTR | CTS, CTS1, HsT2651, PALB | Transthyretin |
| TUSC2 | C3orf11, FUS1, PAP, PDAP2 | Tumor suppressor candidate 2 |
| TWIST1 | ACS3, bHLHa38, BPES2, BPES3, CRS, CRS1, H-twist, SCS, TWIST | Twist family bHLH transcription factor 1 |
| TXLNA | DKFZp451J0118 | Taxilin alpha |
| TYMP | ECGF1, MNGIE | Thymidine phosphorylase |
| TYMS | HsT422, TMS, TS, Tsase | Thymidylate synthetase |
| TYRO3 | Brt, Dtk, RSE, Sky, Tif | TYRO3 protein tyrosine kinase |
| UBA1 | A1S9T, CFAP124, GXP1, POC20, UBE1, UBE1X | Ubiquitin-like modifier activating enzyme 1 |
| UBE2C | UBCH10 | Ubiquitin-conjugating enzyme E2C |
| UBE2I | UBC9 | Ubiquitin-conjugating enzyme E2I |
| UBE2N | MGC8489, UBC13, UbcH-ben | Ubiquitin-conjugating enzyme E2N |
| UGT1A10 | UGT1J | UDP glucuronosyltransferase 1 family, polypeptide A10 |
| UGT1A3 | UGT1C | UDP glucuronosyltransferase 1 family, polypeptide A3 |
| UGT1A4 | HUG-BR2, UGT1D | UDP glucuronosyltransferase 1 family, polypeptide A4 |

TABLE 1-continued

| Gene | Gene synonym | Gene description |
| --- | --- | --- |
| UGT1A8 | UGT1H | UDP glucuronosyltransferase 1 family, polypeptide A8 |
| UGT1A9 | HLUGP4, LUGP4, UGT1AI | UDP glucuronosyltransferase 1 family, polypeptide A9 |
| USH1C | AIE-75, DFNB18, harmonin, NY-CO-37, NY-CO-38, PDZ-73, PDZ73, PDZD7C | Usher syndrome 1C (autosomal recessive, severe) |
| VAMP3 | CEB | Vesicle-associated membrane protein 3 |
| VCAM1 | CD106 | Vascular cell adhesion molecule 1 |
| VEGFA | VEGF, VEGF-A, VPF | Vascular endothelial growth factor A |
| VEGFB | VEGFL, VRF | Vascular endothelial growth factor B |
| VEGFC | VRP | Vascular endothelial growth factor C |
| VHL | VHL1 | Von Hippel-Lindau tumor suppressor, E3 ubiquitin protein ligase |
| VIL1 | D2S1471, VIL | Villin 1 |
| VIP | | Vasoactive intestinal peptide |
| VTN | VN | Vitronectin |
| VWF | F8VWF | Von Willebrand factor |
| WEE1 | | WEE1 G2 checkpoint kinase |
| WFDC2 | dJ461P17.6, EDDM4, HE4, WAP5 | WAP four-disulfide core domain 2 |
| WISP1 | CCN4 | WNT1 inducible signaling pathway protein 1 |
| WNT1 | INTI | Wingless-type MMTV integration site family, member 1 |
| WNT2 | INT1L1, IRP | Wingless-type MMTV integration site family member 2 |
| WRN | RECQ3, RECQL2 | Werner syndrome, RecQ helicase-like |
| WT1 | AWT1, GUD, WAGR, WIT-2 | Wilms tumor 1 |
| XBP1 | XBP2 | X-box binding protein 1 |
| XIAP | API3, BIRC4, hILP | X-linked inhibitor of apoptosis |
| XPA | XP1, XPAC | Xeroderma pigmentosum, complementation group A |
| XPC | RAD4, XPCC | Xeroderma pigmentosum, complementation group C |
| XRCC2 | | X-ray repair complementing defective repair in Chinese hamster cells 2 |
| XRCC3 | | X-ray repair complementing defective repair in Chinese hamster cells 3 |
| XRCC4 | | X-ray repair complementing defective repair in Chinese hamster cells 4 |
| XRCC5 | KARP-1, KU80, Ku86, KUB2 | X-ray repair complementing defective repair in Chinese hamster cells 5 (double-strand-break rejoining) |
| XRCC6 | D22S671, D22S731, G22P1, KU70, ML8 | X-ray repair complementing defective repair in Chinese hamster cells 6 |
| YBX1 | BP-8, CSDA2, CSDB, DBPB, MDR-NF1, NSEP-1, NSEP1, YB-1, YB1 | Y box binding protein 1 |
| YWHAB | YWHAA | Tyrosine 3-monooxygenase/tryptophan 5-monooxygenase activation protein, beta |
| YWHAE | FLJ45465 | Tyrosine 3-monooxygenase/tryptophan 5-monooxygenase activation protein, epsilon |
| YWHAH | YWHA1 | Tyrosine 3-monooxygenase/tryptophan 5-monooxygenase activation protein, eta |
| ZBTB16 | PLZF, ZNF145 | Zinc finger and BTB domain containing 16 |
| ZMAT3 | FLJ12296, MGC10613, PAG608, WIG-1, WIG1 | Zinc finger, matrin-type 3 |

In one embodiment, the biomarker is MYC. In one embodiment, the measurable aspect of MYC is its expression status. In one embodiment, the biomarker is overexpression of MYC.

Thus, in certain aspects of the disclosure, the biomarker is MYC which is differentially present in a subject of one phenotypic status, e.g., a patient having cancer, e.g., hepatocellular carcinoma (HCC), glioblastomas (GBM), lung cancer, breast cancer, head and neck cancer, prostate cancer, melanoma, or colorectal cancer, as compared with another phenotypic status, e.g., a normal undiseased subject or a patient having cancer without overexpression MYC.

Biomarker standards can be predetermined, determined concurrently, or determined after a biological sample is obtained from the subject. Biomarker standards for use with the methods described herein can, for example, include data from samples from subjects without cancer; data from samples from subjects with cancer, e.g., GBM, that is not a progressive, recurrent, and/or metastatic cancer; and data from samples from subjects with cancer, e.g., GBM, that is a progressive, recurrent, and/or metastatic cancer. Comparisons can be made to establish predetermined threshold biomarker standards for differenct classes of subjects, e.g., diseased vs. non-diseased subjects. The standards can be run in the same assay or can be known standards from a previous assay.

In one embodiment, the biomarker is MCL1. In one embodiment, the measurable aspect of MCL1 is its expression status. In one embodiment, the biomarker is overexpression of MCL1.

A biomarker is differentially present between different phenotypic status groups if the mean or median expression or mutation levels of the biomarker is calculated to be different, i.e., higher or lower, between the groups. Thus, biomarkers provide an indication that a subject, e.g., a cancer patient, belongs to one phenotypic status or another.

Thus, in certain aspects of the disclosure, the biomarker is MCL1 which is differentially present, i.e., overexpressed, in a subject of one phenotypic status, e.g., a patient having cancer, e.g., hepatocellular carcinoma (HCC), glioblastomas (GBM), lung cancer, breast cancer, head and neck cancer, prostate cancer, melanoma, colorectal cancer, medulloblastoma, or general brain tumors, as compared with another phenotypic status, e.g., an undiseased patient or a cancer patient without overexpression MCL1.

In addition to individual biological compounds, e.g., MYC or MCL1, the term "biomarker" as used herein is meant to include groups, sets, or arrays of multiple biological compounds. For example, the combination of MYC and MCL1 may comprise a biomarker. The term "biomarker" may comprise one, two, three, four, five, six, seven, eight, nine, ten, fifteen, twenty, twenty five, thirty, or more, biological compounds.

The determination of the expression level or mutation status of a biomarker in a patient can be performed using any of the many methods known in the art. Any method known in the art for quantitating specific proteins and/or detecting MYC and/or MCL1 expression, or the expression or mutation levels of any other biomarker in a patient or a biological sample may be used in the methods of the disclosure. Examples include, but are not limited to, PCR (polymerase chain reaction), or RT-PCR, Northern blot, Western blot, ELISA (enzyme linked immunosorbent assay), RIA (radioimmunoassay), gene chip analysis of RNA expression, immunohistochemistry or immunofluorescence. See, e.g., Slagle et al. Cancer 83:1401 (1998). Certain embodiments of the disclosure include methods wherein biomarker RNA expression (transcription) is determined. Other embodiments of the disclosure include methods wherein protein expression in the biological sample is determined. See, for example, Harlow et al., Antibodies: A Laboratory Manual, Cold Spring Harbor Laboratory, Cold Spring Harbor, N.Y., (1988) and Ausubel et al., Current Protocols in Molecular Biology, John Wiley & Sons, New York 3rd Edition, (1995). For northern blot or RT-PCR analysis, RNA is isolated from the tumor tissue sample using RNAse free techniques. Such techniques are commonly known in the art.

In one embodiment of the disclosure, a biological sample is obtained from the patient and cells in the biopsy are assayed for determination of biomarker expression or mutation status.

In one embodiment of the disclosure, PET imaging is used to determine biomarker expression.

In another embodiment of the disclosure, Northern blot analysis of biomarker transcription in a tumor cell sample is performed. Northern analysis is a standard method for detection and/or quantitation of mRNA levels in a sample.

Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is pre-hybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabled probes and their use are well known in the art. The presence and or relative levels of expression of the biomarker being assayed can be quantified using, for example, densitometry.

In another embodiment of the disclosure, biomarker expression and/or mutation status is determined using RT-PCR. RT-PCR allows detection of the progress of a PCR amplification of a target gene in real time. Design of the primers and probes required to detect expression and/or mutation status of a biomarker of the disclosure is within the skill of a practitioner of ordinary skill in the art. RT-PCR can be used to determine the level of RNA encoding a biomarker of the disclosure in a tumor tissue sample. In an embodiment of the disclosure, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., *Cold Spring Harbor Symp. Quant. Biol.* 51:263 (1986); EP 50,424; EP 84,796; EP 258,017; EP 237,362; EP 201,184; U.S. Pat. Nos. 4,683,202; 4,582,788; 4,683,194.

RT-PCR probes depend on the 5'-3' nuclease activity of the DNA polymerase used for PCR to hydrolyze an oligonucleotide that is hybridized to the target amplicon (biomarker gene). RT-PCR probes are oligonucleotides that have a fluorescent reporter dye attached to the 5, end and a quencher moiety coupled to the 3' end (or vice versa). These probes are designed to hybridize to an internal region of a PCR product. In the unhybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. This decouples the fluorescent and quenching dyes and FRET no longer occurs. Thus, fluorescence increases in each cycle, in a manner proportional to the amount of probe cleavage. Fluorescence signal emitted from the reaction can be measured or followed over time using equipment which is commercially available using routine and conventional techniques.

In another embodiment of the disclosure, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibodythat specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In another embodiment of the disclosure, the expression of a protein encoded by a biomarker is detected by enzyme-linked immunosorbent assay (ELISA). In one embodiment of the disclosure, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

In another embodiment of the disclosure, the expression of a biomarker is evaluated by use of a gene chip or microarray. Such techniques are within ordinary skill held in the art.

VI. Definitions

The disclosure provides various therapeutic methods, kits, and pharmaceutical compositions comprising TG02. The term "TG02" as used herein refers to (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene in any crystalline or amorphous form as a free base or as a pharmaceutically acceptable salt or solvate. In one embodiment, TG02 refers to the free base of (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene. In another embodiment, TG02 refers to a pharmaceutically acceptable salt of (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene. A pharmaceutically acceptable salt of TG02 can be prepared during the final isolation and purification of TG02 or separately by reacting TG02 with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of TG02 include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts.

In another embodiment, TG02 refers to the citrate salt of (16E)-14-methyl-20-oxa-5,7,14,26-tetraazatetracyclo [19.3.1.1(2,6).1(8,12)]heptacosa-1(25),2(26),3,5,8(27),9,11,16,21,23-decaene. This is referred to as TG02 citrate or (16E)-14-methyl-20-oxa-5,7,14,26-tetraazatetracyclo [19.3.1.1(2,6). 1(8,12)]heptacosa-1(25),2(26),3,5,8(27),9,11,16,21,23-decaene—citric acid.

The term "biological sample" as used herein refers any tissue or fluid from a patient that is suitable for detecting a biomarker, such as MYC and/or MCL1 expression status. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practioner. In one embodiment of the disclosure, the biological sample comprises blood cells.

The terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language, e.g., "such as," provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. However, in one embodiment, administration of TG02 and/or an immune checkpoint inhibitor and/or COX-2 inhibitor leads to complete remission of the cancer.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that causes a therapeutic response, e.g., normalization of blood counts, decrease in the rate of tumor growth, decrease in tumor mass, decrease in the number of metastases, increase in time to tumor progression, and/or increase patient survival time by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or more.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, TG02 can be administered at the same time or sequentially in any order at different points in time as the immune checkpoint inhibitor and/or the COX-2 inhibitor and/or the optional therapeutic agent. TG02 and the immune checkpoint inhibitor and/or the COX-2 inhibitor and/or the optional therapeutic agent can be administered separately, in any appropriate form and by any suitable route. When TG02 and the immune checkpoint inhibitor and/or the COX-2 inhibitor and/or the optional therapeutic agent are not administered concurrently, it is understood that they can be administered in any order to a patient in need thereof. For example, TG02 can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the immune checkpoint inhibitor and/or COX-2 inhibitor, to an individual in need thereof. In various embodiments, TG02 and the immune checkpoint inhibitor and/or COX-2 inhibitor are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart. In one embodiument, TG02 is administered 3-7 days prior to the day the immune checkpoint inhibitor is administered. In another embodiment, TG02 is also administered on the day the immune checkpoint inhibitor is administered and continues to be administered until disease progression or TG02 therapy is no longer beneficial.

EXAMPLES

Example 1

This study is being done to compare progression-free or overall survival using pembrolizumab (p) or nivolumab (n) to p or n in combination with TG02 for participants with cancer who are untreated or have progressed after prior therapy and who have been selected for overexpressed MYC and/or MCL1 status. Participants will be randomized to receive either standard anti-PD-1 therapy plus placebo or standard anti-PD-1 therapy plus TG02.

Primary Outcome Measures: Progression-free-survival (PFS) and/or Overall survival (OS)

Secondary Outcome Measures: Overall response rate (ORR) and/or Response Duration Eligibility
  Ages Eligible for Study: Generally—18 Years and older
    For medulloblastoma patients—6 months or older
  Genders Eligible for Study: Both
Inclusion Criteria:
  Histologically or cytologically confirmed diagnosis of cancer not amenable to local therapy
  Must consent to allow correlative studies; must provide a newly obtained tissue/biopsy specimen (or specimen obtained within 60 days of consenting)
  Radiographically measurable disease
  Eastern Cooperative Oncology Group Performance Status of 0 or 1
  Patient has disease with overexpressed MYC and/or MCL1
Exclusion Criteria:
  Chemotherapy, radiation therapy, or biological therapy within four weeks prior to the first dose of study drug, or not recovered from the AEs due to cancer therapies administered more than four weeks earlier
  Participating or has participated in a study of an investigational agent or using an investigational device within 30 days of the first dose of study drug
  Expected to require any other form of systemic or localized antineoplastic therapy while on study
  Chronic systemic steroid therapy within two weeks before the planned date for first dose randomized treatment or on any other form of immunosuppressive medication
  Known history of any other than the current malignancy excepting adequately treated basal or squamous cell carcinoma of the skin, superficial bladder cancer, in situ cervical cancer, breast cancer, or other in situ cancers
  Known active central nervous system (CNS) metastases and/or carcinomatous meningitis
  Active autoimmune disease or a documented history of autoimmune disease or syndrome that requires systemic steroids or immunosuppressive agents
  Prior treatment with any other anti-programmed cell death (PD) agent
  Active infection requiring systemic therapy
  Known history of Human Immunodeficiency Virus (HIV)
  Active Hepatitis B or Hepatitis C
  Regular user (including recreational use of) illicit drugs or had a recent history (within the last year) of substance abuse (including alcohol)
  Pregnant or breastfeeding, or expecting to conceive or father children within the projected duration of the study.
Protocols:
  A first group of patients receive 2-10 mg/kg pembrolizumab (or flat dose equivalent) administered by intravenous infusion every three weeks and TG02 administered orally at 100, 200 or 300 mg once daily until disease progression or is no longer beneficial. TG02 administration is started 3-7 days prior to initiating pembrolizumab therapy, continues on the day of pembrolizumab administration, and continues until disease progression or until TG02 therapy is no longer beneficial. The control patients receive 2-10 mg/kg pembrolizumab (or flat dose equivalent) administered by intravenous infusion every three weeks.

A second group of patients receive 3 mg/kg nivolumab administered over 60 minutes by intravenous infusion every 2 weeks and TG02 administered orally at 100, 200, or 300 mg once daily. TG02 administration is started 3-7 days prior to initiating nivolumab therapy, continues on the day of nivolumab administration, and continues until disease progression or until TG02 therapy is no longer beneficial. The control patients receive 3 mg/kg nivolumab administered over 60 minutes by intravenous infusion every 2 weeks.

Results:

TG02 in combination with pembrolizumab or nivolumab results in better antitumor clinical activity than the immune checkpoint inhibitors alone in patients whose tumors overexpress MYC and/or MCL1. Unexpected objective responses are obtained associated with lack of tumor progression and extension of long term survival compared to historical controls using (the antibody) alone. In one embodiment, patients receiving TG02 and the immune checkpoint inhibitor achieve an extension of time to progression (or progression-free survival) of at least 2 months, at least 4 months, at least 6 months, at least 8 months, at least 10 months or at least 12 months. In another embodiment, at least some of the patients receiving TG02 and the immune checkpoint inhibitor achieve an extension of duration of response of at least 2 months, at least 4 months, at least 6 months, at least 8 months, at least 10 months or at least 12 months.

Example 2

Open label Phase 2 study assessing the combination of checkpoint blockade immunotherapy and TG02 in patients relapsing from or refractory to standard anti-PD-1 therapy (p) or (n).

Primary endpoint: ORR
Secondary endpoints: PFS, OS, Duration of Response, Safety Inclusion Criteria:
Histologically confirmed diagnosis of cancer not amenable to local therapy
Eastern Cooperative Oncology Group (ECOG) performance status of 0 or 1
At least one measurable lesion
Adequate organ function
Prior therapy with an anti-PD-1 or anti-PD-L1 antibody
Patient has disease with overexpressed MYC and/or MCL1

Exclusion Criteria:
Chemotherapy, targeted small molecule therapy, radiotherapy, or biological cancer therapy (including monoclonal antibodies) within 4 weeks prior to the first dose of trial treatment, or not recovered (<=Grade 1 or baseline) from adverse events due to a previously administered agent.
Expected to require any other form of systemic or localized antineoplastic therapy while in study.
Known active central nervous system (CNS) metastases and/or carcinomatous meningitis.
Documented history of clinically severe autoimmune disease, or a syndrome that requires systemic steroids or immunosuppressive agents.
Receiving systemic steroid therapy or any other form of immunosuppressive therapy within 1 week prior to the first dose of study treatment.
Received a live vaccine within 4 weeks prior to the first dose of trial treatment.
History or evidence of active pneumonitis.
Human immunodeficiency virus (HIV)-positive.
Active Hepatitis B or C.
Pregnant, breastfeeding, or expecting to conceive or father children within the projected duration of the trial treatment through 120 days after the last dose of study medication.

Dosing Protocol:

TABLE 1

TG02 + Checkpoint Inhibitor Combination Dosing & Schedules

|  | Every 2 weeks | Every 3 weeks | Every 4 weeks |
| --- | --- | --- | --- |
| Pembrolizumab 2 mg/kg | X | X |  |
| Pembrolizumab 10 mg/kg | X | X |  |
| Pembrolizumab 200 mg | X | X |  |
| Pembrolizumab 300 mg | X | X |  |
| Nivolumab 3 mg/kg | X | X | X |
| Nivolumab 1 mg/kg | X | X | X |
| Pidilizumab 3 mg/kg | X | X | X |
| Pidilizumab 1.5 mg/kg | X | X | X |
| STI-110 2 mg/kg | X | X | X |
| STI-110 2 mg/kg | X | X | X |
| Durvalumab 10 mg/kg | X | X |  |
| Durvalumab 2 mg/kg | X | X |  |
| Durvalumab 15, g/kg |  | X | X |
| Avelumab 1200 mg | X | X | X |
| Avelumab 10 mg/kg | X | X | X |
| Avelumab 5 mg/kg | X | X | X |
| Atezolizumab 1200 mg |  | X |  |
| STI-1014 10 mg/kg | X | X | X |
| STI-1014 15 mg/kg | X | X | X |

*TG02 is dosed weekly (50-400 mg) starting at least 5 days prior to initiating checkpoint inhibitor therapy and continuing until disease progression or investigator decision Results Combining TG02 with at least one checkpoint inhibitor in patients with overexpressed MYC and/or MCL1 tumors reverses immune evasion and induces clinically relevant responses in patients previously nonresponding to or failing checkpoint inhibitor therapy or de novo cancer patients. Unexpected objective responses are obtained associated with lack of tumor progression and extension of long term survival compared to historical controls using (the antibody) alone. In one embodiment, patients receiving TG02 and at least one immune checkpoint inhibitor achieve an extension of time to progression (or progression-free survival) of at least 2 months, at least 4 months, at least 6 months, at least 8 months, at least 10 months or at least 12 months. In another embodiment, at least some of the patients receiving TG02 and at least one immune checkpoint inhibitor achieve an extension of duration of response of at least 2 months, at least 4 months, at least 6 months, at least 8 months, at least 10 months or at least 12 months.

Example 3

Placebo-Controlled, Randomized Phase 2 Study of Pembrolizumab+TG02 vs. Pembrolizumab+Placebo in Participants with Previously-Treated Locally Advanced Unresectable or Metastatic Colorectal Cancer Exhibiting Overexpressed MYC and/or MCL1 Status Primary Endpoint: PFS
Secondary Endpoint: ORR, Duration of Response
Inclusion Criteria:
Histologically-proven locally advanced unresectable or metastatic high colorectal carcinoma Previously treated with at least two lines of approved standard therapies, which must include fluoropyrimidine, oxaliplatin, irinotecan, bevacizumab, and cetuximab or panitumumab Eastern Cooperative Oncology Group performance status of 0 or 1

Patient has disease with overexpressed MYC and/or MCL1

Life expectancy of greater than 3 months

At least one measureable lesion

Female participants of childbearing potential should be willing to use 2 methods of birth control or be surgically sterile, or abstain from heterosexual activity for the course of the study through 120 days after the last dose of study medication Male participants should agree to use an adequate method of contraception starting with the first dose of study therapy through 120 days after the last dose of study medication Adequate organ function Exclusion Criteria:

Currently participating in another study and receiving trial treatment, participated in a study of an investigational agent and received trial treatment within 4 weeks of the first dose of medication in this study, or used an investigational device within 4 weeks of the first dose of medication in this study Active autoimmune disease that has required systemic treatment in past 2 years Diagnosis of immunodeficiency or receiving systemic steroid therapy or any other form of immunosuppressive therapy within 7 days prior to the first dose of study medication Known active central nervous system (CNS) metastases and/or carcinomatous meningitis Prior monoclonal antibody (mAb), chemotherapy, targeted small molecule therapy, or radiation therapy within 2 weeks prior to study Day 1 or not recovered (i.e., Grade 1 or at baseline) from adverse events due to a previously administered agent Prior therapy with an anti-programmed cell death (PD)-1, anti-PD-L1, or anti-PD-L2 agent, or participant has previously participated in Merck pembrolizumab (MK-3475) clinical trial Known additional malignancy that is progressing or requires active treatment with the exception of basal cell carcinoma of the skin or squamous cell carcinoma of the skin that has undergone potentially curative therapy, or in situ cervical cancer Received a live vaccine within 30 days of planned start of study medication Known history of human immunodeficiency virus (HIV)

Known active Hepatitis B or C

Known history or any evidence of interstitial lung disease or active, non-infectious pneumonitis Active infection requiring systemic therapy Known psychiatric or substance abuse disorders that would interfere with cooperation with the requirements of the trial Pregnant or breastfeeding, or expecting to conceive or father children within the projected duration of the trial, starting with the screening visit through 120 days after the last dose of trial medication Dosing Protocol:

Patients receive 2-10 mg/kg pembrolizumab administered by intravenous infusion every three weeks and TG02 administered orally at 1, 2 or 3 mg/kg 3-7 days prior to pembrolizumab administration, on the day of pembrolizumab administration, and continuously thereafter until disease progression or until it is no longer beneficial. The control patients receive 2 mg/kg pembrolizumab administered by intravenous infusion every three weeks.

Results:

When used in patients with tumors overexpressing MYC and/or MCL1, TG02 combined with pembrolizumab provides superior clinical activity than pembrolizumab alone in the same patients. Unexpected objective responses are obtained in patients associated with lack of tumor progression and extension of long term survival compared to historical controls using (the antibody) alone. In one embodiment, patients receiving TG02 and pembrolizumab achieve an extension of time to progression (or progression-free survival) of at least 2 months, at least 4 months, at least 6 months, at least 8 months, at least 10 months or at least 12 months. In another embodiment, at least some of the patients receiving TG02 and pembrolizumab achieve an extension of duration of response of at least 2 months, at least 4 months, at least 6 months, at least 8 months, at least 10 months or at least 12 months.

Example 4

TG02 in Combination with Carfilzomib in Carfilzomib (CFZ) Refractory Multiple Myeloma (MM) Patients Methods An open-label Phase 1b study enrolled MM patients that previously received ≥2 lines of therapy. The primary objective was to determine the maximum tolerated dose (MTD) of TG02 in combination with carfilzomib (TG02/CFZ). Secondary objectives included anti-tumor activity and safety. TG02 was administered once daily on days 1, 4, 8, 11, 15, 18 of a 28-day schedule (BIW). The TG02 starting dose was 150 mg. TG02 dosing was escalated in 50 mg increments up to 300 mg. CFZ was dosed according to the Prescribing Information. Responses were assessed using standard criteria.

Results

Fourteen patients were enrolled for dose escalation and 10 patients were enrolled for the MTD cohort expansion. Patients were heavily pretreated: median 6 previous treatments [min 3; max 15] and 92% patients received CFZ in a prior regimen. The best response to previous therapy was progressive disease in 46% patients. The MTD was 250 mg TG02 combined with CFZ. Two dose-limiting toxicities were observed (including Grade (Gr) 4 sepsis and Gr 4 neutropenia), both on the 300 mg cohort. The most common drug-related adverse events (AEs) were diarrhea (Gr 1-2: 71% Gr 3: 17%), nausea (Gr 1-2: 79%), vomiting (Gr 1-2: 50%), fatigue (Gr 1-2: 38%, Gr 3: 4%), anorexia (Gr 1: 21%), anemia (Gr 1-2: 4%, Gr 3: 17%) and thrombocytopenia (Gr 3: 8%, Gr 4: 13%). Six patients (25%) discontinued treatment due to an AE. Serious AEs occurred in 50% patients; only acute renal failure and febrile neutropenia occurred in >1 pt (8% each). The severity of AEs was similar to single agent TG02. The incidence of diarrhea was increased in the TG02/CFZ administration (88% vs 67%) but the incidence of other AEs was similar to single agent TG02. Fourteen patients administered TG02 at the MTD were evaluable for response. The overall response rate (≥PR) was 27%; the clinical benefit rate (≥MR) was 45% (1 very good partial response, 2 partial response and 2 minimal response). All responders (MR or better) were CFZ-refractory in a previous treatment regimen. Durable stable disease was observed in 27% patients.

Conclusion

The safety profile of TG02 BIW/CFZ was similar to that of TG02 alone. The most common drug-related AEs were diarrhea, nausea, and vomiting; grade 4 AEs were infrequent. Objective responses were observed in CFZ-refractory patients.

Example 5

TG02 Activity in Glioma Cells and Allograft Model

Figure 2:
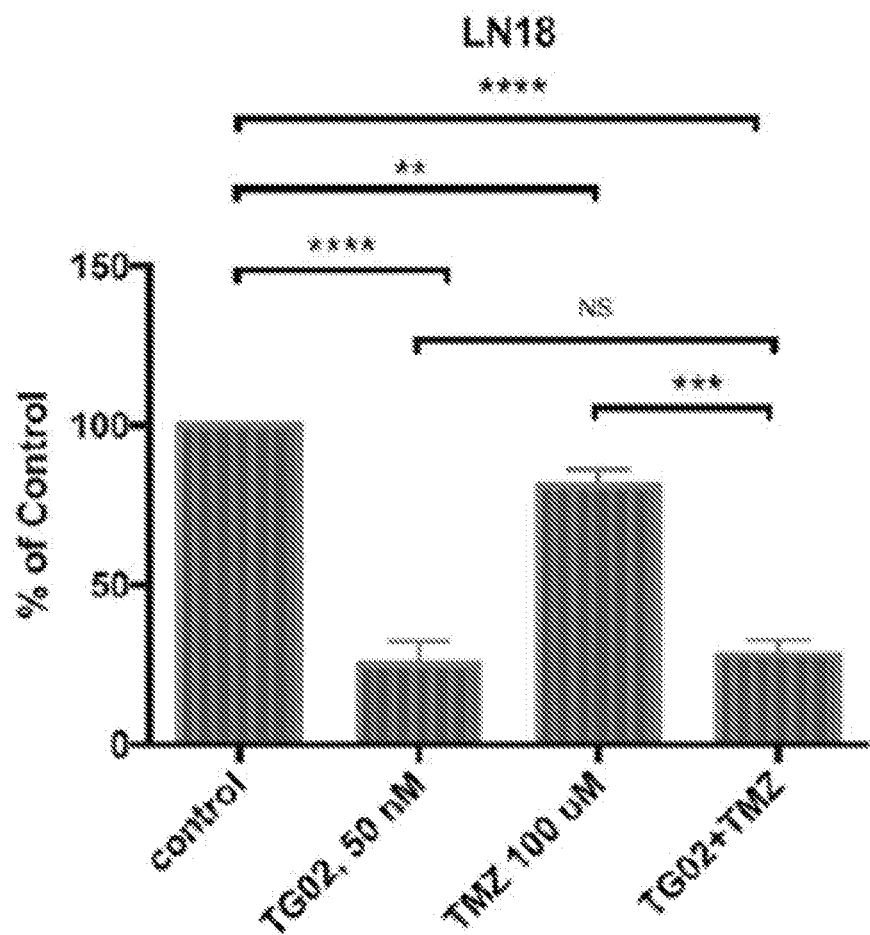
FIG. 2 is a bar graph showing the in vitro activity of TG02, TMZ, and TG02+TMZ in LN18 cells.
Figure 3:
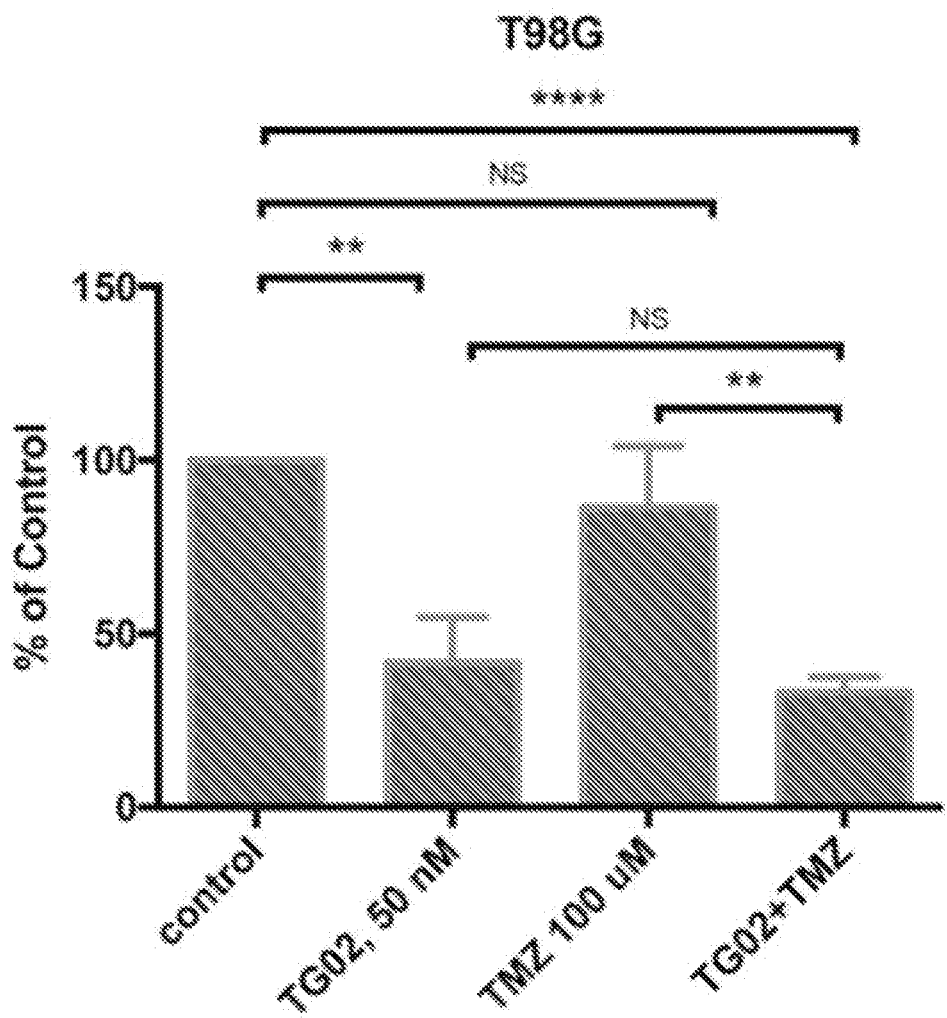
FIG. 3 is a bar graph showing the in vitro activity of TG02, TMZ, and TG02+TMZ in T98G cells.
Figure 4:
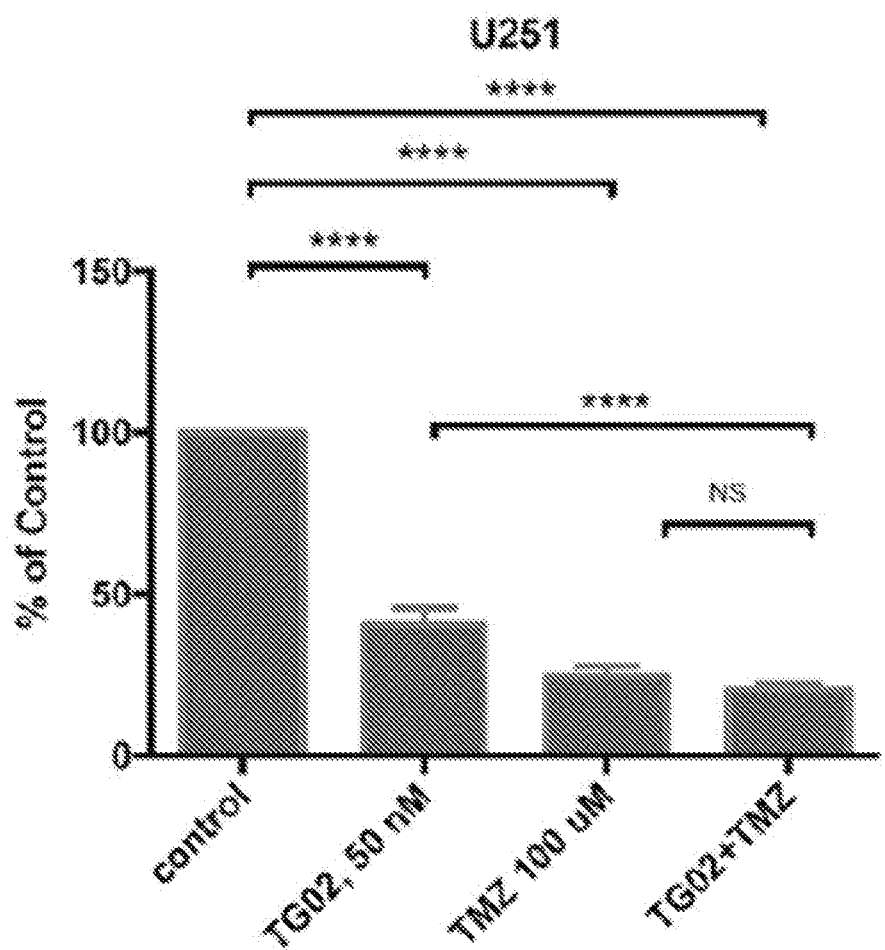
FIG. 4 is a bar graph showing the in vitro activity of TG02, TMZ, and TG02+TMZ in U251 cells.
Figure 5:
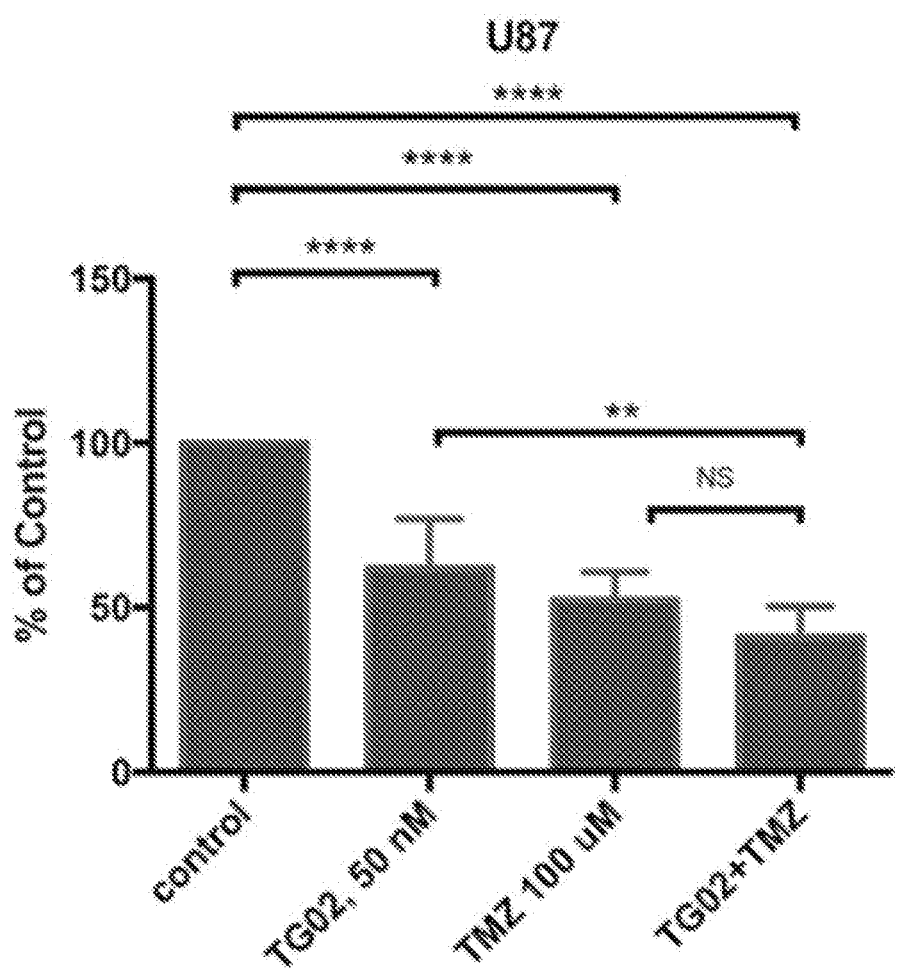
FIG. 5 is a bar graph showing the in vitro activity of TG02, TMZ, and TG02+TMZ in U87 cells.
Figure 6:
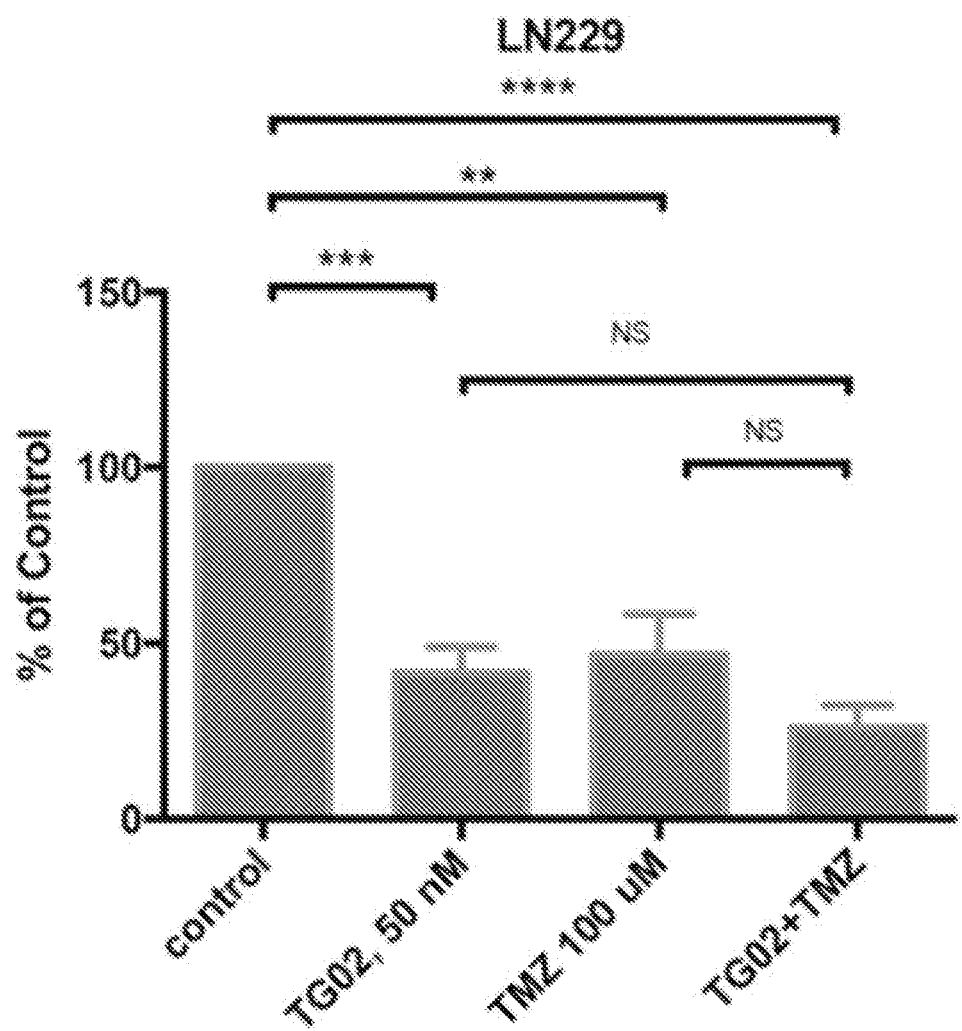
FIG. 6 is a bar graph showing the in vitro activity of TG02, TMZ, and TG02+TMZ in LN299 cells.
Figure 7:
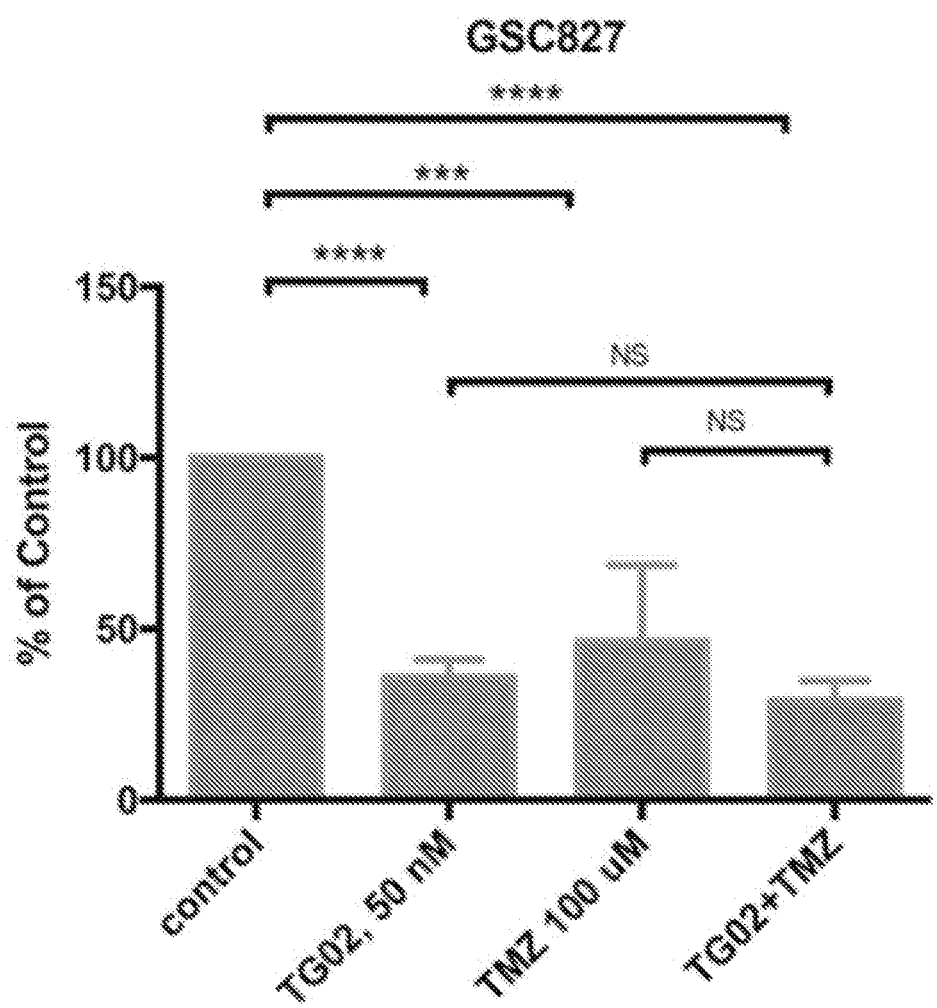
FIG. 7 is a bar graph showing the in vitro activity of TG02, TMZ, and TG02+TMZ in GSC827 cells

Several standard glioblastoma multiforme (GBM) cell lines and one stem cell line expressing $O^6$-methylguanine DNA methyltransferase (MGMT) were treated with TG02, temozolomiode (TMZ), or the combination of TG02 and TMZ in a 72-hour cell proliferation assay. See FIGS. 1-3. TG02, TMZ, and the TG02+TMZ combination was also tested in cell lines without MGMT expression. See FIGS. 4-7. The cells were seeded onto 12-well plates and treated with 50 nM of TG02, 100 μM of TMZ or TG02+TMZ for 72 hr. Cell viability was determined by cell counting.

Figure 8:
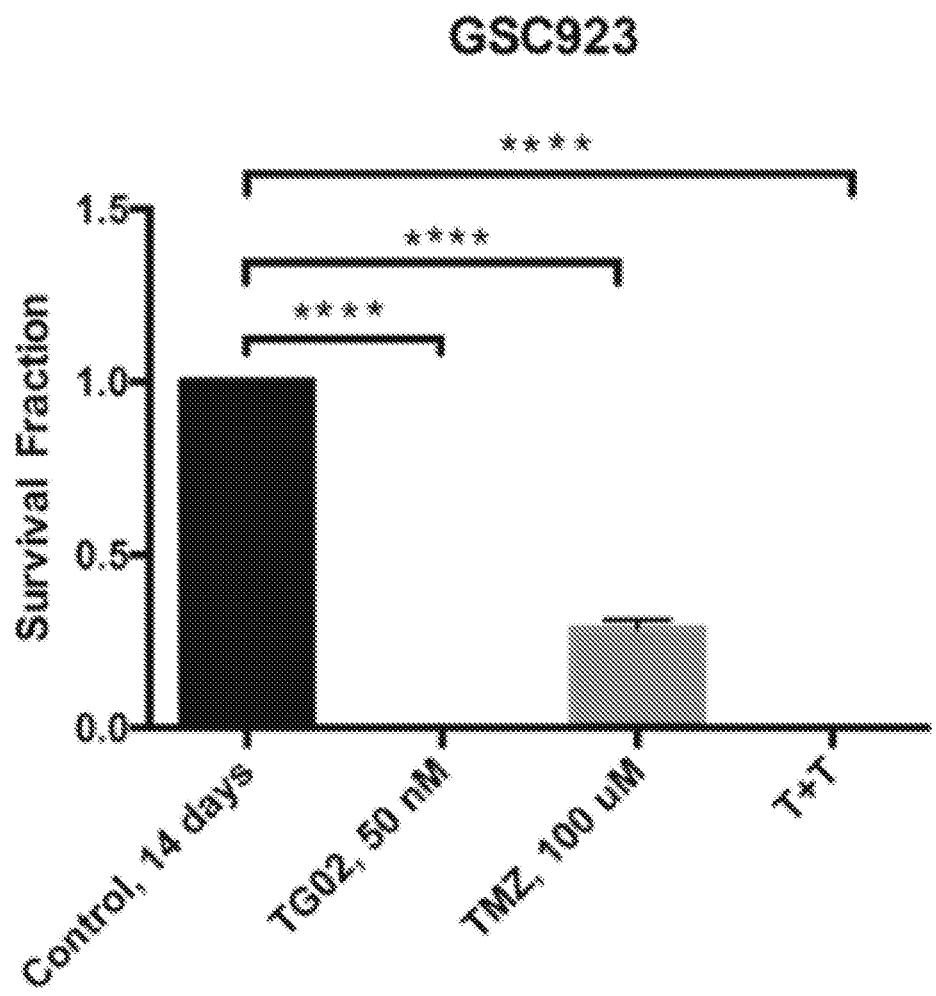
FIG. 8 is a bar graph showing the in vitro cytotoxicity of TG02, TMZ, and TG02+TMZ (T+T) in GSC923 cells.
Figure 9:
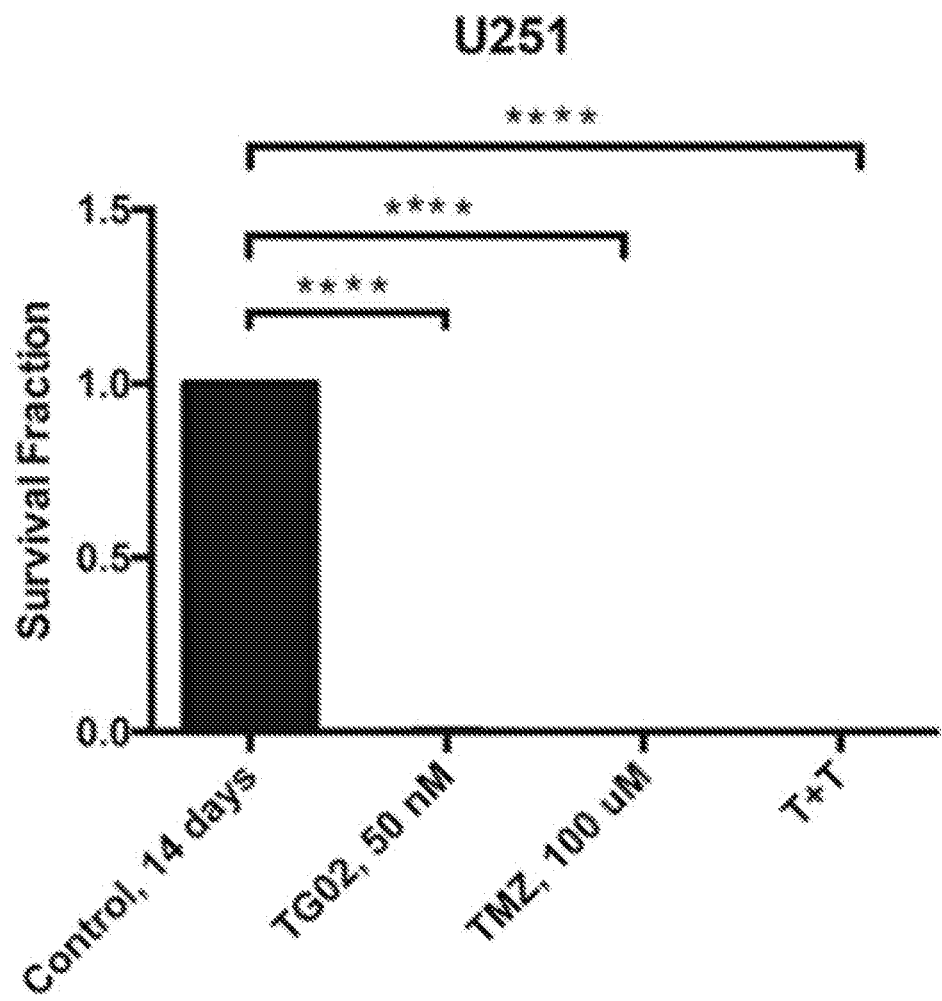
FIG. 9 is a bar graph showing the in vitro cytotoxicity of TG02, TMZ, and TG02+TMZ (T+T) in U251 cells.

The cytotoxic effect TG02, TMZ, and the combination of TG02 and TMZ was examined via the colony formation assay in GSC923 and U251 cells. See FIGS. 8 and 9.

Figure 10:
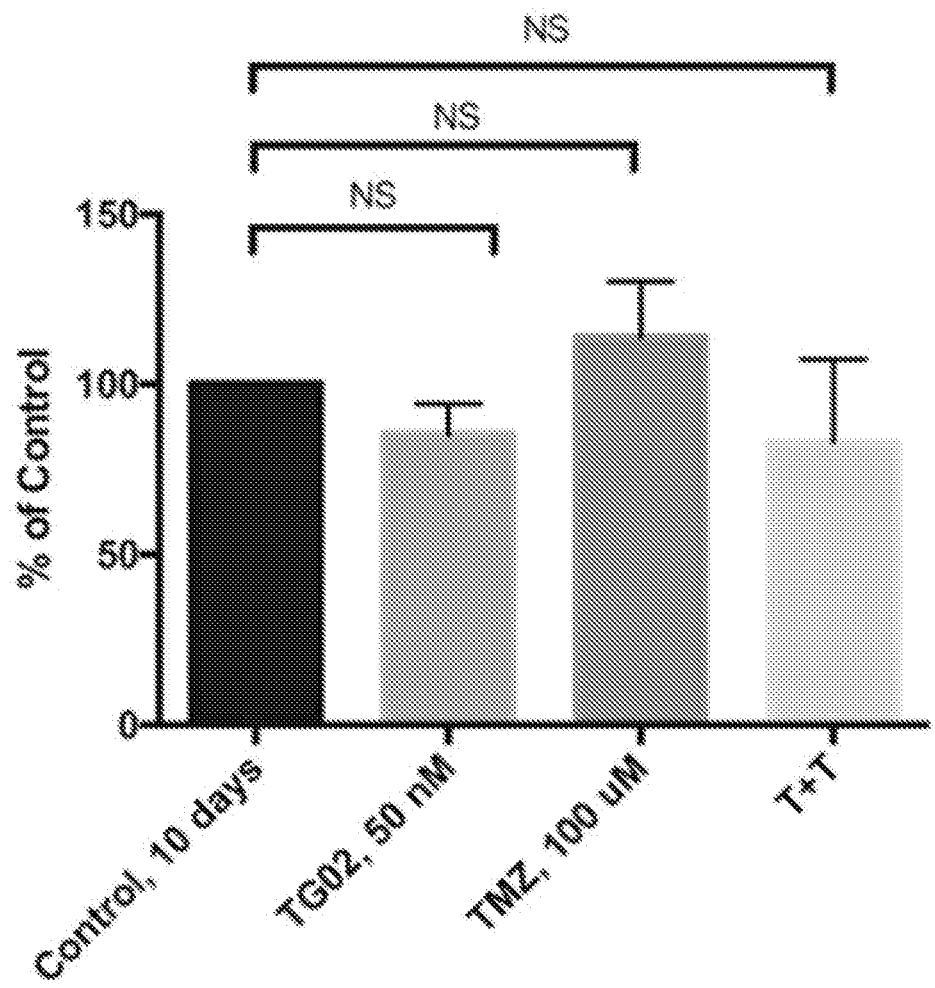
FIG. 10 is a bar graph showing a lack of in vitro activity of TG02, TMZ, and TG02+TMZ (T+T) in human pulmonary arterial endothelial cells.
Figure 11:
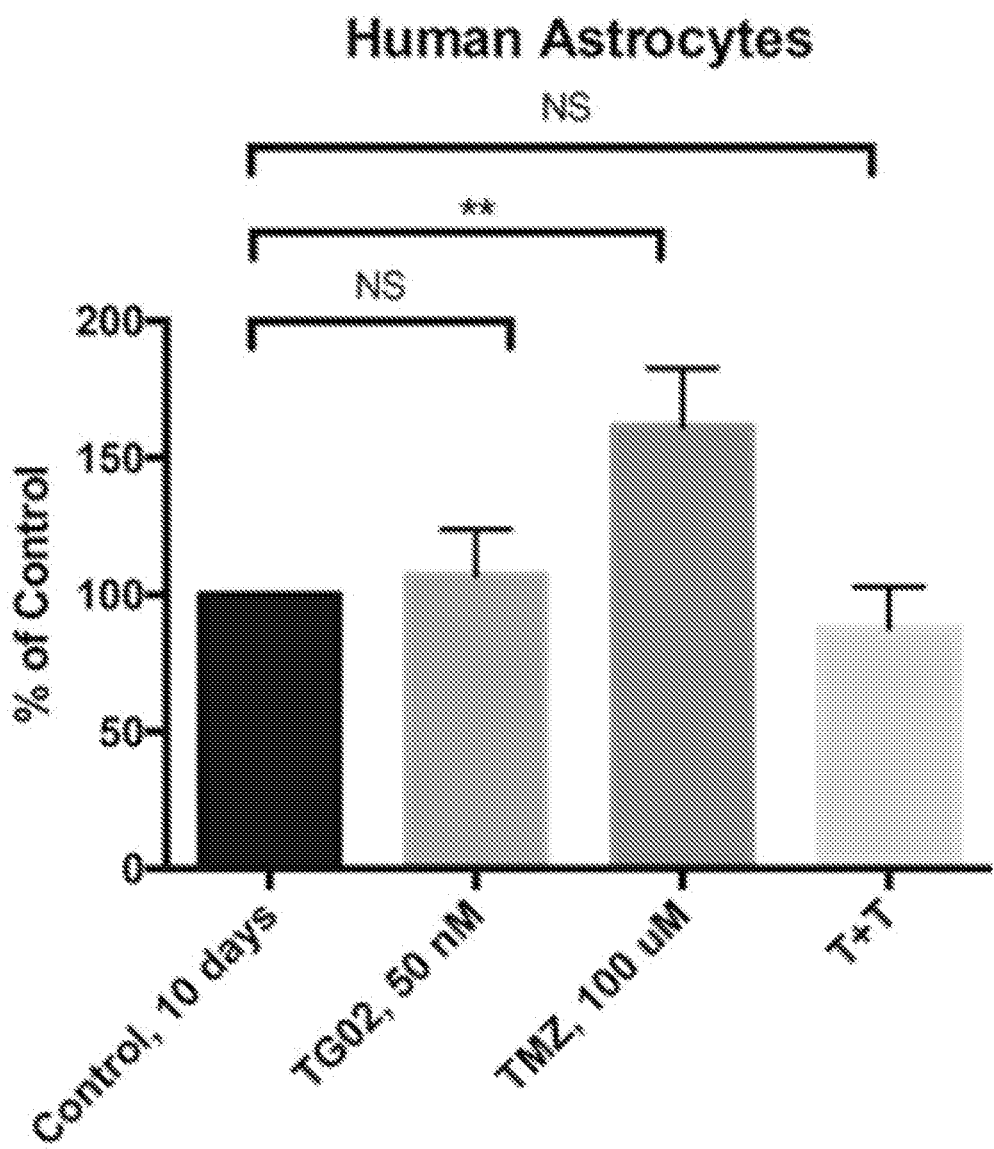
FIG. 11 is a bar graph showing a lack of in vitro activity of TG02, TMZ, and TG02+TMZ (T+T) in human astrocytes.

Pulmonary arterial endothelial cells and human astrocytes were tested with 50 nM of TG02, 100 μM of TMZ, or TG02+TMZ for 72 hr. The cells were then changed to normal medium and cultured for another 7 days. Cell viability was determined by cell counting. See FIGS. 10 and 11.

Figure 12:
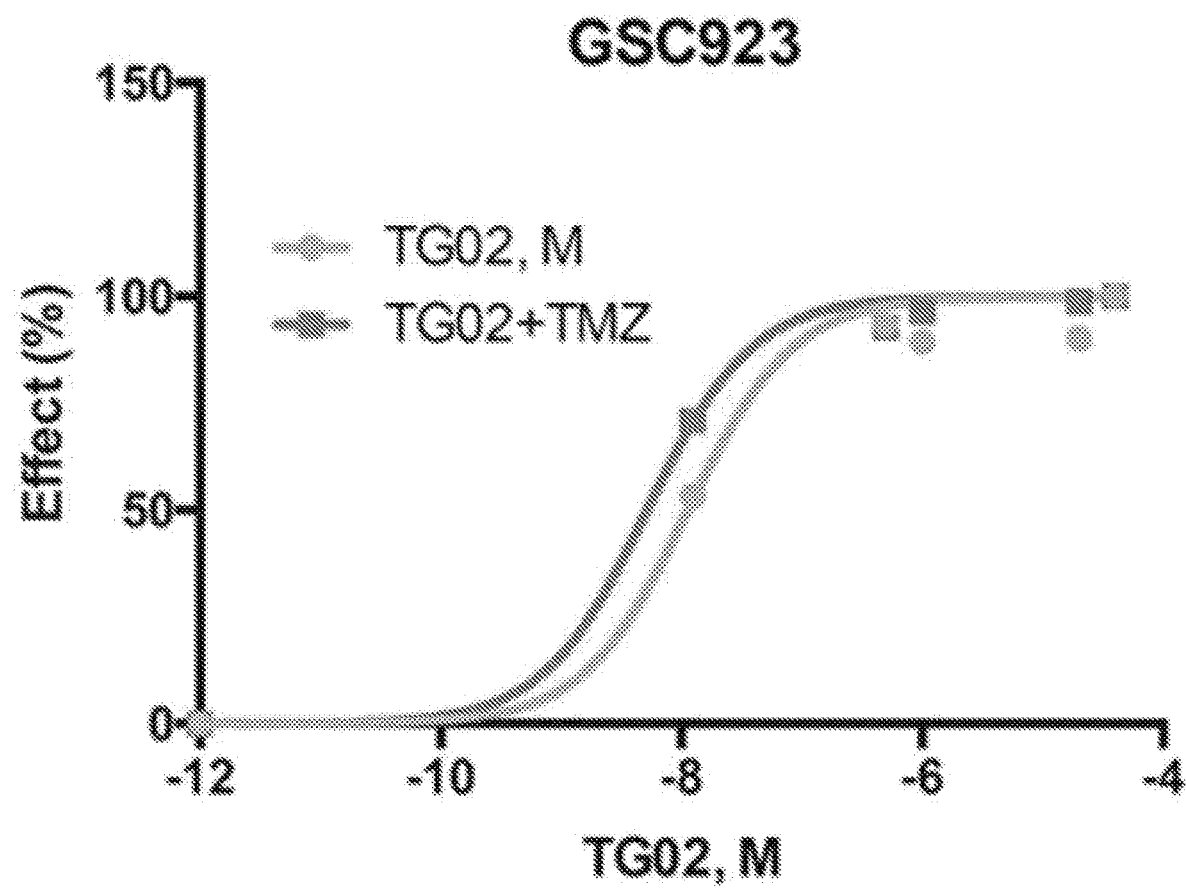
FIG. 12 is a dose response curve showing the in vitro activity of TG02 and TG02+TMZ in GSC923 cells.
Figure 13:
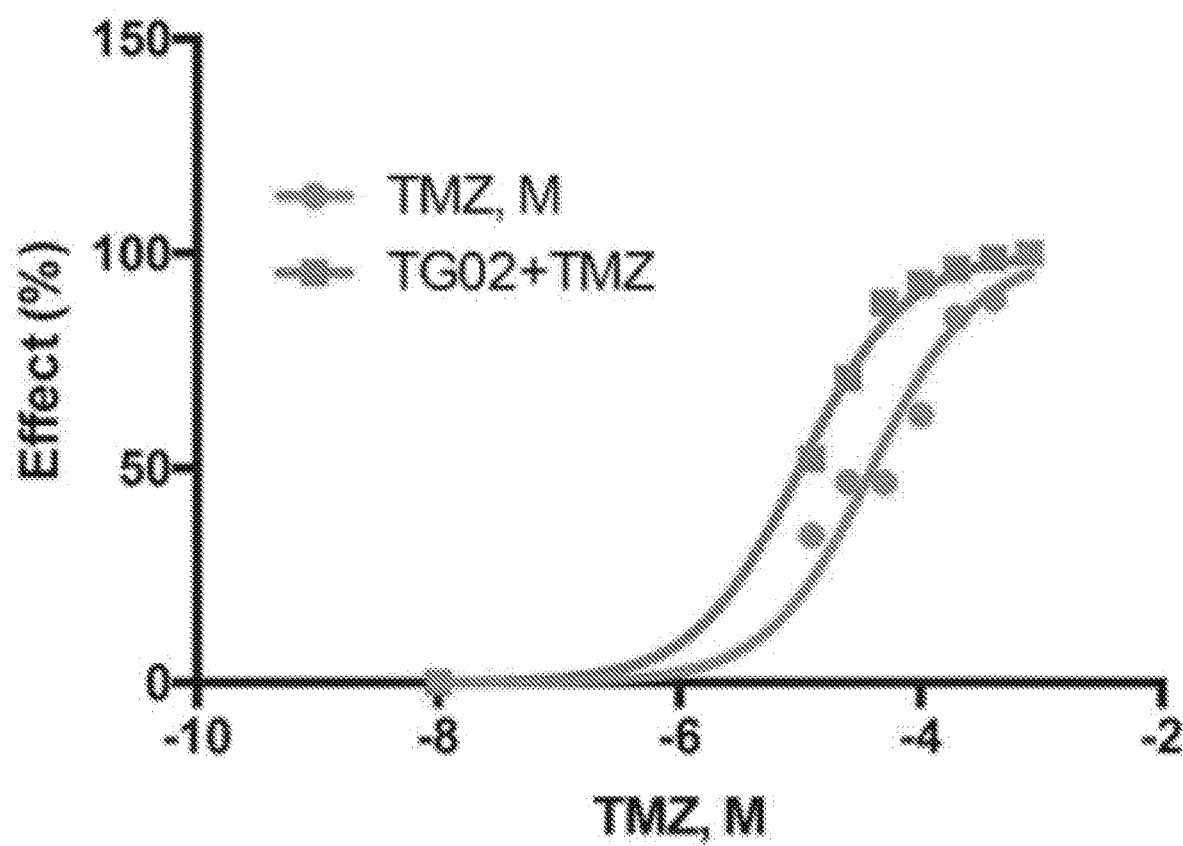
FIG. 13 is a dose response curve showing the in vitro activity of TMZ and TG02+TMZ in GSC923 cells.
Figure 14:
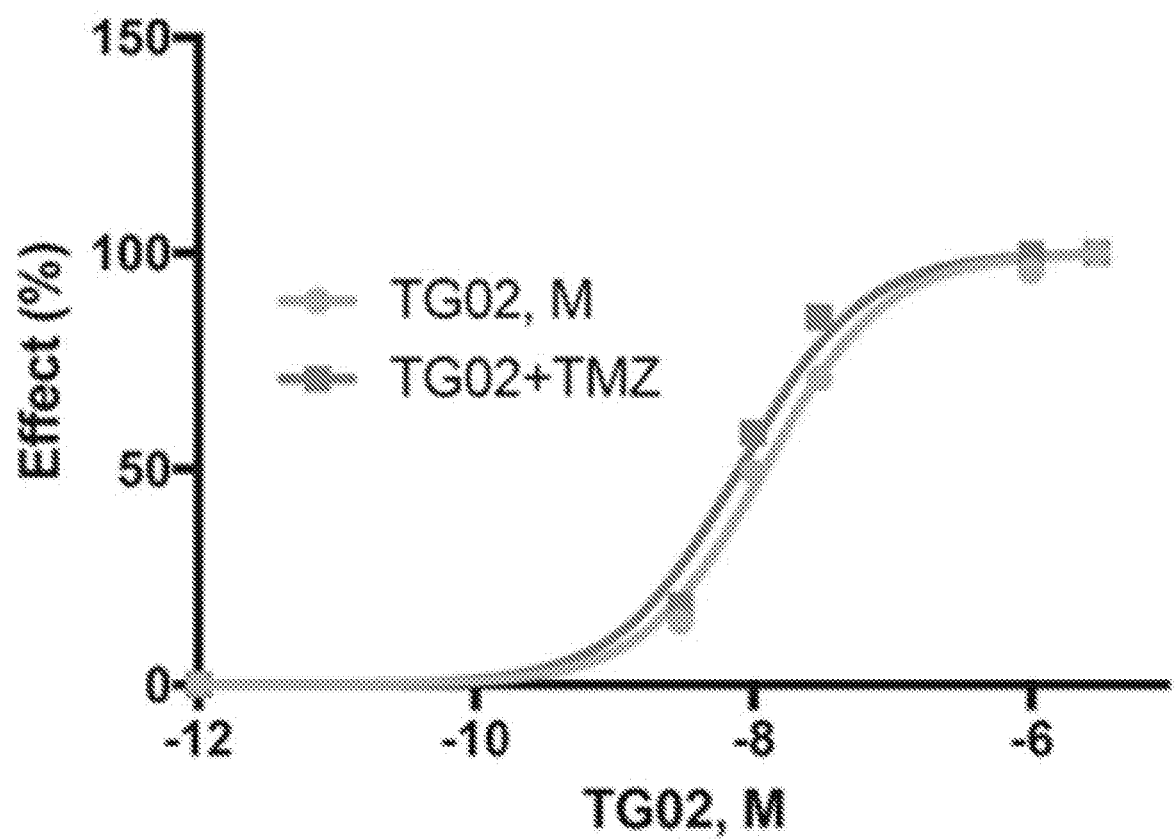
FIG. 14 is a dose response curve showing the in vitro activity of TG02 and TG02+TMZ in U251 cells.
Figure 15:
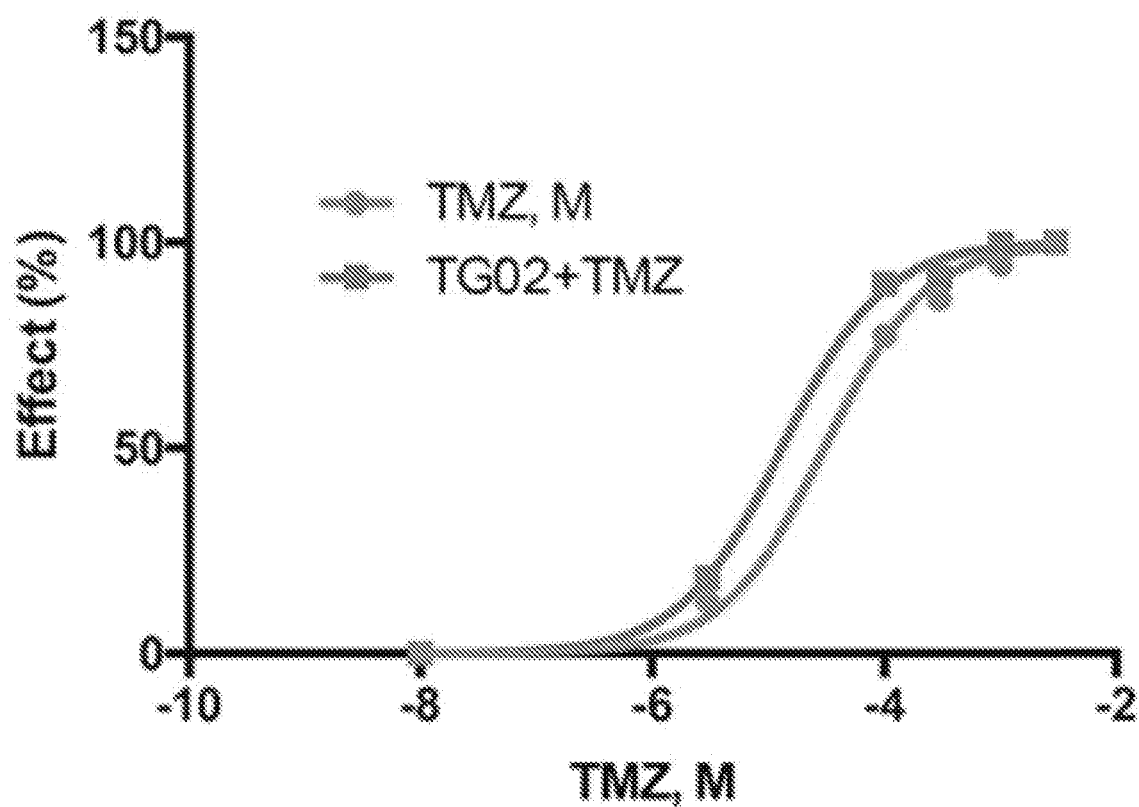
FIG. 15 is a dose response curve showing the in vitro activity of TMZ and TG02+TMZ in U251 cells.

GSC923 (FIGS. 12 and 13) and U251 (FIGS. 14 and 15) cells were exposed to various concentrations of TG02, TMZ, and TG02+TMZ for 72 hr, and cell viability was examined via cell counting. The synergistic effect of TG02+TMZ was determined by Combination Index (CI). CI values were calculated by COMPUSYN software and shown Table 2 for GSC923 cells and Table 3 for U251 cells. CI<1 is a synergistic, CI=1 is an additive, and CI>1 is an antagonistic effect of the two compounds combined.

TABLE 2

| Fraction Affected (Fa) | CI value |
|---|---|
| 0.25 | 0.077 |
| 0.5 | 0.136 |
| 0.75 | 0.242 |
| 0.90 | 0.430 |

TABLE 3

| Fraction Affected (Fa) | CI value |
|---|---|
| 0.25 | 0.029 |
| 0.5 | 0.104 |
| 0.75 | 0.376 |
| 0.90 | 1.333 |

Figure 16:
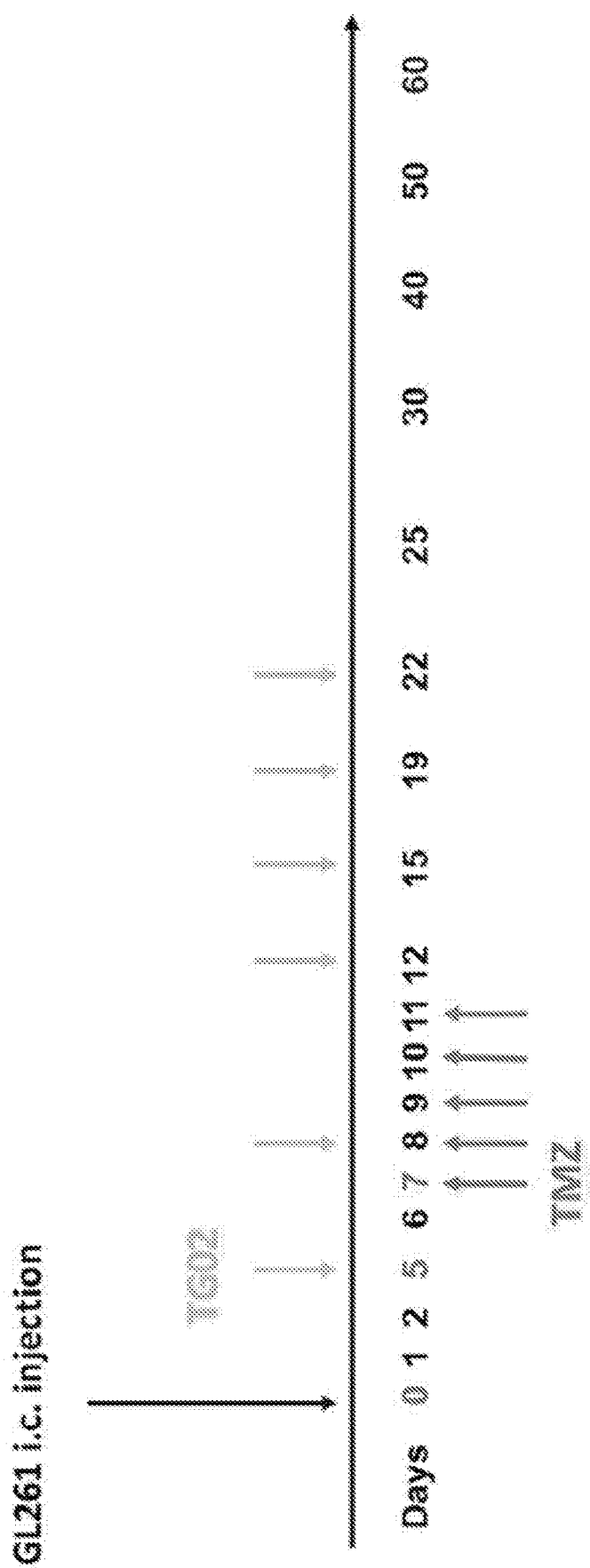
FIG. 16 is a schematic illustration of TG02 and TMZ administration in a mouse glioma GL261 cell allograft model.
Figure 17:
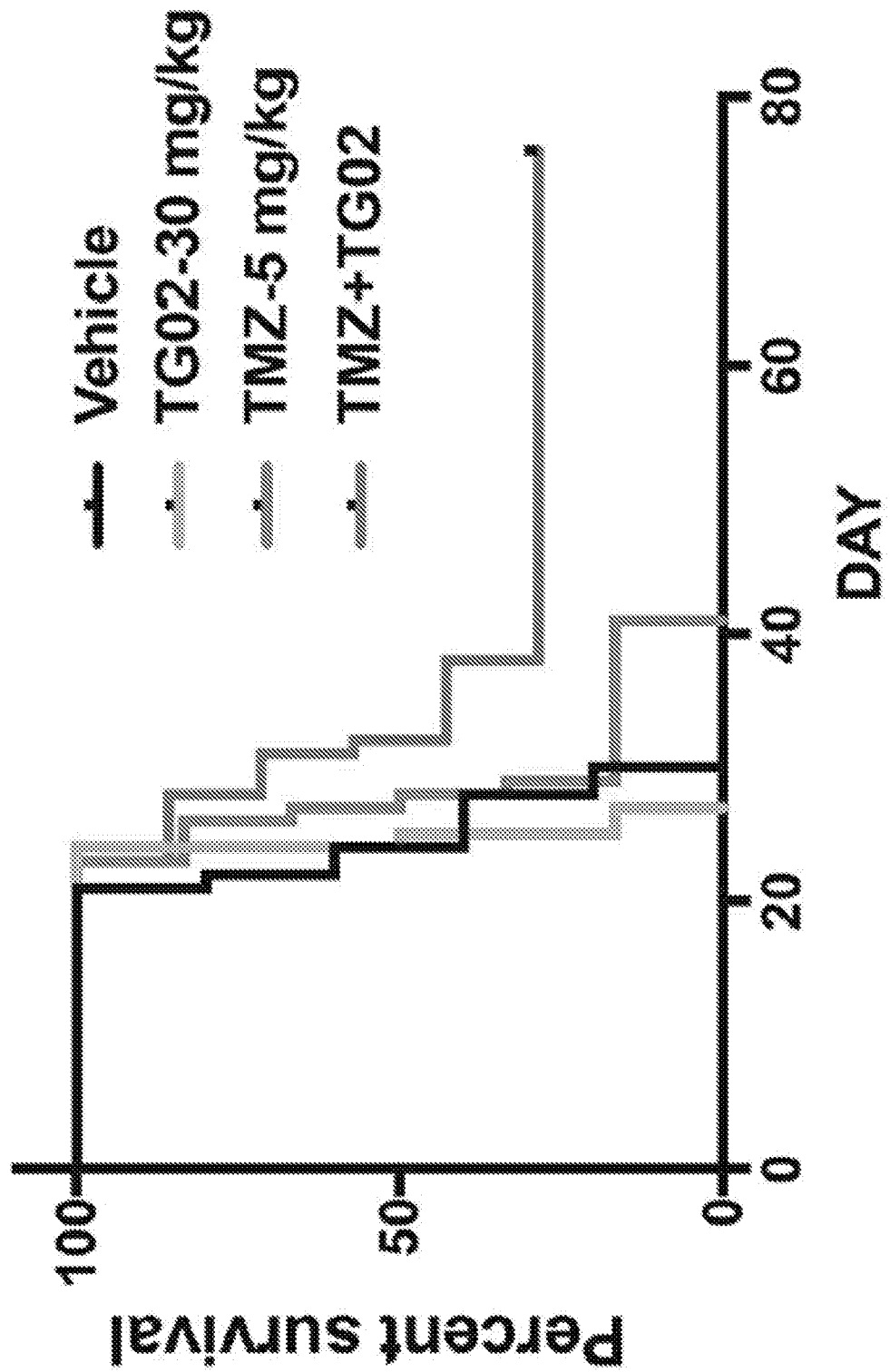
FIG. 17 is a line graph showing percent survival following TG02, TMZ, and TG02+TMZ administration in a mouse glioma GL261 cell allograft model.
Figure 18:
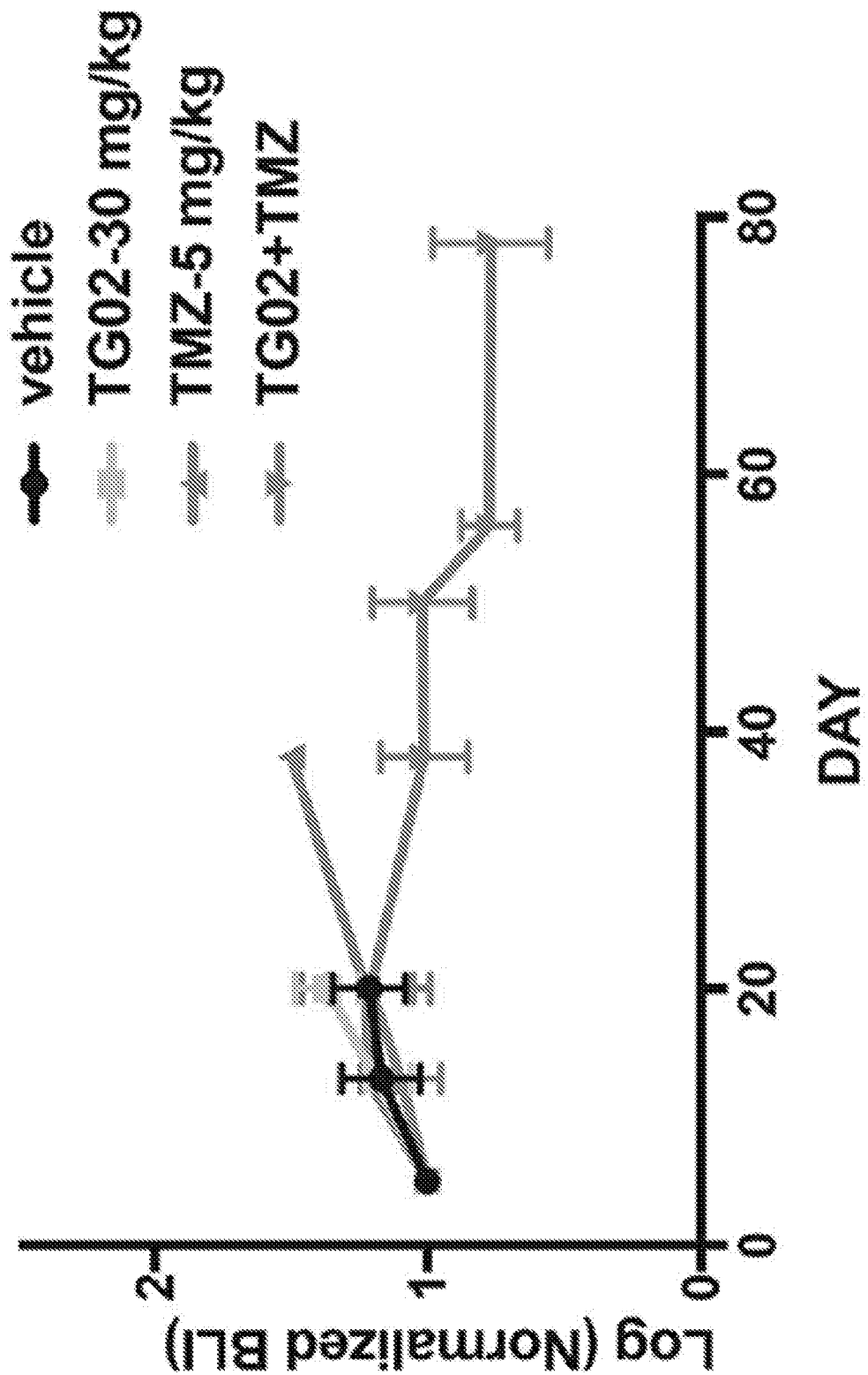
FIG. 18 is a line graph showing the tumor burden following TG02, TMZ, and TG02+TMZ administration in a mouse glioma GL261 cell allograft model.

FIG. 16 shows a schematic illustration of drug administration in an mouse glioma GL261 cell allograft model. Mouse glioma GL261 cells were injected stereotactically into the striatum of female C57BL/6 albino mice (n=5-7 per cohort) followed by vehicle, TG02, TMZ, and TG02+TMZ combination treatment. A median overall survival of 24, 24.5, 27.5, and 32 days, respectively was observed. See FIG. 17. The result was analyzed using Logrank test for trend in GraphPad Prism software (Chi square=9.063, df=1, P value=0.0026**). The turmor burden was determined by bioluminescence imaging (BLI) taken using the PerkinElmer IVIS® Spectrum. The intensity of BLI was calculated and normalized to the initial intensity at day 5. See FIG. 18.

Example 6

TG02 Activity in Hepatocellular Carcinoma (HCC) Cells and Xenograft Model

Figure 19:
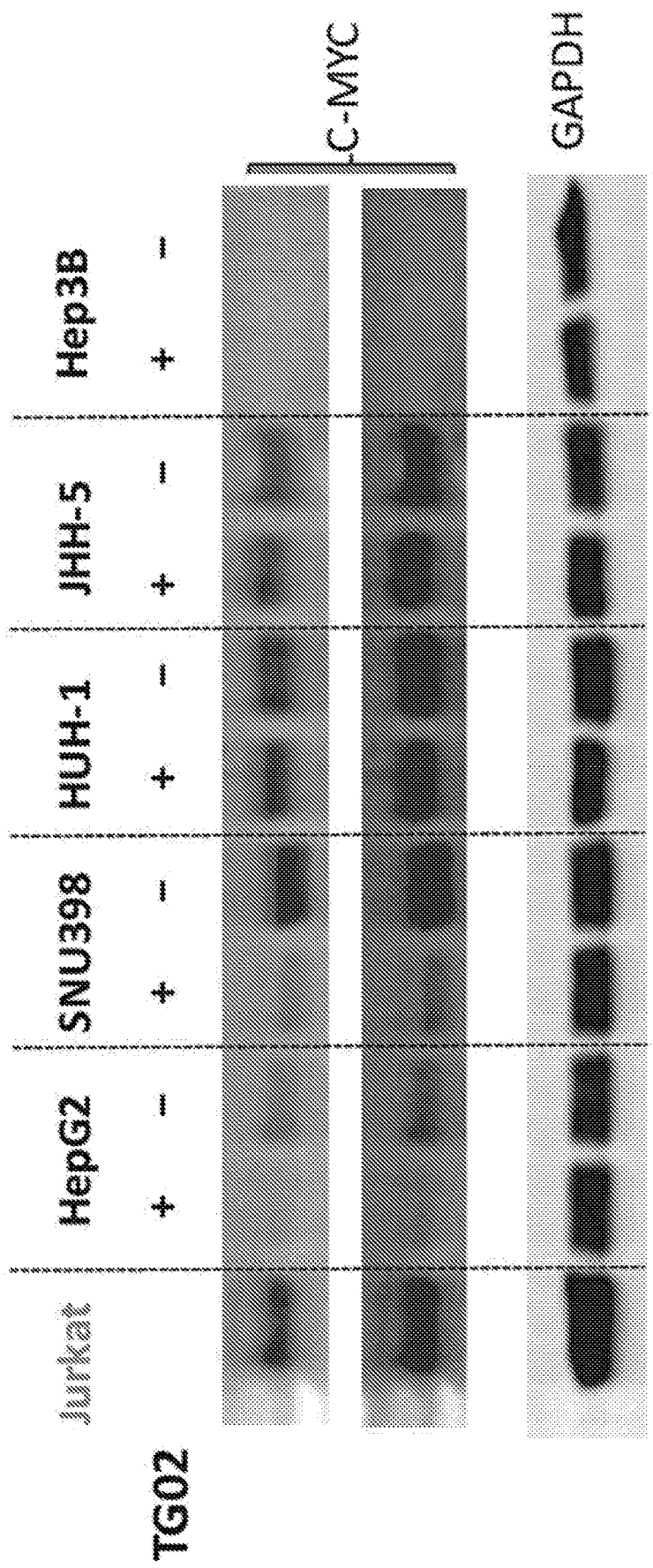
FIG. 19 is an illustration showing the effect of TG02 on MYC protein levels in hepatocellular carcinoma (HCC) cells.

The effect of TG02 on MYC expression in HCC cell lines was investigated. Five HCC cell lines with varying levels of MYC expression were treated with 0.5 TG02 for 24 hours and MYC expression was evaluated by western blot. See FIG. 19. MYC expression levels were decreased by TG02 treatment in HepG2, SNU398 and HUH-1 cell lines but not in the JHH-5 line. Hep3B cells did not express MYC.

Figure 20:
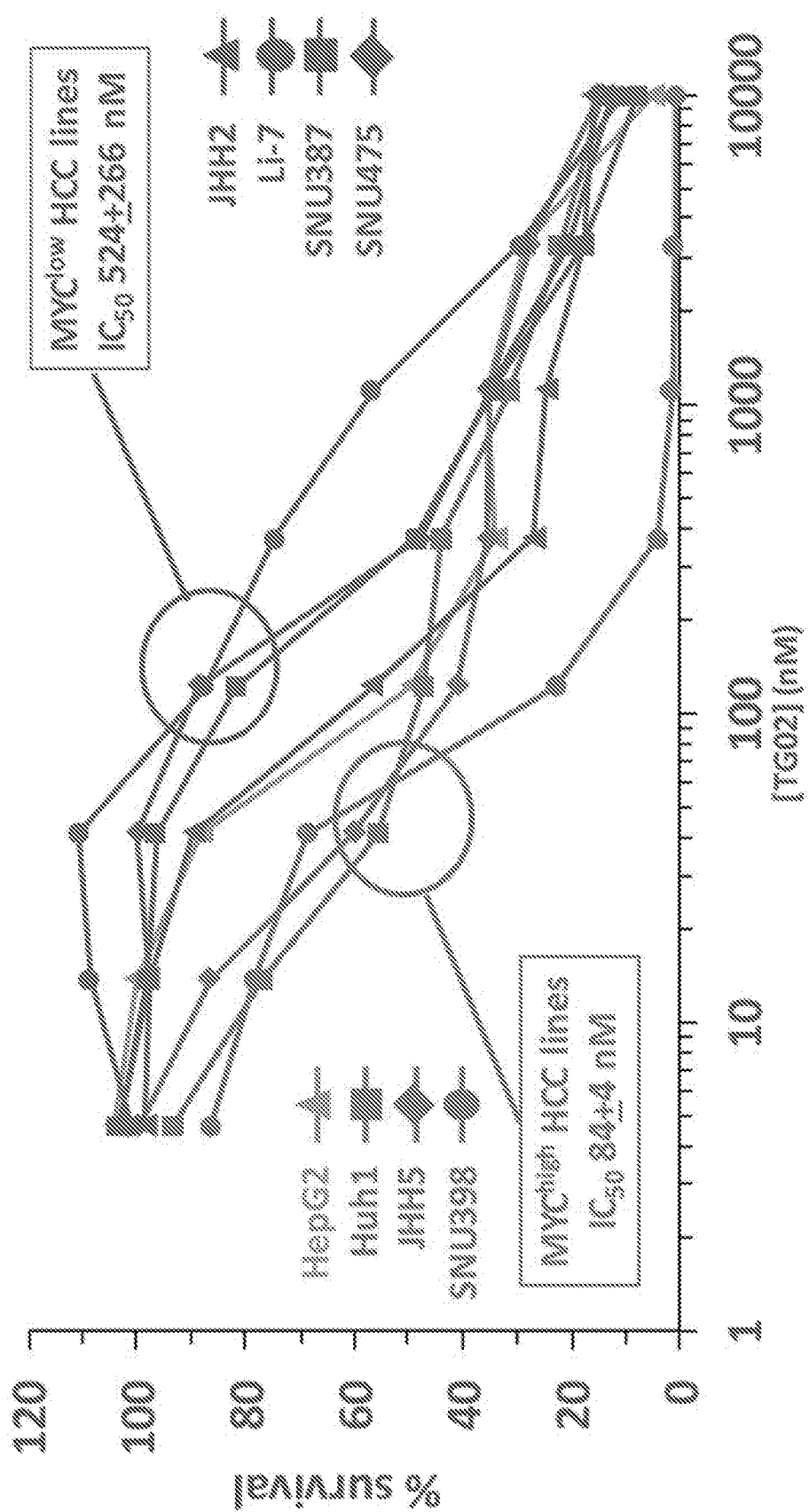
FIG. 20 is a dose response curve showing the effect of TG02 on MYC protein levels in HCC cells.

Eight HCC cell lines with either high or low MYC expression were then treated with TG02 in vitro. TG02 treatment resulted in inhibition of cell proliferation in all HCC cell lines tested. TG02 is selectively more potent in the cells lines with high levels of MYC expression as compared to those cells with low levels of MYC expression, with mean $IC_{50}$ values of 84 nM and 524 nM, respectively. See FIG. 20.

Figure 21:
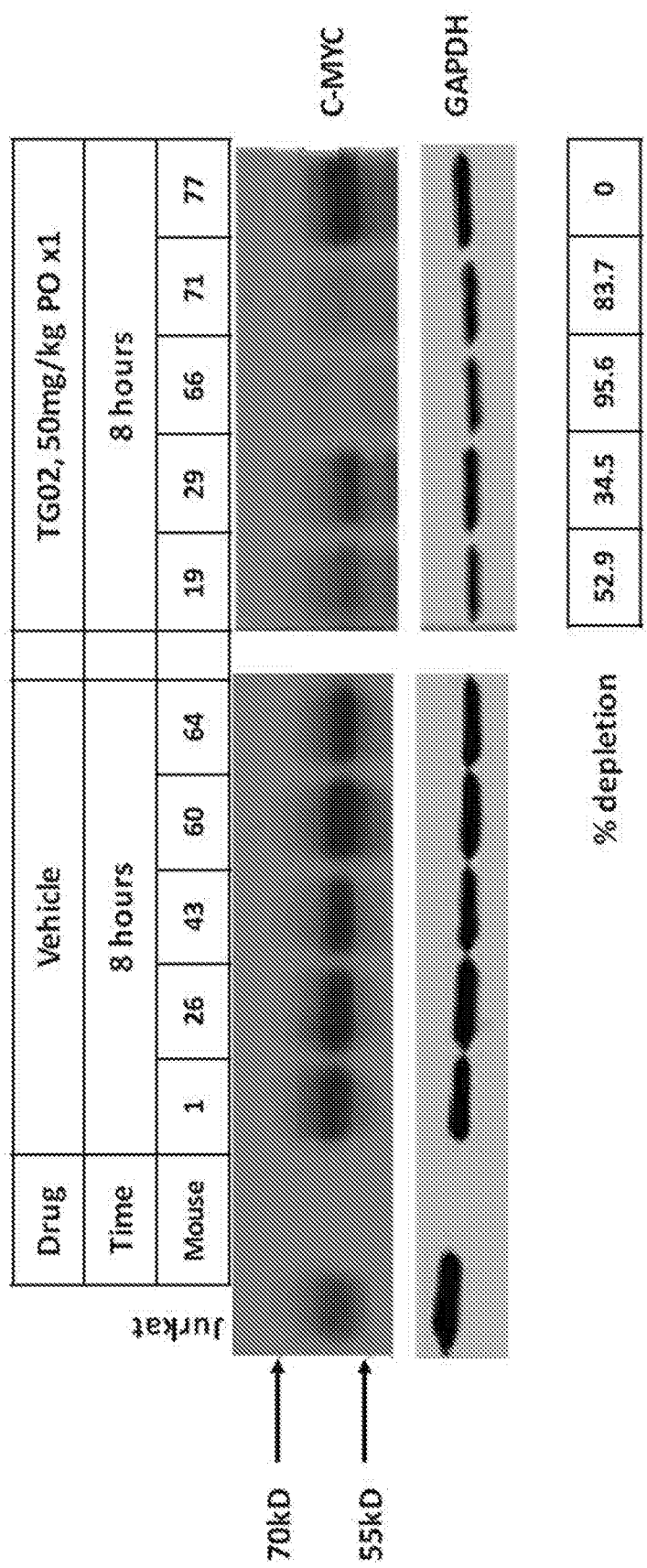
FIG. 21 is is an illustration showing showing the effect of TG02 on MYC protein levels in HCC tumor cells.

Inhibition of MYC expression was also measured in vivo. HepG2 hepatocellular carcinoma xenografts was grown orthotopically in Balb/c nude mice. TG02 or vehicle was given orally at 50 mg/kg to 5 mice each; tumors were collected 8 hours post-treatment and MYC protein expression levels were measured by western blot. MYC expression was observed in each of the control tumors. In the TG02 treatment group, MYC expression levels were decreased in 4 of 5 animals, with substantial MYC depletion in two animals and partial reduction in two other animals. See FIG. 21.

Figure 22:
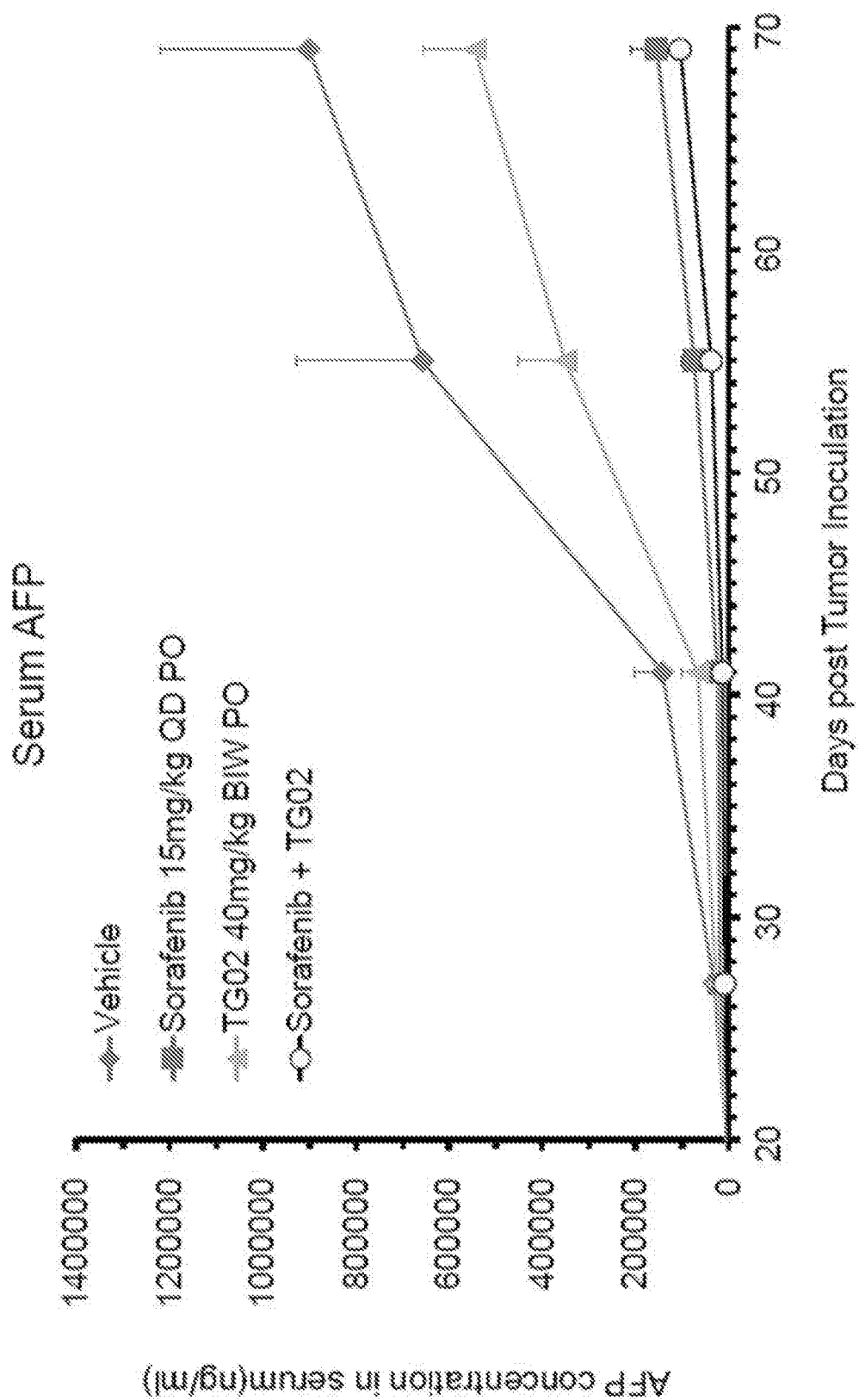
FIG. 22 is a line graph showing the in vivo activity of TG02 and TG02+sorafenib in an orthotopic model of HepG2 HCC xenografts.
Figure 23:
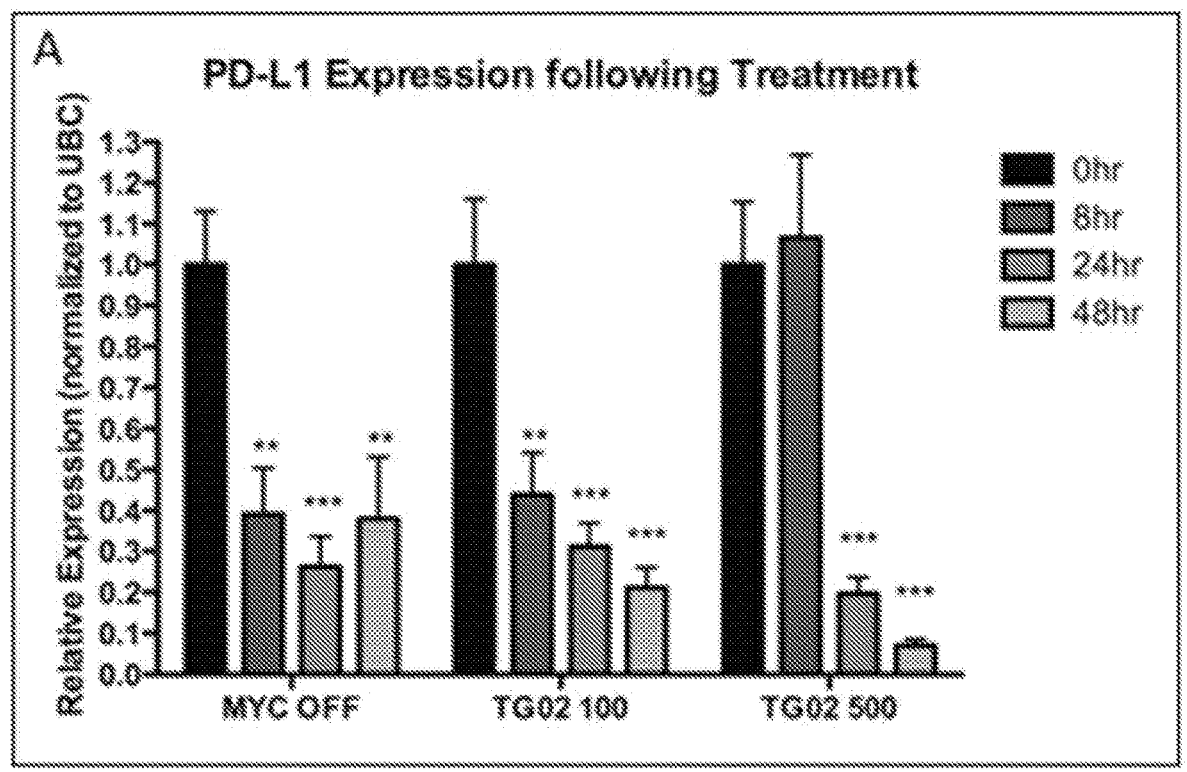
FIG. 23 is a bar graph showing PD-L1 expression following treatment with TG02 in a transgenic mouse model of MYC-induced T cell acute lymphoblastic leukemia.
Figure 24:
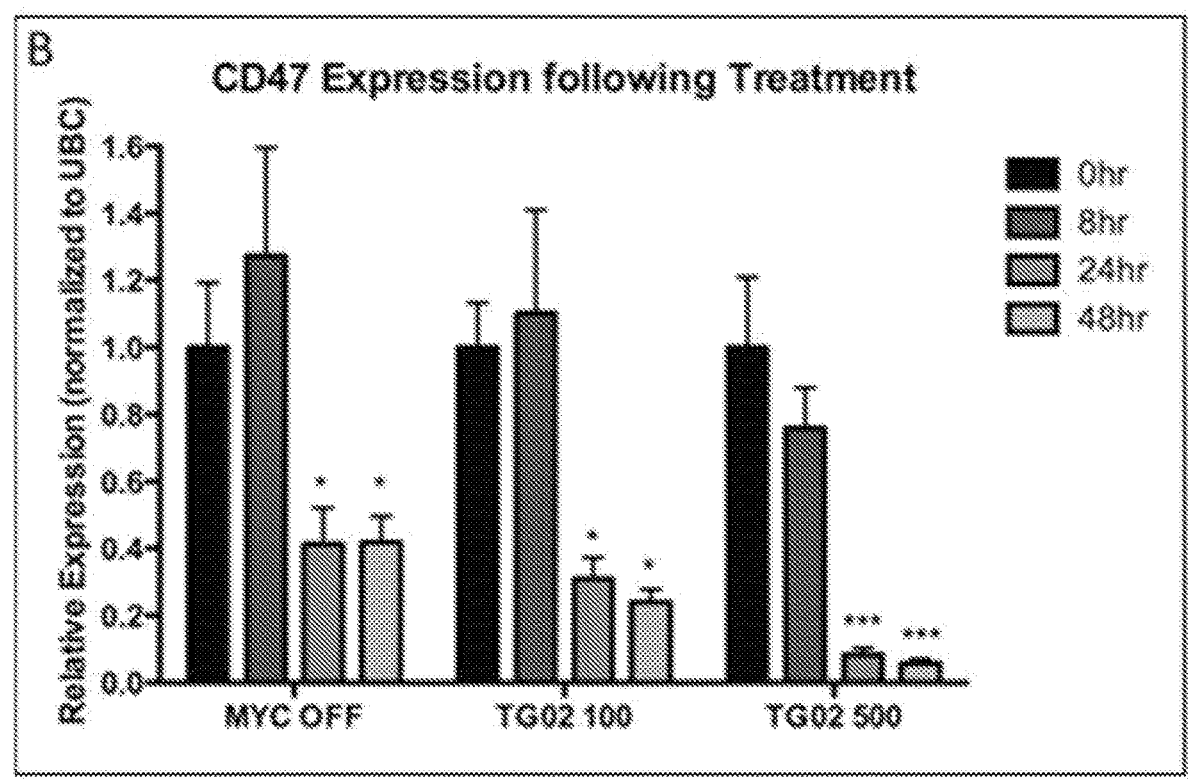
FIG. 24 is a bar graph showing CD47 expression following treatment with TG02 in a transgenic mouse model of MYC-induced T cell acute lymphoblastic leukemia.

The therapeutic efficacy of TG02 as a single agent or in combination with sorafenib in the treatment of orthotopic HepG2 human liver cancer xenograft model was evaluated in BALB/c nude mice. On Day 19 post-inoculation, mice were randomized into treatment groups based on baseline serum AFP levels which trace tumor volume in the liver. TG02 was given orally twice weekly at 50 mg/kg and reduced to 40 mg/kg. Sorafenib was given orally daily at 15 mg/kg. TG02 as a single agent had a modest effect on tumor volume. TG02 combined with sorafenib led to significant anti-tumor activity. See FIG. 22.

Example 7

TG02-Mediated CDK9 Inhibition

A Tet-off transgenic mouse model of MYC-induced T cell acute lymphoblastic leukemia (MYC T-ALL) which overexpresses and is dependent on MYC, was treated with TG02 at 100 or 500 μM.

MYC is a transcription factor that regulates the expression of a multitude of gene products involved in cell proliferation, growth, differentiation and apoptosis. The MYC gene is genetically activated and over-expressed in many human cancers and this over-expression has been causally linked to tumorigenesis, driving malignant growth and immune evasion. See, e.g., Alvarez-Fernandez et al., Clin. Cancer Res. Off. J. Am. Assoc. Cancer Res. 19:2677-2687 (2013); Carter et al., Blood 105:4043-4050 (2005); Casey et al., Science 352:231-231 (2016); Hannah, A. L., Curr. Mol. Med. 5:625-642 (2005); and Parcells et al., Stem Cells Day. Ohio 24:1174-1184 (2006).

Figure 25:
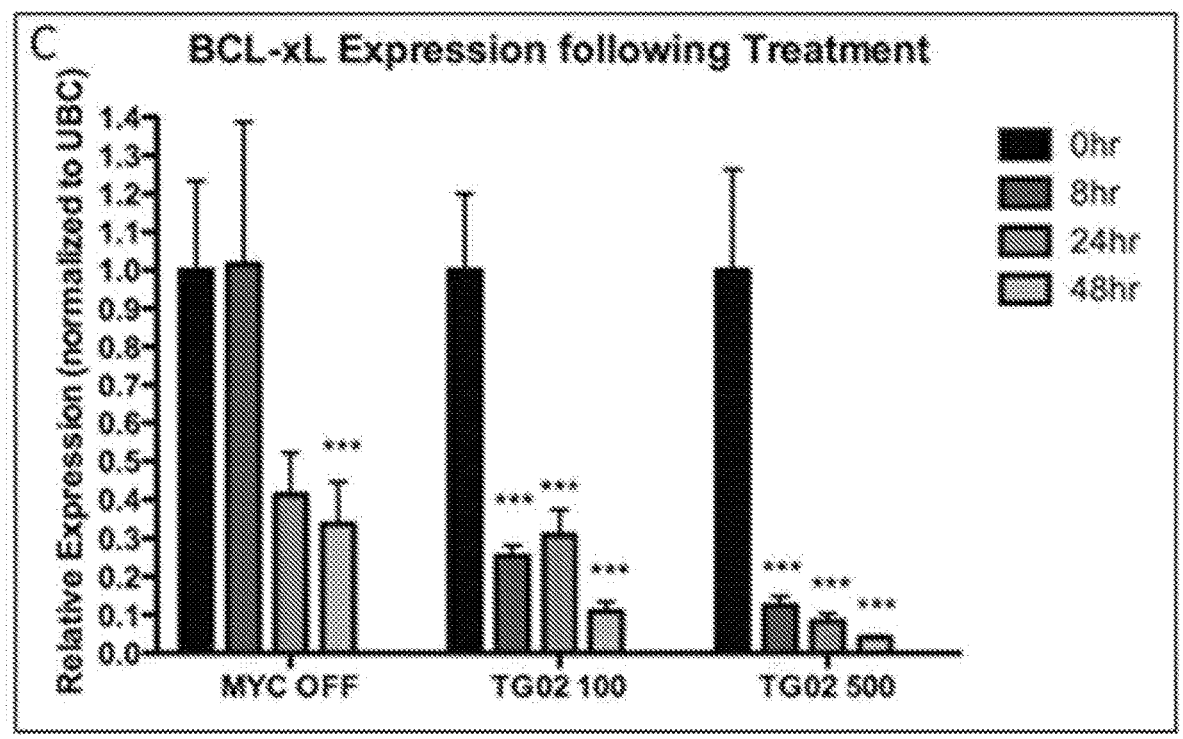
FIG. 25 is a bar graph showing BCL-xL expression following treatment with TG02 in a transgenic mouse model of MYC-induced T cell acute lymphoblastic leukemia.
Figure 26:
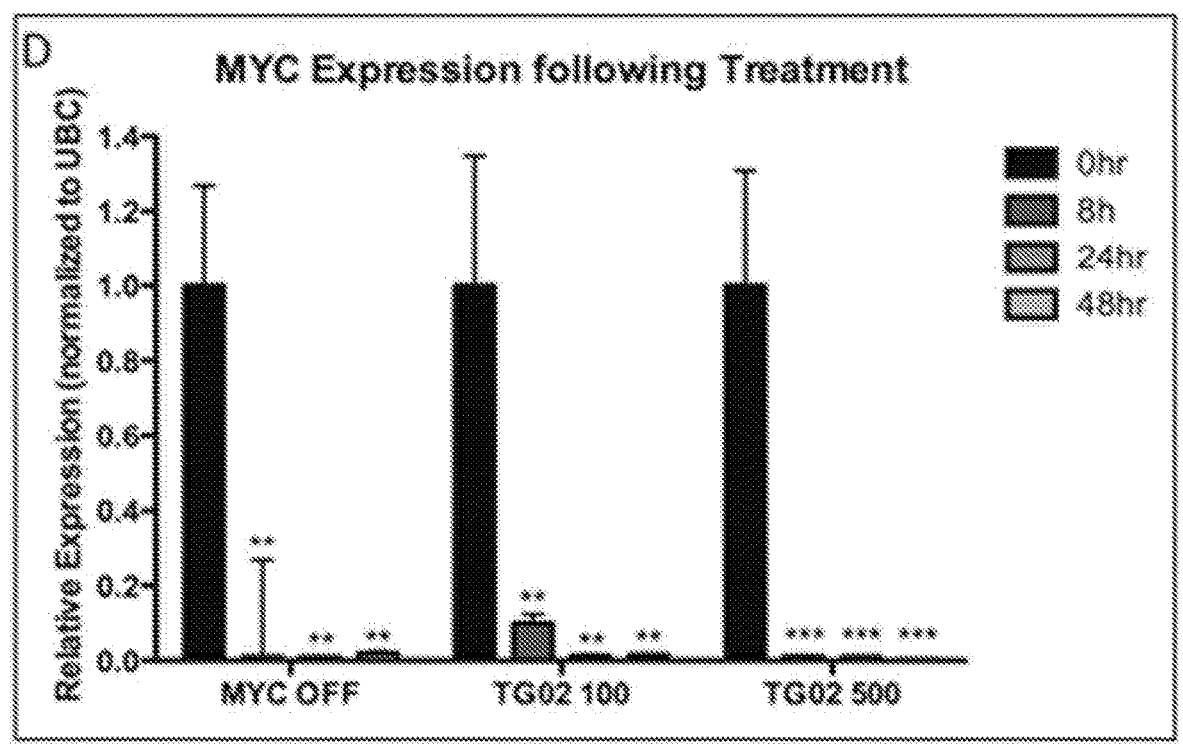
FIG. 26 is a bar graph showing MYC expression following treatment with TG02 in a transgenic mouse model of MYC-induced T cell acute lymphoblastic leukemia.

As shown in FIGS. 23-26, when MYC was turned "on," PD-L1 was expressed as detected by RT-PCR (t=0 hr). But when MYC was turned "off", both CD47 and PD-L1 expression was significantly reduced in a time dependent manner. TG02 led to a time- and dose-dependent down-regulation of both PD-L1 and CD47 mRNA expression in MYC T-ALL cells (FIGS. 23 and 24, respectively) and both BCL-xL and MYC expression were down-regulated (FIGS. 25 and 26, respectively). Reduced expression of both CD47 and PD-L1 on tumor cells may result in reduced immune evasion and increased tumor cell death.

Example 8

TG02 in Combination with Anti-PD-1

The combination of TG02 and PD-1 mAb (anti-PD-1) was tested in an orthotopic GL261 glioma model. GL261 allografts were established for 3 days and the mice were then randomized into 6 treatment cohorts (n=8) based on the bioluminescent tumor volumes.

Figure 27:
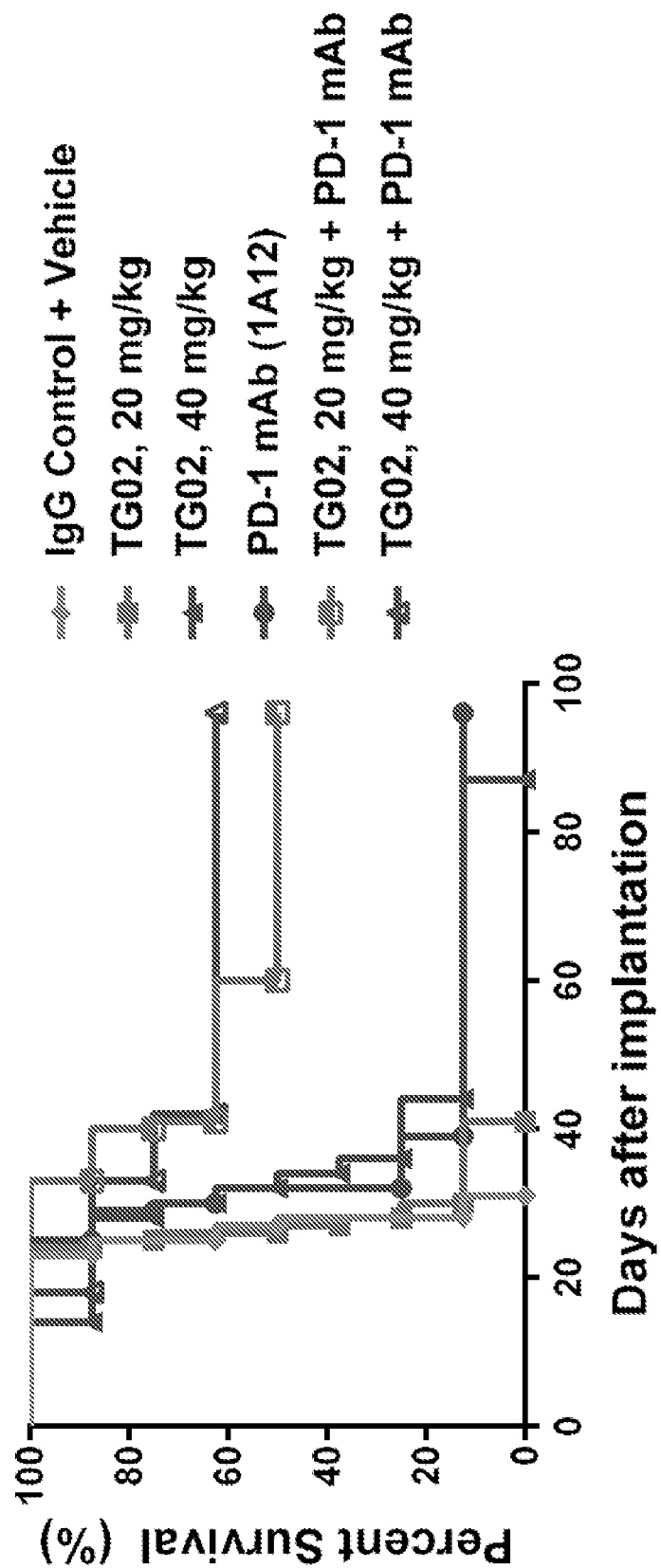
FIG. 27 is a line graph showing the efficacy of TG02 in combination with anti-PD-1 in a mouse syngeneic GL261 orthotopic glioblastoma model.

Mice were treated with vehicle, TG02 alone (20 or 40 mg/kg), PD-1 mAb alone (500 ug), and the combination of TG02 and anti-PD-1. Median survival times of the mice were 27.5, 26.5, 33, 32, 78 and >95 days, respectively (FIG. 27).

There was a significant survival benefit in TG02 alone at 40 mg/kg (0.009), PD-1 mAb alone (0.003), TG02 20 mg/kg+PD-1 mAb (0.0001), and TG02 40 mg/kg+PD-1 mAb (0.0001) treated-mice compared with the vehicle group.

Example 9

TG02 Induces Cell Death and Synergizes with Radiation in MYC-Driven Glioblastoma The relationship between TG02 antitumor activity and MYC expression was tested in a panel of patient-derived GBM cell lines (PDCLs). TG02 inhibited six out of twelve PDCLs at an $IC_{50}$ of less than 0.2 µM. See Table 4.

TABLE 4

| Patient-derived GBM lines | TG02 $IC_{50}$ (µM) |
|---|---|
| BT245 | 0.066 |
| BT360 | 0.073 |
| BT145 | 0.052 |
| BT224 | 0.109 |
| BT187 | 0.176 |
| BT164 | 0.178 |
| BT228 | 0.267 |
| BT286 | 0.371 |
| BT182 | 0.416 |
| BT359 | 0.624 |
| BT139 | 57.88 |
| BT181 | ~4828 |

Figure 28:
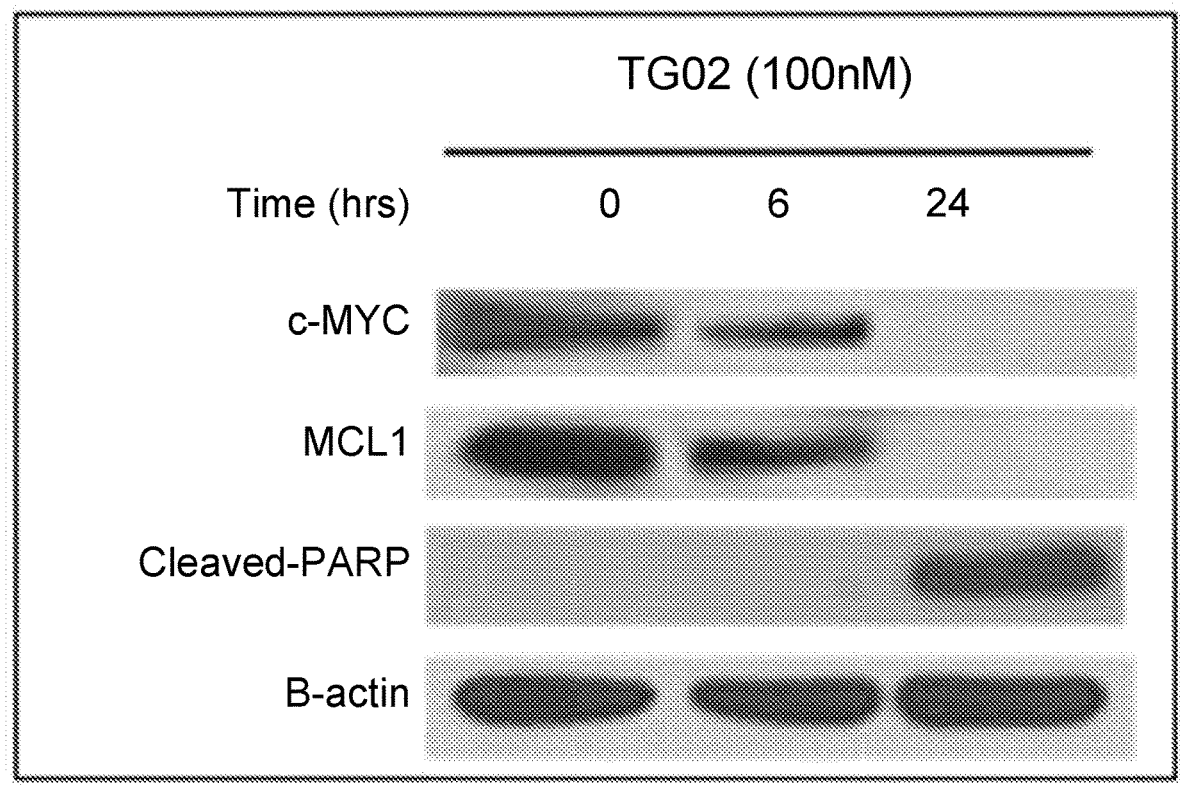
FIG. 28 is an illustration showing that BT245 tumor cells exposed to TG02 show inhibition of MYC and MCL-1 expression.
Figure 29:
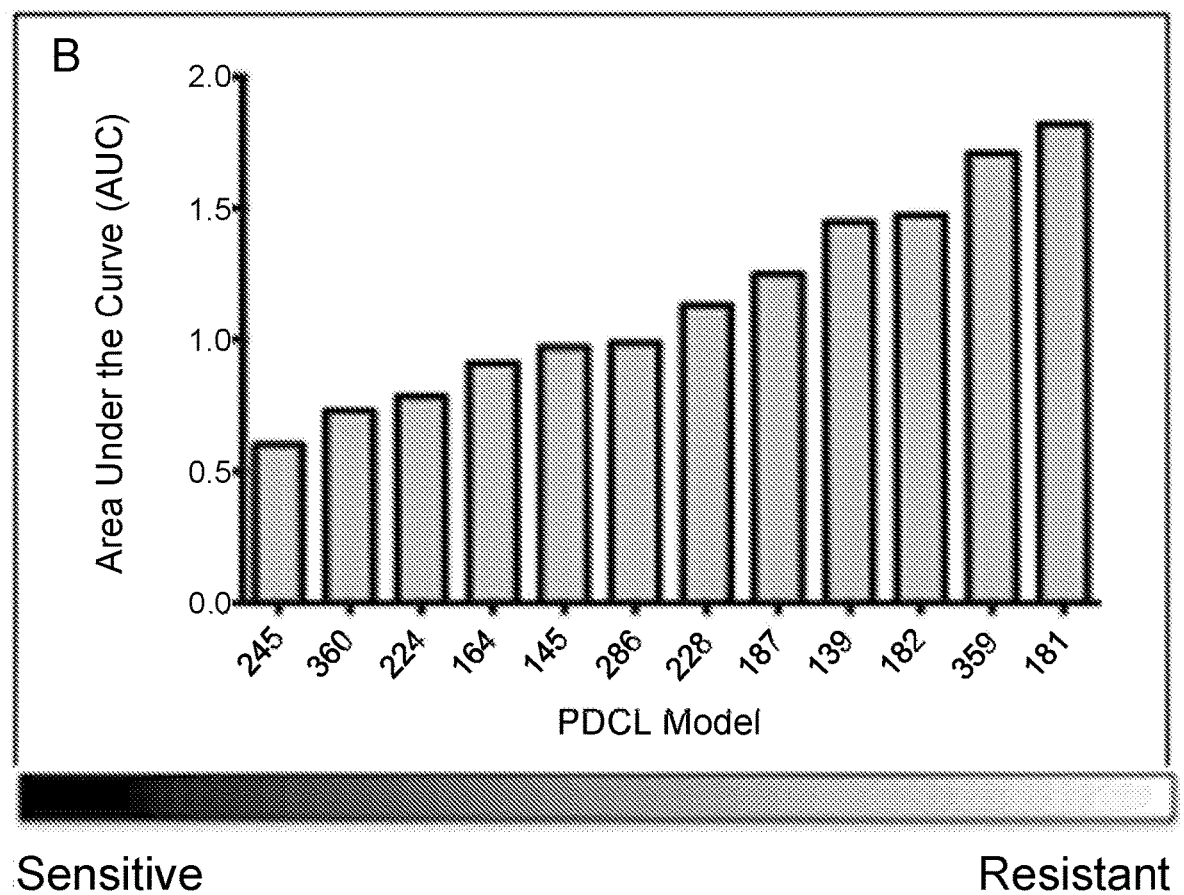
FIG. 29 is a bar graph showing the area under the curve (AUC) for TG02 induced inhibition in glioblastoma (GBM) cells.
Figure 30:
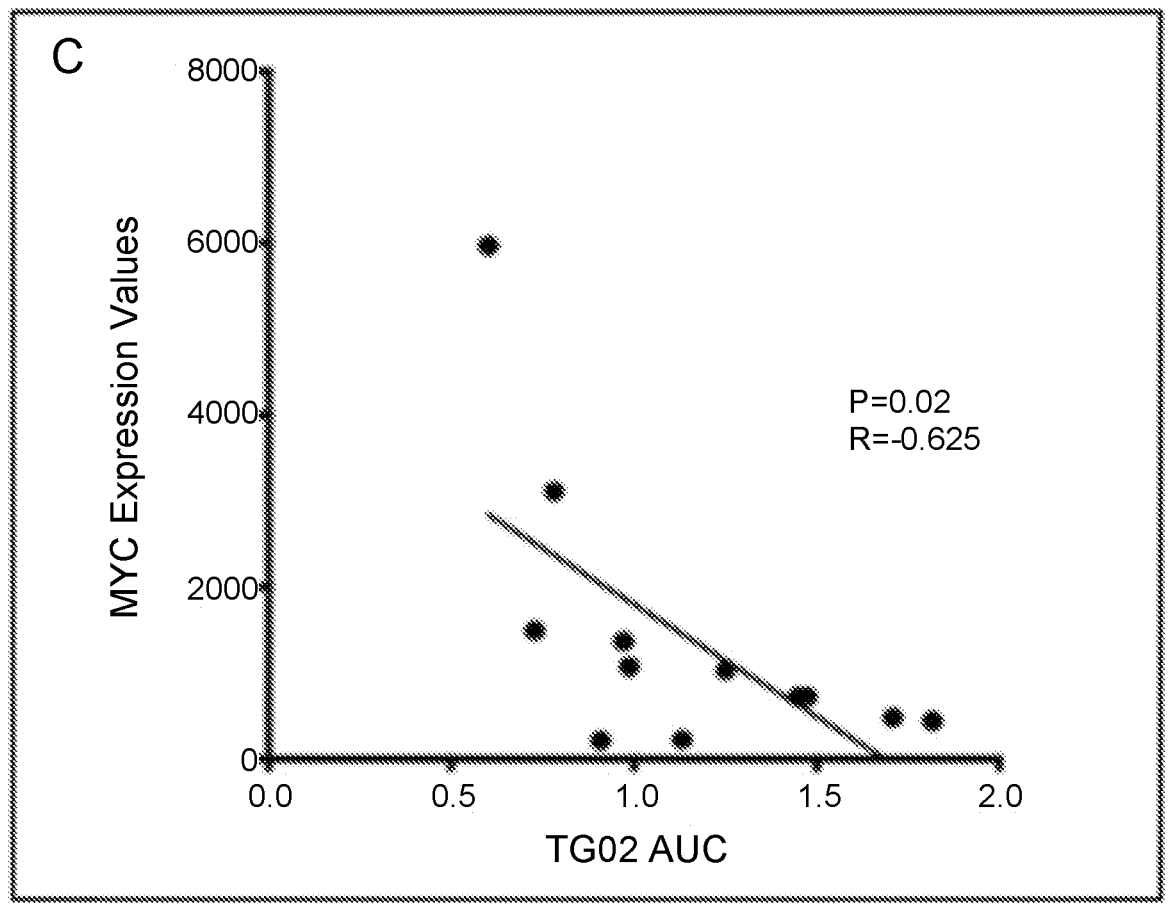
FIG. 30 is a scatter graph showing that high MYC expression correlates with low AUC in GBM cells.

Downregulation of MYC and Mcl-1 was observed in MYC-amplified BT245 cell line as early as 6 hours, while complete downregulation was seen at 24 hours, which coincided with a significant increase in apoptosis (FIG. 28). The AUC of TG02 induced inhibition of cell viability was calculated in this cell line panel to correlate with MYC expression levels (FIG. 29). TG02 was a more potent inhibitor of PDCLs exhibiting high MYC expression (FIG. 30). In vitro sensitivity (AUC) negatively correlated with MYC expression in GBM cells (P value=0.02)

Example 10

Radiation is an effective treatment for glioblastoma. But tumor resistance and recurrence develops in all patients.

Figure 31:
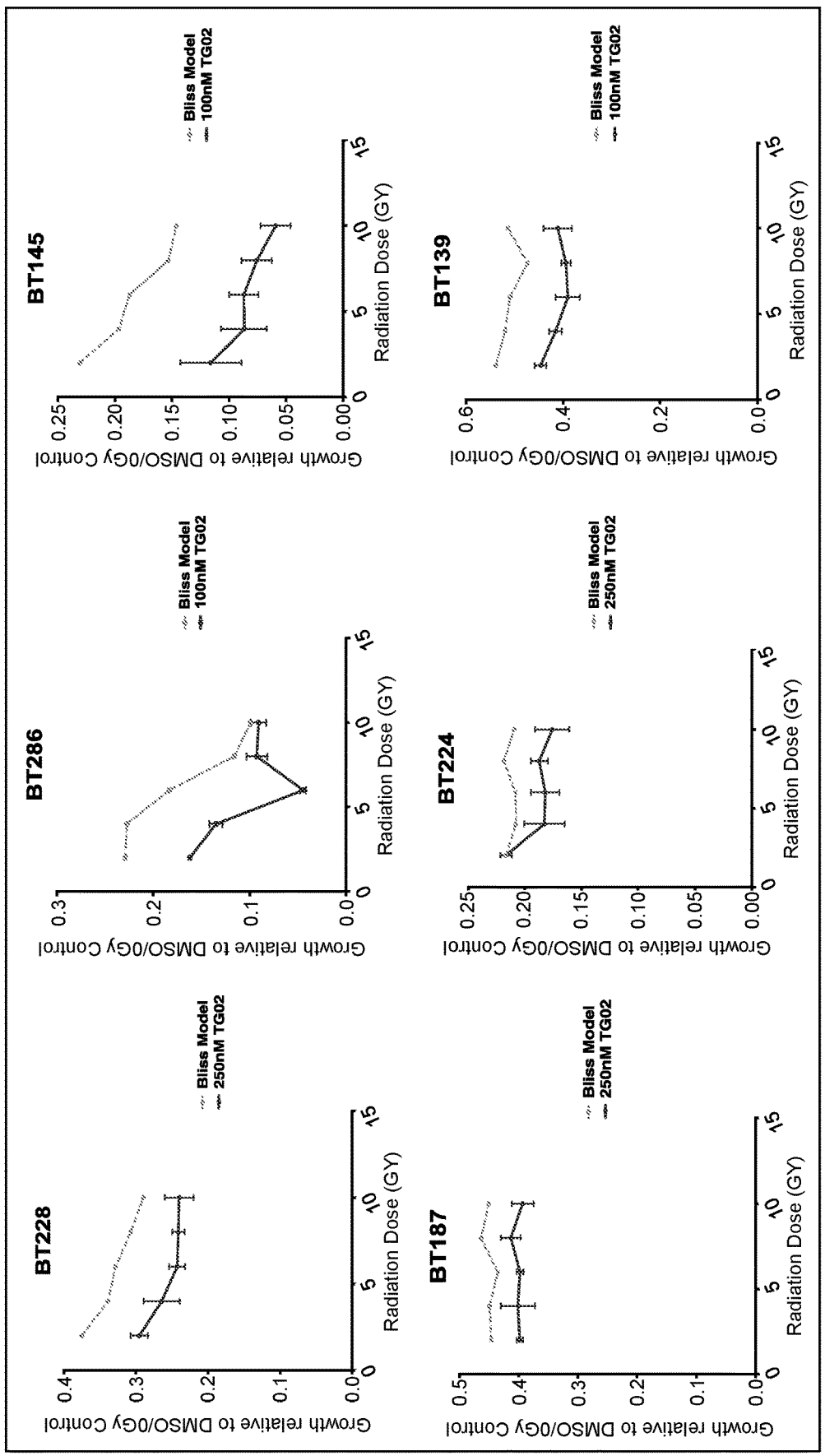
FIG. 31 is a series of six line graphs showing the activity of TG02 in combination with radiation in glioblastoma cell lines.

A panel of GBM PDCLs, see Example 9, were chosen for evaluation of the combination of TG02 and radiation therapy for the treatment of glioblastoma (FIG. 31). Cells were treated first with TG02 at increasing concentrations. Within 30 minutes, cells were treated with increasing doses of radiation and cell proliferation was measured 72 hours post-treatment. TG02 alone had anti-proliferative activity in these cell lines. The addition of TG02 augmented the effects radiation in a synergistic manner. The combination of TG02 and radiation exceeds the Bliss predicted model (greater than a 10% change from the Bliss predicted model), demonstrating synergy between TG02 and radiation in multiple PDCLs.

Example 11

TG02 Activity Correlates with MYC Expression in Glioblastoma Cell Lines

Figure 32:
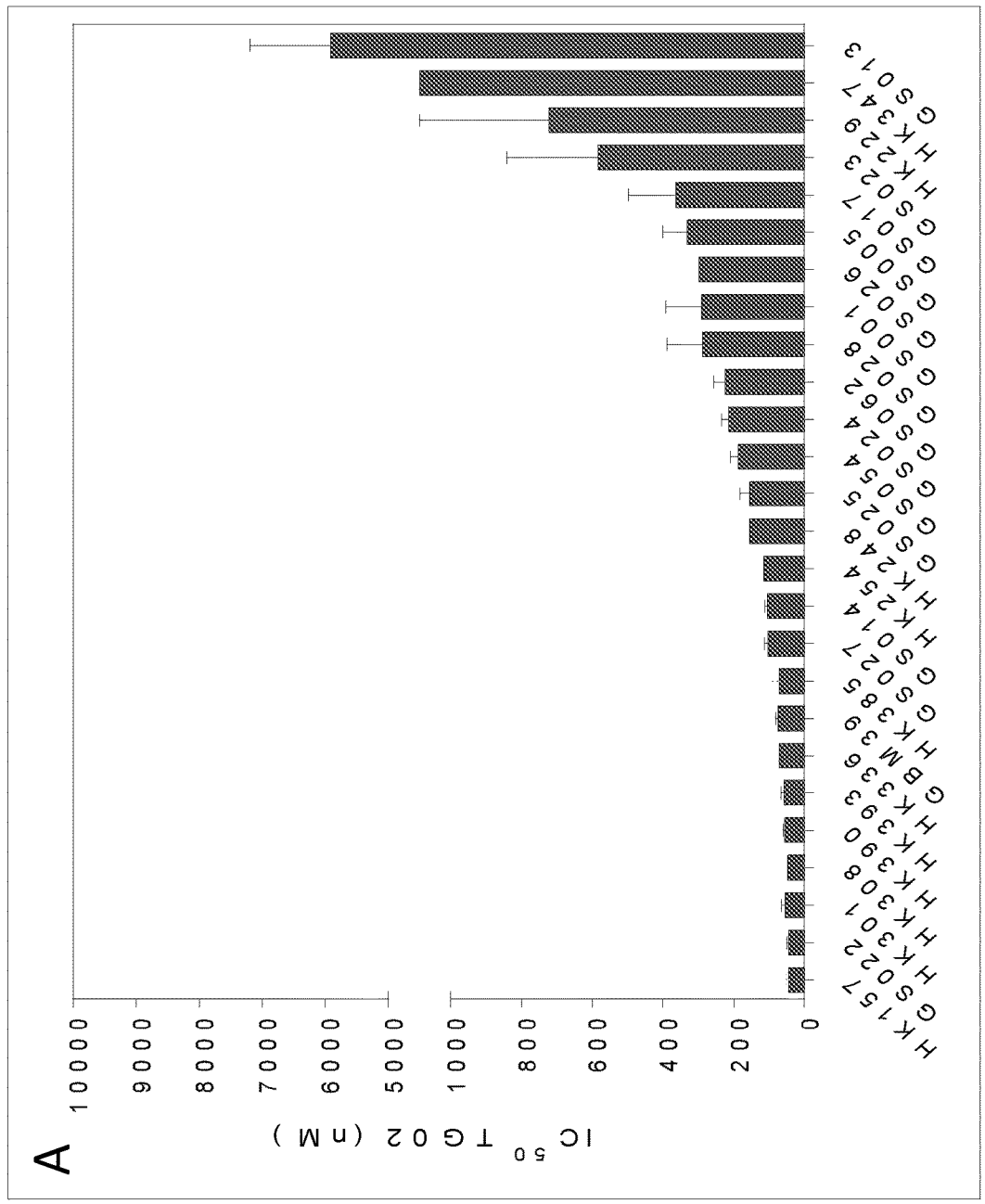
FIG. 32 is a bar graph showing the activity of TG02 on 26 patient-derived GBM stem cell lines.

In a panel of 26 patient-derived GBM stem cell lines, the activity of TG02 on GBM stem cell proliferation was evaluated (FIG. 32). TG02 was potent in this panel with sixteen cell lines achieving an $IC_{50}$ of less than 250 nM.

Figure 33:
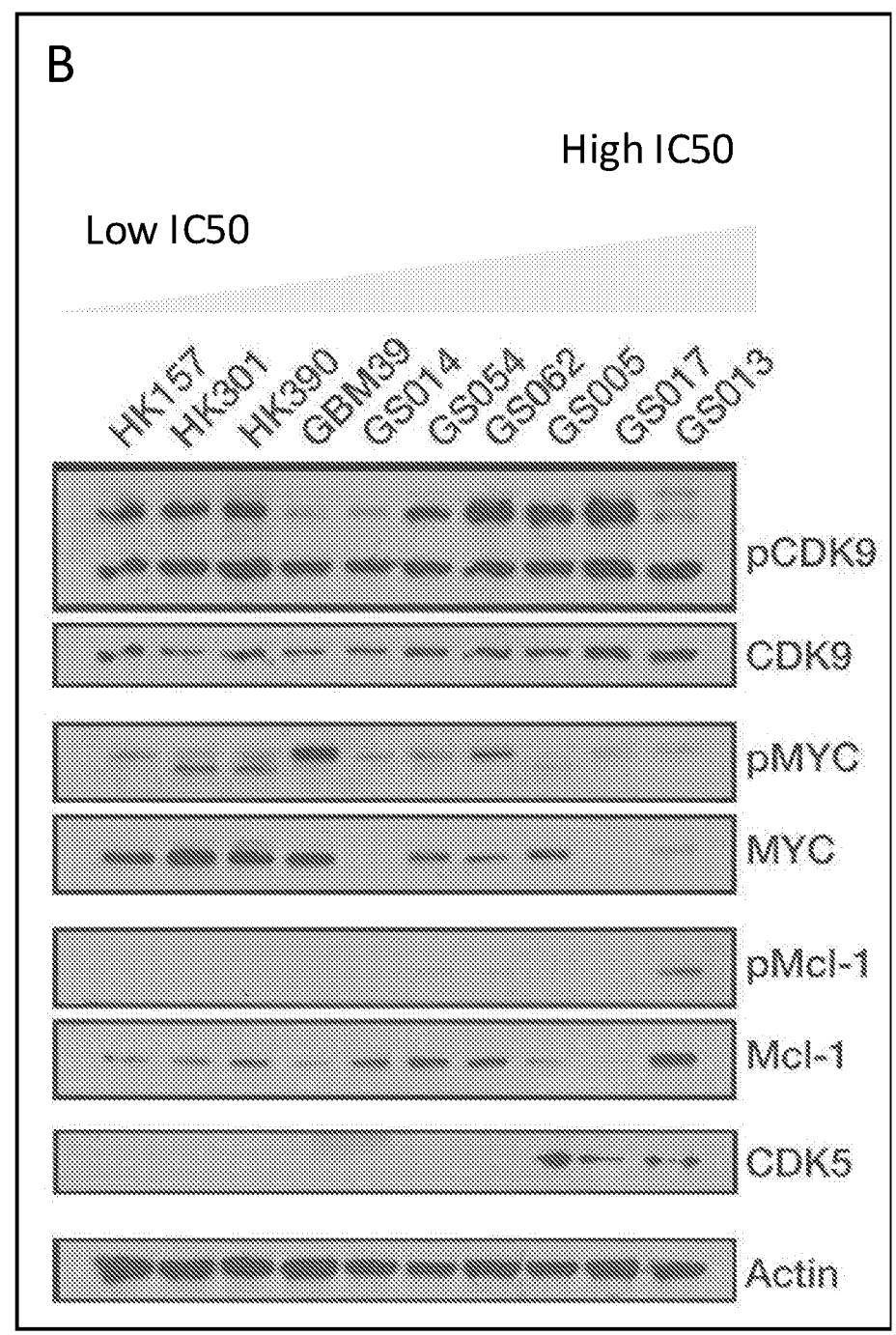
FIG. 33 is an illustration showing the expression level of CDK9, MYC, and Mcl-1 in patient-derived GBM stem cell lines following treatment with TG02.

The expression level of CDK9 and downstream markers, including MYC and Mcl-1, were measured to explore whether a correlation exists between protein expression and $IC_{50}$ values in this GBM panel. High MYC expression was found to correlate with greater sensitivity to TG02 treatment (FIG. 33).

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entirety.

What is claimed is:

1. A method of treating a patient having cancer, the method comprising administering to the patient a therapeutically effective amount of (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene and radiotherapy, wherein MYC overexpression, MCL1 overexpression, or MYC and MCL1 overexpression is differentially present in a biological sample taken from the patient as compared with a biological sample taken from a subject of another phenotypic status.

2. The method of claim 1, wherein (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene is administered to the patient before radiotherapy.

3. The method of claim 1, wherein (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene is administered to the patient after radiotherapy.

4. The method of claim 1, wherein a therapeutically effective amount of (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene is administered to the patient at the same time as radiotherapy.

5. The method of claim 1, wherein the cancer is selected from the group consisting of acoustic neuroma, acute lymphoblastic leukemia, acute monocytic leukemia, acute promyelocytic leukemia, adenocarcinoma, adult T-cell leukemia/lymphoma, alveolar rhabdomyosarcoma, angiosarcoma, astrocytoma, B-cell chronic lymphocytic leukemia, B-cell prolymphocytic leukemia, B-cell lymphoma, basal cell carcinoma, bladder cancer, blastoma, Burkitt's lymphoma, breast cancer, brain cancer, carcinoma, carcinoma in situ, carcinosarcoma, chondroma, chordoma, choriocarcinoma, craniopharyngioma, cervical cancer, colorectal cancer, diffuse large B-cell lymphoma, embryonal carcinoma, esophageal cancer, fibrosarcoma, follicular lymphoma, follicular thyroid cancer, ganglioneuroma, germ cell tumor, gestational choriocarcinoma, glioblastoma, glioma, hemangioblastoma, head and neck cancer, hematological malignancy, hepatoblastoma, hepatocellular carcinoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, liposarcoma, lung cancer, lymphangiosarcoma, acute lymphocytic leukemia, acute myelogeous leukemia, chronic lymphocytic leukemia, liver cancer, small cell lung cancer, non- small cell lung cancer, medullary carcinoma of the breast, medulloblastoma, melanoma, meningioma, multiple myeloma, myxosarcoma, neurinoma, neuroblastoma, neuroma, nodular melanoma, oligodendroglioma, oral cancer, osteosarcoma, ovarian cancer, Pancoast tumor, papillary thyroid cancer, prostate cancer, pancreatic cancer, pharyngeal cancer, pseudomyxoma periotonei, renal cell carcinoma, retinoblastoma, rhabdomyosarcoma, Richter's transformation, rectal cancer, sarcoma, Schwannomatosis, seminoma, skin cancer, small cell carcinoma, somatostatinoma, squamous cell carcinoma, synovial sarcoma, squamous carcinoma, stomach cancer, T-cell lymphoma, testicular cancer, thyroid cancer, uterine cancer, verrucous carcinoma, Waldenstrom's macroglobulinemia, Warthin's tumor, and Wilms' tumor.

6. The method of claim 1, wherein the cancer is selected from the group consisting of astrocytoma, hepatocellular carcinoma, lung cancer, breast cancer, head and neck cancer, prostate cancer, melanoma, multiple myeloma, glioma, glioblastoma, and colorectal cancer.

7. The method of claim 1, wherein the cancer is glioma.

8. The method of claim 1, wherein the cancer is glioblastoma.

* * * * *